United States Patent

Gibson et al.

(10) Patent No.: US 6,750,231 B2
(45) Date of Patent: Jun. 15, 2004

(54) 4-ARYLPIPERIDINE DERIVATIVES FOR THE TREATMENT OF PRURITUS

(75) Inventors: Stephen Paul Gibson, Sandwich (GB); Ivan Tommasini, Sandwich (GB); Kimberley Verrier, Sandwich (GB); Christopher James Dutton, Sandwich (GB); David Morris Gethin, Sandwich (GB); Douglas James Critcher, Sandwich (GB); Richard Edward Armer, Newhouse (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/100,981

(22) Filed: Mar. 19, 2002

(65) Prior Publication Data

US 2003/0004340 A1 Jan. 2, 2003

Related U.S. Application Data

(63) Continuation of application No. 09/576,792, filed on May 23, 2000, now abandoned.

(30) Foreign Application Priority Data

May 28, 1999 (GB) .............................. 9912417

(51) Int. Cl.7 .................... C07D 401/02; A61K 31/445
(52) U.S. Cl. .................. 514/326; 546/207; 546/208; 546/209; 546/210; 546/211; 546/212
(58) Field of Search ................... 546/210, 207, 546/208, 209, 211, 212; 514/326

(56) References Cited

U.S. PATENT DOCUMENTS

| | | | |
|---|---|---|---|
| 2,891,066 A | 6/1959 | Parcell |
| 4,081,450 A | 3/1978 | Zimmerman |
| 4,191,771 A | 3/1980 | Zimmerman |
| 4,737,505 A | 4/1988 | Guillaume et al. |
| 5,136,040 A | 8/1992 | Werner |
| 5,498,718 A | 3/1996 | Werner |

FOREIGN PATENT DOCUMENTS

| | | |
|---|---|---|
| DE | 4341403 | 6/1995 |
| EP | 0013078 | 7/1980 |
| EP | 0136863 | 4/1985 |
| EP | 0506468 | 3/1992 |
| EP | 0494717 | 7/1992 |
| EP | 0537980 | 4/1993 |
| EP | 0287339 | 8/1994 |
| EP | 0657428 | 6/1995 |
| EP | 0506478 | 9/1997 |
| EP | 0938898 | 9/1999 |
| GB | 1525584 | 9/1978 |
| GB | 2038812 | 7/1980 |
| GB | 2083476 | 3/1982 |
| WO | 9515327 | 6/1995 |
| WO | 9533729 | 12/1995 |
| WO | 9603400 | 2/1996 |
| WO | 9850358 | 11/1998 |
| WO | 9959971 | 11/1999 |
| WO | 9967237 | 12/1999 |
| WO | 0039089 | 7/2000 |

OTHER PUBLICATIONS

Yong–Woon Jung et al.; Vesamicol Receptor Mapping of Brain Cholinergic Neurons with Radioiodine–Labeled Positional Isomers of Benzovesamicol[1]; J. Med. Chem. (1996) vol. 39, pp 3331–3342.

Charles H. Mitch, et al.; 3,4–Dimethyl–4–(3– ydroxyphenyl)piperidines: Opioid Antagonists with Potent Anorectant Activity; J. Med. Chem. (1993) 36, 2842–2850.

Dennis M. Zimmerman, et al.; Structure–Activity Relationships of trans–3,4–Dimethyl–4–(3–hydroxyphenyl) piperidine Antagonists for $\mu$– and $\kappa$–Opioid Receptors; J. Med. Chem. (1993) 36, 2833–2841.

Patent Abstract of Japan, vol. 13, No. 179 (C–590), No Date Given.

Primary Examiner—Zinna Northington Davis
(74) Attorney, Agent, or Firm—Peter C. Richardson; Paul H. Ginsburg; Jolene W. Appleman

(57) ABSTRACT

There is provided a compound of formula I,

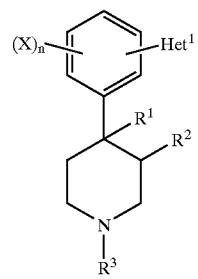

wherein Het[1], R[1], R[2], R[3], X and n have meanings given in the description, which are useful in the prophylaxis and in the treatment of diseases mediated by opiate receptors, such as pruritus.

22 Claims, No Drawings

4-ARYLPIPERIDINE DERIVATIVES FOR THE TREATMENT OF PRURITUS

This application is a continuation, under 35 U.S.C. 120 of U.S. Ser. No. 09/576,792, filed May 23, 2000 abandoned, which claims priority under 35 U.S.C. 119 of GB 9912417.4, filed May 28, 1999.

This invention relates to pharmaceutically useful compounds, in particular compounds that bind to opiate receptors (e.g. mu, kappa and delta opioid receptors).

Compounds that bind to such receptors are likely to be useful in the treatment of diseases mediated by opiate receptors, for example irritable bowel syndrome; constipation; nausea; vomiting; and pruritic dermatoses, such as allergic dermatitis and atopy in animals and humans. Compounds that bind to opiate receptors have also been indicated in the treatment of eating disorders, opiate overdoses, depression, smoking and alcohol addiction, sexual dysfunction, shock, stroke, spinal damage and head trauma.

There is a particular need for an improved treatment of itching. Itching, or pruritus, is a common dermatological symptom that can give rise to considerable distress in both humans and animals. Pruritus is often associated with inflammatory skin diseases which may be caused by hypersensitivity reactions, including reactions to insect bites, such as flea bites, and to environmental allergens, such as house dust mite or pollen; by bacterial and fungal infections of the skin; or by ectoparasite infections.

Existing treatments that have been employed in the treatment of pruritus include the use of corticosteroids and antihistamines. However, both of these treatments are known to have undesirable side effects. Other therapies that have been employed include the use of essential fatty acid dietary supplements, though these have the disadvantages of being slow to act, and of offering only limited efficacy against allergic dermatitis. A variety of emollients such as soft paraffin, glycerine and lanolin are also employed, but with limited success.

Thus, there is a continuing need for alternative and/or improved treatments of pruritus.

Certain 4-arylpiperidine-based compounds are disclosed in inter alia European patent applications EP 287339, EP 506468, EP 506478 and *J. Med. Chem.* 1993, 36, 2833–2850 as opioid antagonists. In addition, International Patent Application WO 95/15327 discloses azabicycloalkane derivatives useful as neuroleptic agents.

According to the invention there is provided compounds of formula I:

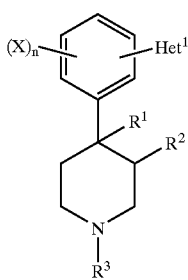

wherein $Het^1$ represents a 5- or 6-membered heterocyclic ring comprising at least one atom selected from nitrogen, oxygen and sulfur, which ring is optionally fused to a 5- or 6-membered ring, which latter ring optionally contains one or more heteroatoms selected from nitrogen, oxygen and/or sulfur, and which heterocyclic ring system ($Het^1$) is option-
ally substituted by one or more substituents selected from halo, nitro, —OH, =O, $Si(R^{4a})(R^{4b})(R_{4c})$, $N(R^{5a})(R^{5b})$, $SR^{6a}$, $N(R^{6b})S(O)_2R^{7a}$, $N(R^{6c})C(O)OR^{7b}$, $N(R^{6d})C(O)R^{7c}$, $C_1$–$C_6$ alkyl, $C_1$–$C_6$ alkoxy or $C_3$–$C_6$ cycloalkyl (which latter three groups are optionally substituted by one or more halo atoms); $R^{4a}$ to $R^{4c}$ independently represent $C_1$–$C_6$ alkyl or aryl;

$R^{5a}$ and $R^{5b}$ independently represent H, $C_1$–$C_6$ alkyl, $C_1$–$C_4$ alkylphenyl, aryl (which latter three groups are optionally substituted by one or more substituents selected from OH, nitro, amino, halo, $C_1$–$C_4$ alkyl or $C_1$–$C_4$ alkoxy (which latter two groups are optionally substituted by one or more halo atoms)) or, together with the N-atom to which they are attached, form a 4- to 6-membered heterocyclic ring (which ring is optionally substituted by one or more substituents selected from $C_1$–$C_4$ alkyl, $C_1$–$C_4$ alkoxy, OH, =O, nitro, amino or halo);

$R^{6a}$ to $R^{6d}$ each independently represent H, $C_1$–$C_6$ alkyl, $C_1$–$C_4$ alkylphenyl or aryl (which latter three groups are optionally substituted by one or more substituents selected from OH, nitro, amino, halo, $C_1$–$C_4$ alkyl or $C_1$–$C_4$ alkoxy (which latter two groups are optionally substituted by one or more halo atoms));

$R^{7a}$ to $R^{7c}$ independently represent $C_1$–$C_6$ alkyl, $C_1$–$C_4$ alkylphenyl or aryl, which four groups are all optionally substituted by one or more substituents selected from OH, nitro, amino, halo, $C_1$–$C_4$ alkyl or $C_1$–$C_4$ alkoxy (which latter two groups are optionally substituted by one or more halo atoms);

$R^1$ and $R^2$ are each independently H or $C_1$–$C_4$ alkyl;

$R^3$ represents aryl (optionally substituted by one or more substituents selected from OH, nitro, halo, CN, $CH_2CN$, $CONH_2$, $C_1$–$C_4$ alkyl, $C_1$–$C_4$ alkoxy, $C_1$–$C_5$ alkanoyl (which latter three groups are optionally substituted by one or more halo atoms) and —N($R^{8a}$)($R^{8b}$)), $C_1$–$C_{10}$ alkyl, $C_3$–$C_{10}$ alkenyl or $C_3$–$C_{10}$ alkynyl wherein said alkyl, alkenyl or alkynyl groups are optionally substituted and/or terminated by one or more substituents selected from $OR^{8c}$, $S(O)_pR^{8d}$, CN, halo, $C_2$–$C_6$ alkanoyl, $C_1$–$C_6$ alkoxy carbonyl, $C_2$–$C_6$ alkanoyloxy, $C_3$–$C_8$ cycloalkyl, $C_4$–$C_9$ cycloalkanoyl, $N(R^{9a})S(O)_2R^{10}$, $Het^2$, aryl, adamantyl (which latter two groups are optionally substituted by one or more substituents selected from OH, nitro, amino, halo, CN, $CH_2CN$, $CONH_2$, $C_1$–$C_4$ alkyl, $C_1$–$C_4$ alkoxy and $C_1$–$C_5$ alkanoyl (which latter three groups are optionally substituted by one or more halo atoms)), or —W—$A^1$—N($R^{9b}$)($R^{9c}$);

p is 0, 1 or 2;

W represents a single bond, C(O) or $S(O)_q$;

$A^1$ represents a single bond or $C_1$–$C_{10}$ alkylene;

provided that when both W and $A^1$ represent single bonds, then the group —N($R^{9b}$)($R^{9c}$) is not directly attached to an unsaturated carbon atom;

q is 0, 1 or 2;

$R^{8a}$ to $R^{8d}$ each independently represent H, $C_1$–$C_{10}$ alkyl, $C_3$–$C_{10}$ alkenyl, $C_3$–$C_{10}$ alkynyl, $C_3$–$C_8$ cycloalkyl, $C_1$–$C_4$ alkylphenyl, aryl (which latter six groups are optionally substituted by or one or more substituents selected from OH, nitro, amino, halo, CN, $CH_2CN$, $CONH_2$, $C_1$–$C_4$ alkyl, $C_1$–$C_4$ alkoxy and $C_1$–$C_5$ alkanoyl (which latter three groups are optionally substituted by one or more halo atoms)) or $Het^3$;

provided that $R^{8d}$ does not represent H when p represents 1 or 2;

$R^{9a}$ to $R^{9c}$ each independently represent H, $C_1$–$C_{10}$ alkyl, $C_3$–$C_{10}$ alkenyl, $C_3$–$C_{10}$ alkynyl, $C_3$–$C_8$ cycloalkyl, $C_1$–$C_4$ alkylphenyl, aryl (which latter six groups are optionally substituted by or one or more substituents selected from OH, nitro, amino, halo, CN, $CH_2CN$, $CONH_2$, $C_1$–$C_4$ alkyl, $C_1$–$C_4$ alkoxy and $C_1$–$C_5$ alkanoyl (which latter three groups are optionally substituted by one or more halo atoms)), Het⁴, or $R^{9b}$ and $R^{9c}$ together represent unbranched $C_2$–$C_6$ alkylene which alkylene group is optionally interrupted by O, S and/or an $N(R^{11})$ group and is optionally substituted by one or more $C_1$–$C_4$ alkyl groups;

$R^{10}$ represents $C_1$–$C_6$ alkyl, $C_3$–$C_8$ cycloalkyl, $C_1$–$C_4$ alkylphenyl or aryl, which four groups are optionally substituted by or one or more substituents selected from $C_1$–$C_4$ alkyl, $C_1$–$C_4$ alkoxy, OH, nitro, amino or halo;

$R^{11}$ represents H, $C_1$–$C_6$ alkyl, $C_3$–$C_8$ cycloalkyl, $A^2$—($C_3$–$C_8$ cycloalkyl) or $A^2$-aryl;

$A^2$ represents $C_1$–$C_6$ alkylene;

Het², Het³ and Het⁴ independently represent 3-to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, $C_1$–$C_4$ alkyl, $C_1$–$C_4$ alkoxy and $C_1$–$C_5$ alkanoyl (which latter three groups are optionally substituted by one or more halo atoms);

X is H, halo, $C_1$–$C_4$ alkyl or $C_1$–$C_4$ alkoxy (which latter two groups are optionally substituted by one or more halo atoms);

n is 0, 1 or 2;

or pharmaceutically, or veterinarily, acceptable derivatives thereof;

which compounds are referred to together hereinafter as "the compounds of the invention."

In the definitions used herein, alkyl, alkylene, alkoxy, alkoxy carbonyl, alkanoyl, alkanoyloxy, alkenyl, alkynyl and the alkyl parts of alkylphenyl and aryl alkoxy groups may, when there is a sufficient number of carbon atoms, be straight or branched-chain and/or optionally interrupted by one or more oxygen and/or sulfur atom(s). The term halo includes fluoro, chloro, bromo or iodo. The term "aryl" includes optionally substituted phenyl, naphthyl and the like, and "aryloxy" includes optionally substituted phenoxy and naphthyloxy and the like. Unless otherwise specified, aryl and aryloxy groups are optionally substituted by one or more (e.g. one to three) substituents selected from OH, nitro, amino, halo, CN, $CH_2CN$, $CONH_2$, $C_1$–$C_4$ alkyl, $C_1$–$C_4$ alkoxy $C_1$–$C_4$ alkoxy carbonyl and $C_1$–$C_5$ alkanoyl (which latter four groups are optionally substituted by one or more halo atoms).

The heterocyclic rings that Het¹, Het², Het³ and Het⁴ represent may be fully saturated, partially unsaturated and/or wholly or partially aromatic in character. Specific rings that may be mentioned include: for Het¹, adenine, benzimidazole, benzoxadiazole, benzoxazole, benzthiazole, cinnoline, cytosine, furan, furoxan, guanine, hydroxypyridine, hypoxanthine, imidazole, 1H-imidazo[4,5-b]pyrazine, indole, isoquinoline, isothiazole, isoxazole, 1,2,4-oxadiazole, 1,2,5-oxadiazole, 1,3,4-oxadiazole, oxazole, phthalazine, purine, pyrazine, pyrazole, pyridazine, pyridine, pyridine N-oxide, pyrimidine, pyrrole, quinazoline, quinoline, quinoxaline, 4,5,6,7-tetrahydrobenzimidazole, 4,5,6,7-tetrahydrobenzoxazole, 4,5,6,7-tetrahydro-1H-imidazo[4,5-b]-pyrazine, 1,2,4,5-tetrazine, tetrazole, 1,2,3-thiadiazole, 1,2,4-thiadiazole, 1,2,5-thiadiazole, 1,3,4-thiadiazole, thiazole, thiophene, thymine, 1,2,3-triazine, 1,2,4-triazine, 1,3,5-triazine, 1,2,3-triazole, 1,2,4-triazole and uracil; for Het², dioxane, dioxolane, morpholine, piperidine, perhydroazepine, tetrahydrofuran, tetrahydropyran or tetrazole. Substituents on Het¹, Het², Het³, and Het⁴ groups may be located at any point on the ring/fused ring system.

For the avoidance of doubt, when Het (Het¹, Het², Het³ and Het⁴) groups are at least part-saturated, possible points of substitution include the atom (e.g. the carbon atom) at the point of attachment of the Het group to the rest of the molecule. Het², Het³ and Het⁴ groups may also be attached to the rest of the molecule via a heteroatom.

The piperidine moiety in compounds of formula I may be in N-oxidised form. Sulfur atoms that may interrupt (e.g. alkyl) substituents in compounds of formula I may be present in oxidised form (e.g. as sulfoxides or sulfones). All Het¹, Het², Het³ and Het⁴ groups may also be in N- or S-oxidized forms.

The term "pharmaceutically, or veterinarily, acceptable derivatives" includes non-toxic salts. Salts which may be mentioned include: acid addition salts, for example, salts formed with sulfuric, hydrochloric, hydrobromic, phosphoric, hydroiodic, sulfamic, organo-sulfonic, citric, carboxylic (e.g. acetic, benzoic, etc.), maleic, malic, succinic, tartaric, cinnamic, ascorbic and related acids; base addition salts; salts formed with bases, for example, the sodium, potassium and $C_1$–$C_4$ alkyl ammonium salts.

The compounds of the invention may also be in the form of quaternary ammonium salts, e.g. at the piperidine moiety, which salts may be formed by reaction with a variety of alkylating agents, such as an alkyl halide or an ester of sulfuric, or an aromatic sulfonic, acid.

The compounds of the invention may exhibit tautomerism. All tautomeric forms of the compounds of formula I are included within the scope of the invention.

The compounds of the invention contain one or more asymmetric centres and thus they can exist as enantiomers and diastereomers. Diastereoisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. The invention includes the use of both the separated individual isomers as well as mixtures of isomers.

Also included within the scope of the invention are radio-labelled derivatives of compounds of formula I which are suitable for biological studies.

Preferred compounds of the invention include those wherein:

Het¹ is attached in the meta- position relative to the piperidine ring;

$R^1$ represents $C_1$–$C_2$ alkyl;

$R^2$ represents H or $C_1$–$C_2$ alkyl;

$R^3$ represents saturated $C_1-C_{10}$ (e.g. $C_1-C_8$) alkyl, optionally interrupted by oxygen and/or optionally substituted and/or terminated by one or more substituents selected from CN, halo, $C_1-C_6$ alkoxy carbonyl, $C_2-C_6$ alkanoyl, $C_2-C_6$ alkanoyloxy, $C_3-C_8$ cycloalkyl, $C_4-C_9$ cycloalkanoyl, $OR^{8c}$, $N(R^{9a})S(O)_2R^{10}$, $Het^2$, phenyl (which latter group is optionally substituted by one or more substituents selected from OH, $C_1-C_4$ alkyl, $C_1-C_4$ alkoxy, $C_2-C_5$ alkanoyl, halo, nitro, amino, CN, $CH_2CN$, $CONH_2$ and $CF_3$), and/or $—W—A^1—N(R^{9b})(R^{9c})$;

$R^{8c}$ represents H, $C_1-C_6$ alkyl, $C_3-C_8$ cycloalkyl, $C_1-C_4$ alkylphenyl or phenyl (which latter two groups are optionally substituted by one or more substituents selected from OH, $C_1-C_4$ alkyl, $C_1-C_4$ alkoxy, $C_2-C_5$ alkanoyl, halo, nitro, amino, CN, $CH_2CN$, $CONH_2$ and $CF_3$);

$R^{9a}$ to $R^{9c}$ each independently represent H, $C_1-C_4$ alkyl, $C_1-C_2$ alkylphenyl or phenyl (which latter two groups are optionally substituted by or one or more substituents selected from $C_1-C_2$ alkyl, $C_1-C_2$ alkoxy, OH or halo);

$R^{10}$ represents $C_1-C_4$ alkyl or aryl, which two groups are optionally substituted by or one or more substituents selected from $C_1-C_2$ alkyl, $C_1-C_2$ alkoxy, nitro or halo;

W represents C(O) or $S(O)_2$;

$A^1$ represents a single bond or $C_1-C_4$ alkylene.

More preferred compounds of the invention include those wherein:

$Het^1$ represents one of the rings specifically identified hereinbefore in respect of $Het^1$;

$R^1$ represents methyl;

$R^2$ represents H or methyl;

$R^3$ represents linear, saturated $C_1-C_7$ alkyl, optionally substituted by one or more substituents selected from CN, halo, $C_1-C_2$ alkoxy carbonyl, $OR^{8c}$, $N(H)S(O)_2R^{10}$, $Het^2$, phenyl (which latter group is optionally substituted by one or more substituents selected from $C_1-C_2$ alkyl, $C_1-C_2$ alkoxy and halo), or $C(O)N(R^{9b})(R^{9c})$;

$R^{8c}$ represents H, $C_1-C_4$ alkyl, phenyl or $C_1-C_2$ alkylphenyl (which latter three groups are optionally substituted by one or more substituents selected from $C_1-C_2$ alkyl, $C_1-C_2$ alkoxy and halo);

$R^{9b}$ and $R^{9c}$ independently represent H, $C_1-C_4$ alkyl or $C_1-C_2$ alkylphenyl;

$R^{10}$ represents $C_1-C_2$ alkyl;

X represents halo, particularly fluoro;

n represents 1 or, preferably, 0.

Still further preferred compounds of the invention include those wherein:

$Het^1$ represents a 5- or 6-membered heterocyclic ring comprising at least one nitrogen and/or at least one oxygen atom, which ring is optionally substituted by one or more substituents selected from $Si(R^{4a})(R^{4b})(R^{4c})$, halo, thiobenzyl or $C_1-C_6$ alkyl;

$R^1$ and $R^2$ both represent methyl groups in the mutually trans configuration;

$R^3$ represents benzyl, 2-(benzyloxy)ethyl, N-benzyl-3-propanamido, 2-butoxyethyl, n-butyl, N,N-diethyl-3-propanamido, 3-(2,5-dimethoxy-phenoxy)propyl, 2-(1,3-dioxan-2-yl)ethyl, 4-(1,3-dioxolan-2-yl)butyl, 2-(1,3-dioxolan-2-yl)ethyl, 2-ethanesulfonamidoethyl, 1-ethoxycarbonyl-methyl, 3-ethoxypropyl, 2-(4-fluorophenyl)ethyl, 6-hexanenitrile, n-hexyl, 3-hydroxy-3-phenylpropyl, 4-methoxybutyl, 5-methoxycarbonylpentyl, 2-(2-methoxyethoxy)ethyl, 2-(3-methylphenyl)ethyl, 3-(4-morpholino)-propyl, 5-pentanenitrile, n-pentyl, 2-(1-perhydroazepinyl) ethyl, 2-phenoxyethyl, 3-phenoxypropyl, 2-phenylethyl, 3-phenylpropyl, 2-(1-piperidino)ethyl, 3-(1-piperidino)propyl, N-propyl-3-propanamido, 2-propoxyethyl, 3-tetrahydro-3-furanylpropyl, 3-tetrahydro-2H-pyran-2-ylpropyl or 3-(tetrazol-1-yl)-propyl;

$R^{4a}$ to $R^{4c}$ independently represent $C_1-C_6$ alkyl.

Particularly preferred compounds of the invention include those wherein:

$Het^1$ represents preferably unsubstituted 2- or 4-imidazole, tetrazole, 5-oxazole, 5-isoxazole, 4- or 5-pyrazole, 1,2,3- or 1,2,4-triazole.

Preferred compounds of the invention include the compounds of the Examples described hereinafter.

According to a further aspect of the invention there is provided processes for the preparation of compounds of the invention, as illustrated below.

The following processes are illustrative of the general synthetic procedures which may be adopted in order to obtain the compounds of the invention.

1. Compounds of formula I may be prepared by transition-metal- (for example, palladium-) catalysed cross-coupling between a compound of formula II,

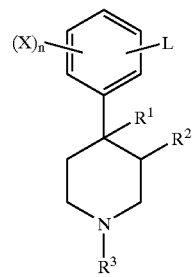

II wherein L is a suitable leaving group such as halogen, preferably bromine or iodine, or a sulfonate such as trifluoromethanesulfonate, and $R^1$, $R^2$, $R^3$, X and n are as hereinbefore defined, with a compound of formula III, $Het^1—M$  III where M is a tin-containing moiety (e.g. tributylstannyl), a boron derivative (e.g. a boronic acid), or a zinc halide (which may be formed in situ from the corresponding halide) and $Het^1$ is as hereinbefore defined, for example at between room temperature and boiling point in a reaction-inert solvent (e.g. dimethylformamide) in the presence of an appropriate coupling agent (e.g. palladium(II) chloride, tris (dibenzylideneacetone)-dipalladium(0) combined with triphenylarsine, or tetrakis(triphenyl-phosphine)palladium (0)).

2. Compounds of formula I in which $Het^1$ represents 1H-1,2,3-triazol-4-yl, optionally substituted by $Si(R^{4a})(R^{4b})(R^{4c})$, $C_1-C_6$ alkyl or $C_1-C_6$ haloalkyl, wherein $R^{4a}$ to $R^{4c}$ are as hereinbefore defined, may be prepared by reaction of a nitrile of formula IV,

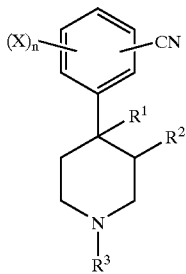

IV wherein $R^1$, $R^2$, $R^3$, X and n are as hereinbefore defined, with a compound of formula V,

$R^{12}CHN_2$  V wherein $R^{12}$ represents H, $Si(R^{4a})(R^{4b})(R^{4c})$ or $C_1$–$C_6$ alkyl, which latter group is optionally substituted by one or more halo atoms, and $R^{4a}$ to $R^{4c}$ are as hereinbefore defined, for example at between −10° C. and room temperature in the presence of a suitable strong base (e.g. n-butyllithium) and a reaction-inert organic solvent (tetrahydrofuran).

Compounds of formula IV may be prepared by reaction of a compound of formula VI,

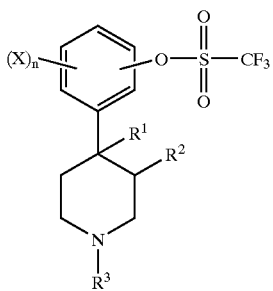

VI wherein $R^1$, $R^2$, $R^3$, X and n are as hereinbefore defined with an alkali metal cyanide (e.g. potassium cyanide), for example at raised temperature in the presence of a reaction-inert solvent (e.g. N-methylpyrrolidine) and a suitable catalyst (e.g. palladium(II) acetate combined with 1,1'-bis(diphenylphosphino)ferrocene).

Compounds of formula VI may be prepared by reaction of a corresponding compound of formula VII,

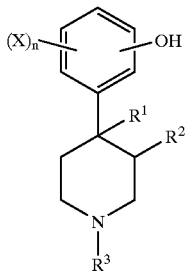

VII wherein $R^1$, $R^2$, $R^3$, X and n are as hereinbefore defined, with an appropriate triflating agent (e.g. N-phenyltrifluoromethanesulfonimide), for example at between 0° C. and room temperature in the presence of a reaction-inert organic solvent (e.g. dichloromethane) and a suitable base (e.g. triethylamine).

Compounds of formula VII may be prepared by reaction of a corresponding compound of formula VIII,

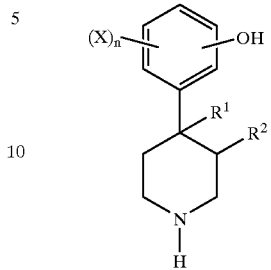

VIII with a compound of formula IX,

$R^3L^1$  IX wherein $R^3$ is as hereinbefore defined, and $L^1$ represents a leaving group (e.g. halo, alkanesulfonate, perfluoroalkanesulfonate or arenesulfonate), under conditions that are known to those skilled in the art, which include, for example, alkylation at between room temperature and reflux temperature in the presence of a reaction-inert organic solvent (e.g. N,N-dimethylformamide) and a suitable base (e.g. $NaHCO_3$), and arylation at between room temperature and reflux temperature in the presence of a suitable catalyst system (e.g. tris(dibenzylideneacetone)palladium(0) combined with tri-o-tolylphosphine), an appropriate strong base (e.g. sodium tert-butoxide) and a reaction-inert solvent (e.g. toluene).

3. Compounds of formula I in which $Het^1$ represents 1H-1,2,4-triazol-4-yl, optionally substituted by an $R^{12}$ group, wherein $R^{12}$ is as hereinbefore defined, may be prepared by reaction of an imidate of formula X,

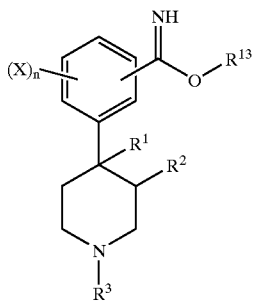

X wherein $R^{13}$ represents $C_1$–$C_6$ alkyl, and $R^1$, $R^2$, $R^3$, X and n are as hereinbefore defined, with a compound of formula XI,

$H_2NNHCOR^{12}$  XI wherein $R^{12}$ is as hereinbefore defined, for example at between room temperature and reflux temperature in the presence of a suitable organic solvent (e.g. an alcohol), followed by, if necessary, continued heating of the reaction until completion in the absence of solvent.

Compounds of formula X may be prepared by methods well known to those skilled in the art. For example, compounds of formula X may be prepared by saturating a solution of a corresponding nitrile of formula IV, as hereinbefore defined, in an alcohol of formula $R^{13}OH$, wherein $R^{13}$ is as hereinbefore defined, with gaseous HCl, for example at 0 to 50° C.

4. Compounds of formula I in which Het¹ represents 1H-1,3-imidazol-2-yl, optionally substituted by up to two R¹² groups, wherein R¹² is as hereinbefore defined, may be prepared by reaction of a corresponding compound of formula X, as hereinbefore defined, with a compound of formula XII,

wherein independent substituents R¹²ᵃ and R¹²ᵇ represent R¹², and R¹² is as hereinbefore defined, for example at between room temperature and reflux temperature in the presence of a suitable organic solvent (e.g. an alcohol), followed by, if necessary, continued heating of the reaction until completion in the absence of solvent.

5. Compounds of formula I in which Het¹ represents 1H-benzimidazol-2-yl, 1H-benzoxazol-2-yl, 1H-benzthiazol-2-yl (all of which are optionally substituted in the benzene ring part) may be prepared by reaction of a corresponding compound of formula X, as hereinbefore defined, with a compound of formula XIII,

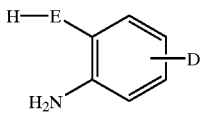

wherein D represents one to four substituents as defined hereinbefore in respect of Het¹ and E represents O, S or NH, under conditions known to those skilled in the art, for example at between room temperature and reflux temperature in the presence of a suitable organic solvent (e.g. an alcohol), followed by, if necessary, continued heating of the reaction until completion in the absence of solvent.

6. Compounds of formula I in which Het¹ represents 5-chloro-1,2,4-thiadiazol-3-yl may be prepared by reaction of a corresponding compound of formula XIV,

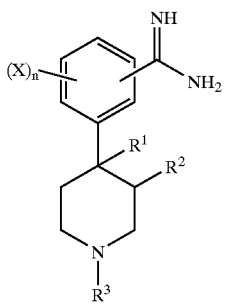

or a suitable (e.g. hydrogen halide) adduct thereof, wherein R¹, R², R³, X and n are as hereinbefore defined, with trichloromethanesulfenyl chloride, for example at between −10 and +10° C. in the presence of a reaction-inert solvent (e.g. dichloromethane) and optionally in the presence of a suitable base (e.g. aqueous sodium hydroxide).

Compounds of formula XIV may be prepared by reaction of a compound of formula IV, as hereinbefore defined, with ammonia and/or or a suitable adduct thereof (e.g. a hydrohalide), for example at between room temperature and 100° C., optionally at elevated pressure and optionally in the presence of a suitable solvent (e.g. water, a lower alkyl alcohol such as methanol or ethanol, or an appropriate mixture thereof).

7. Compounds of formula I in which Het¹ represents 1H-1,3-imidazol-4-yl may be prepared by desulfurisation of a corresponding compound of formula I in which Het¹ represents 2-thiobenzylated 1H-1,3-imidazol-4-yl, for example using Raney® nickel in the presence of a suitable organic solvent (e.g. ethanol) and an appropriate base (e.g. sodium hydroxide).

8. Compounds of formula I in which Het¹ represents 2-thiobenzylated 1H-1,3-imidazol-4-yl may be prepared by reaction of a corresponding α-halocarbonyl compound of formula XV,

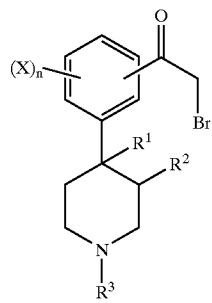

wherein R¹, R², R³, X and n are as hereinbefore defined with 2-benzyl-2-thiopseudourea, for example at between room temperature and reflux temperature in the presence of a reaction-inert organic solvent (e.g. N,N-dimethylformamide) and a suitable base (e.g. potassium carbonate).

Compounds of formula XV may be prepared by reaction of a corresponding methylketone of formula XVI,

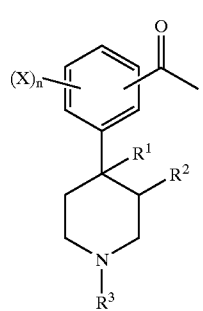

wherein R¹, R², R³, X and n are as hereinbefore defined, with trimethylsilylchloride, for example at between −78 and −10° C. in the presence of a strong base (e.g. lithium bis(trimethylsilyl)amide) and a reaction-inert organic solvent (e.g. tetrahydrofuran), followed by reaction with bromine.

Compounds of formula XVI may be prepared by reaction of a corresponding triflate of formula VI, as hereinbefore defined, with a compound that provides a suitable source of an acyl anion equivalent (e.g. vinyl butyl ether), for example at between room temperature and reflux temperature in the presence of an appropriate catalyst (e.g. palladium(II) acetate combined with 1,1'-bis(diphenylphosphino) ferrocene), an organic base (e.g. triethylamine) and a suitable solvent (e.g. N,N-dimethyl-formamide), followed by hydrolysis of the resulting enol ether under conditions known to those skilled in the art (for example, by reaction at room temperature with aqueous hydrochloric acid).

Alternatively, compounds of formula XVI may be prepared by reaction of a compound corresponding to a nitrile of formula IV with a methyl-delivering organometallic compound (e.g. methyl lithium), for example at between −80 and 10° C. in the presence of a reaction-inert organic solvent (e.g. tetrahydrofuran).

9. Compounds of formula I in which Het¹ represents 1H-tetrazol-5-yl may be prepared by reaction of a corresponding compound of formula IV, as hereinbefore defined, with a suitable source of the azide ion (e.g. trimethylsilyl azide), for example at between room temperature and reflux temperature in the presence of a reaction-inert solvent (e.g. toluene) and an appropriate Lewis-acidic catalyst (e.g. dibutyltin oxide).

10. Compounds of formula I wherein $R^3$ represents $C_1$ alkyl optionally substituted by $C_3$–$C_8$ cycloalkyl, $Het^2$, aryl, adamantyl, (which latter two groups are optionally substituted by one or more substituents selected from OH, nitro, amino, halo, CN, $CH_2CN$, $CONH_2$, $C_1$–$C_4$ alkyl, $C_1$–$C_4$ alkoxy and $C_1$–$C_5$ alkanoyl (which latter three groups are optionally substituted by one or more halo atoms)), or $R^3$ represents $C_2$–$C_{10}$ alkyl, $C_3$–$C_{10}$ alkenyl or $C_3$–$C_{10}$ alkynyl (which three groups are all optionally substituted by one or more of the relevant substituents identified hereinbefore in respect to $R^3$), which alkyl, alkenyl or alkynyl groups are attached to the piperidine nitrogen atom via a $CH_2$ group, wherein $Het^2$ is as hereinbefore defined, may be prepared by reduction of a corresponding compound of formula XVII,

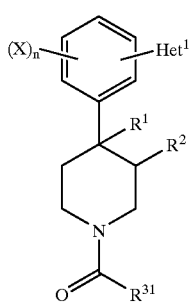

XVII wherein $R^{31}$ represents H, $C_3$–$C_8$ cycloalkyl, $Het^2$, aryl, adamantyl, (which latter two groups are optionally substituted by one or more substituents selected from OH, nitro, amino, halo, CN, $CH_2CN$, $CONH_2$, $C_1$–$C_4$ alkyl, $C_1$–$C_4$ alkoxy and $C_1$–$C_5$ alkanoyl (which latter three groups are optionally substituted by one or more halo atoms)), $C_1$–$C_9$ alkyl, $C_2$–$C_9$ alkenyl or $C_2$–$C_9$ alkynyl, which alkyl, alkenyl or alkynyl groups are optionally substituted and/or terminated by one or more substituents selected from $OR^{8c}$, $S(O)_pR^{8d}$, CN, halo, $C_1$–$C_6$ alkoxy carbonyl, $C_2$–$C_6$ alkanoyl, $C_2$–$C_6$ alkanoyloxy, $C_3$–$C_8$ cycloalkyl, $C_4$–$C_9$ cycloalkanoyl, $N(R^{9a})S(O)_2R^{10}$, $Het^2$, aryl, adamantyl (which latter two groups are optionally substituted by one or more substituents selected from OH, nitro, amino, halo, CN, $CH_2CN$, $CONH_2$, $C_1$–$C_4$ alkyl, $C_1$–$C_4$ alkoxy and $C_1$–$C_5$ alkanoyl (which latter three groups are optionally substituted by one or more halo atoms)), or —W—$A^1$—$N(R^{9b})(R^{9c})$, and $R^1$, $R^2$, $R^{8c}$, $R^{8d}$, $R^{9a}$ to $R^{9c}$, $R^{10}$, $Het^1$, $Het^2$, n, p, W, X and $A^1$ are as hereinbefore defined, using a suitable reducing agent (e.g. lithium aluminium hydride or a borane derivative), for example as described hereinbefore.

Compounds of formula XVII may be prepared by reaction of a corresponding compound of formula XVIII,

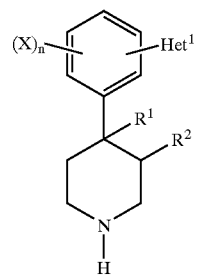

XVIII wherein $Het^1$, $R^1$, $R^2$, X and n are as hereinbefore defined with a compound of formula XIX, $R^{31}CO_2H$      XIX or a suitable (e.g. carboxylic acid) derivative thereof (e.g. an acid halide or anhydride), wherein $R^{31}$ is as hereinbefore defined, using coupling conditions known to those skilled in the art.

Compounds of formulae XVII and XVIII may be prepared from appropriate precursors by analogy with methods disclosed herein that describe to the introduction, or formation, of a $Het^1$ group.

11. Compounds of formula I in which $Het^1$ represents 1H-pyrazol-3-yl may be prepared by reaction of a corresponding α,β-unsaturated ketone of formula XX,

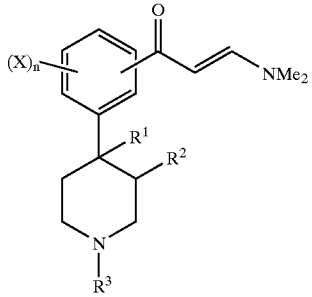

XX wherein $R^1$, $R^2$, $R^3$, X and n are as hereinbefore defined, with hydrazine, for example at between room temperature and reflux temperature in the presence of a reaction-inert solvent (e.g. a methanol/water mixture).

Compounds of formula XX may be prepared by aldol condensation of a corresponding methyl ketone of formula XVI, as hereinbefore defined, with dimethylaminoacetaldehyde dimethylacetal, for example at between room temperature and reflux temperature in the presence of a reaction-inert organic solvent (e.g. N,N-dimethylformamide).

12. Compounds of formula I wherein $Het^1$ represents 1H-pyrazol-4-yl may be prepared by reaction of a corresponding compound of formula VI, as hereinbefore defined, with a compound of formula XXI,

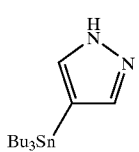

XXI for example at between room temperature and reflux temperature in the presence of a reaction-inert solvent (e.g.

N,N-dimethylformamide), an appropriate coupling agent (e.g. tris(dibenzylideneacetone)dipalladium(0) combined with triphenylarsine) and a suitable source of a halide ion (e.g. lithium chloride).

13. Compounds of formula I wherein Het¹ represents oxazol-5-yl, thiazol-5-yl or imidazol-5-yl (which three groups are all optionally substituted in the 4-position by $R^{12}$, wherein $R^{12}$ is as hereinbefore defined, and which imidazol-5-yl group is substituted at the 1-position by $C_1$–$C_6$ alkyl, $C_1$–$C_6$ alkoxy or $C_3$–$C_6$ cycloalkyl (which latter three groups are optionally substituted by one or more halo atoms)) may be prepared by reaction of a corresponding compound of formula XXII,

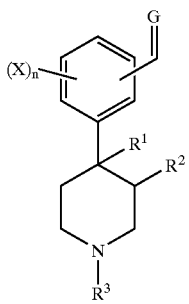

XXII wherein G represents $NR^{14}$, O or S, $R^{14}$ represents $C_1$–$C_6$ alkyl, $C_1$–$C_6$ alkoxy or $C_3$–$C_6$ cycloalkyl (which latter three groups are optionally substituted by one or more halo atoms), and $R^1$, $R^2$, $R^3$, X and n are as hereinbefore defined, with a compound of formula XXIII,

 XXIII wherein $L^2$ represents a group capable, when attached to a $C_2$ alkylene unit, of undergoing 1,2-elimination (relative to the $L^2$ group, e.g. an alkyl or aryl sulfoxide or sulfone), and $R^{12}$ is as hereinbefore defined, for example at between room and reflux temperature in the presence of an appropriate base (e.g. potassium carbonate) and a reaction-inert solvent (e.g. a lower alkyl alcohol, such as methanol).

Compounds of formula XXII in which G represents O may be prepared from a corresponding vinyl derivative of formula XXIV,

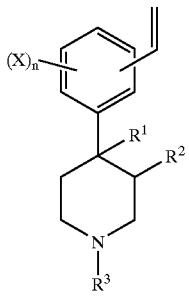

XXIV wherein $R^1$, $R^2$, $R^3$, X and n are as hereinbefore defined, by reaction with a suitable dihydroxylating reagent (e.g. sub-stoichiometric $OsO_4$ combined with morpholine N-oxide), for example at between 0° C. and reflux temperature in the presence of a reaction-inert solvent (e.g. a water/acetone mixture) and an appropriate reagent to effect 1,2-diol oxidative cleavage (e.g. sodium periodate).

Compounds of formula XXII in which G represents $NR^{14}$, wherein $R^{14}$ is as hereinbefore defined, may be prepared by reaction of a corresponding compound in which G represents O with a compound of formula XXV,

 XXV wherein $R^{14}$ is as hereinbefore defined, for example at between room and reflux temperature in the presence of a reaction-inert solvent (e.g. a lower alkyl alcohol such as methanol or ethanol), and optionally in the presence of a suitable Lewis-acidic catalyst.

Compounds of formula XXII in which G represents S may be prepared by reaction of a corresponding compound in which G represents O with a reagent that effects oxygen-sulfur exchange (e.g. Lawesson's Reagent), for example at between room and reflux temperature in the presence of a reaction-inert solvent (e.g. toluene).

Compounds of formula XXIV can be prepared from a corresponding compound of formula VI, as hereinbefore defined, by reaction with a suitable source of vinyl anion equivalent (e.g. vinyltributyltin), for example at between room temperature and reflux temperature in the presence of a reaction-inert solvent (e.g. THF), an appropriate coupling agent (e.g. tetrakis(triphenylphosphine)palladium(0)) and a suitable source of halide ion (e.g. lithium chloride).

14. Compounds of formula I wherein Het¹ represents isoxazol-5-yl may be prepared by reaction of a corresponding compound of formula XX, as hereinbefore defined, with a suitable form of hydroxylamine, for example at between room temperature and reflux temperature in the presence of a reaction-inert solvent (e.g. a methanol/water mixture).

15. Compounds of formula I in which Het¹ represents 1H-1,2,3-triazol-4-yl, optionally substituted by $Si(R^{4a})(R^{4b})(R^{4c})$, $C_1$–$C_6$ alkyl or $C_1$–$C_6$ haloalkyl or halo, wherein $R^{4a}$ to $R^{4c}$ are as hereinbefore defined, may alternatively be prepared by reaction of a corresponding compound of formula XXVI,

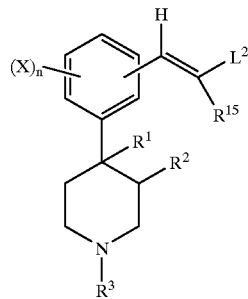

XXVI wherein $R^{15}$ represents H, $Si(R^{4a})(R^{4b})(R^{4c})$, halo or $C_1$–$C_6$ alkyl, which latter group is optionally substituted by one or more halo atoms, and $R^1$, $R^2$, $R^3$, $R^{4a}$ to $R^{4c}$, $L^2$, X and n are as hereinbefore defined, with a suitable source of the azide ion (e.g. sodium azide), for example at between room and reflux temperature in the presence of a reaction-inert solvent (e.g. N,N-dimethylformamide).

Compounds of formula XXVI may be prepared by reaction of a compound of formula XXII, as hereinbefore defined, in which G represents O, with a compound of formula XXVII,

 XXVII wherein $L^2$ and $R^{15}$ are as hereinbefore defined, for example at between −80° C. and room temperature in the presence of a strong base (e.g. n-butyl lithium) and a reaction-inert solvent (e.g. THF), followed by dehydration of the resultant hydroxy compound under conditions well known to those skilled in the art (e.g. by reaction with methanesulfonyl chloride in the presence of triethylamine).

16. Compounds of formula I may be prepared by reaction of a corresponding compound of formula XVIII, as hereinbefore defined, with a compound of formula IX, as hereinbefore defined, under conditions that are well known to those skilled in the art, for example as described hereinbefore in respect of the production of compounds of formula VII.

17. Compounds of formula I wherein $R^3$ represents $C_1$ alkyl, which, in place of being optionally substituted by the substituents as defined hereinbefore, is instead optionally substituted by $R^{31}$, wherein $R^{31}$ is as hereinbefore defined, may be prepared by reaction of a corresponding compound of formula XVIII, as hereinbefore defined, with a compound of formula XXVIII, $$R^{31}CHO \qquad\qquad XXVIII$$

wherein $R^{31}$ is as hereinbefore defined, for example in the presence of a suitable reducing agent (e.g. sodium borohydride, sodium cyano-borohydride or sodium triacetoxyborohydride) and an appropriate solvent (e.g. methanol).

18. Compounds of formula I wherein $R^3$ is a $C_1$–$C_{10}$ alkyl, $C_4$–$C_{10}$ alkenyl or $C_4$–$C_{10}$ alkynyl group that is fully saturated from 1- to 3-C (relative to the piperidine N-atom), and which $R^3$ group is substituted at 2-C (relative to the piperidine N-atom) by $S(O)R^{8d}$, $S(O)_2R^{8d}$, alkanoyl, cycloalkanoyl, alkoxy carbonyl, CN, —C(O)—A$^1$—N(R$^{9b}$)(R$^{9c}$), —S(O)—A1—N(R$^{9b}$)(R$^{9c}$), or —S(O)$_2$—A$^1$—N(R$^{9b}$)(R$^{9c}$), wherein $R^{8d}$, $R^{9b}$, $R^{9c}$ and $A^1$ are as hereinbefore defined, may be prepared by reaction of a corresponding compound of formula XVIII, as hereinbefore defined, with a compound of formula XXIX, $$R^{3a}\text{—}Z \qquad\qquad XXIX$$

wherein $R^{3a}$ represents $R^3$ as hereinbefore defined except that it does not represent aryl, and that the $R^{3a}$ chain contains an additional carbon-carbon double bond α,β to the Z-substituent, and Z represents $S(O)R^{8d}$, $S(O)_2R^{8d}$, alkanoyl, cycloalkanoyl, alkoxy carbonyl, CN, —C(O)—A$^1$—N(R$^{9b}$)(R$^{9c}$), —S(O)—A$^1$—N(R$^{9b}$)(R$^{9c}$), or —S(O)$_2$—A$^1$—N(R$^{9b}$)(R$^{9c}$), wherein $R^{8d}$, $R^{9b}$, $R^{9c}$ and $A^1$ are as hereinbefore defined, for example at between room and reflux temperature in the presence of a reaction-inert solvent (e.g. THF).

Compounds of formulae II, III, V, VIII, IX, XI, $R^{13}OH$, XII, XIII, XIX, XXI, XXIII, XXIV, XXVII, XXVIII, XXIX, and derivatives thereof, when not commercially available or not subsequently described, may be obtained either by analogy with the processes described herein, or by conventional synthetic procedures, in accordance with standard techniques, from readily available starting materials using appropriate reagents and reaction conditions. For example, Het$^1$ or Het$^1$-M groups in compounds of formulae I, III, XVII, XVIII and XXI may also be prepared by, or by analogy with, the methods disclosed in European patent application EP 590 971, Houben-Weyl Methods of Organic Chemistry, Additional and Supplementary Volumes to the 4$^{th}$ Edition (Volumes E6a, E6b, E6b$_2$, E7a, E7b, E8a, E8b, E8c, E8d, E9, E9a), edited by E Schaumann and R Kreher, Thieme (Stuttgart) or Comprehensive Heterocyclic Chemistry II, edited by A R Katritsky, C W Rees and E F V Scriven, 1$^{st}$ Edition, Elsevier Science Ltd., Volumes 1–11 (1996). Conventional synthetic procedures, and standard techniques also include, for example, those relating to process 1 described hereinbefore, examples of which may be found in: "Palladium Reagents in Organic Synthesis" RF Heck, Academic Press (1985); "Comprehensive Organometallic Chemistry", edited by AG Davies, 2$^{nd}$ Edition, Volume 12, Chapter 3, Section D, Pergamon Press (1995); J K Stille, Angew. Chem. Intl. Ed. Eng., 1986, 25, 508; A Suzuki, N Niyaura, Chem. Rev. 1995, 95, 2457; "Organometallics in Synthesis A Manual", M. Schlosser, John Wiley and Sons (1994); "Metal-catalysed Cross-coupling Reactions", F Diedrich and P J Stang, Wiley-Vch (1998); and "Palladium Reagents and Catalysts Innovations in Organic Synthesis", J Tsuji, John Wiley and Sons (1995), the disclosures in which documents are hereby incorporated by reference.

Substituents on alkyl, heterocyclic and aryl groups in the above-mentioned compounds may also be introduced, removed and interconverted, using techniques which are well known to those skilled in the art (including those specifically disclosed hereinbefore). For example, nitro may be reduced to amino, OH may be alkylated to give alkoxy, alkoxy and alkanoyloxy may be hydrolysed to OH, alkenes may be hydrogenated to alkanes, halo may be hydrogenated to H, etc.

In some cases it is possible to introduce further substituents into the compounds of formula I directly. For example, chlorination of the phenyl group of compounds of formula I, may be performed by reaction with a solution of chlorine in acetic acid.

It will be appreciated by those skilled in the art that heterocycles prepared by the processes described hereinbefore may, if desired, be further substituted by, for example, halogen, nitro and —SR, by treatment with electrophilic reagents such as halosuccinimides, nitric acid and sulfenyl halides. It will further be understood that these substituents may be subjected to further transformations, for example reduction of nitro groups and subsequent acylation or alkylation of the resultant amino groups, to provide further examples within the scope of the invention. These methodologies and their applicability will be known and understood by the skilled person.

Thus, the skilled person will appreciate that various standard substituent or functional group interconversions and transformations within certain compounds of formula I will provide other compounds of formula I.

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include oxo, hydroxy, amino and carboxylic acid. Suitable protective groups for oxo include acetals, ketals (e.g. ethylene ketals) and dithianes. Suitable protective groups for hydroxy include trialkylsilyl and diarylalkylsilyl groups (e.g. tert-butyldimethylsilyl, tert-butyldiphenylsilyl or trimethylsilyl) and tetrahydropyranyl. Suitable protective groups for amino include benzyl, tert-butyloxycarbonyl, 9-fluorenylmethoxycarbonyl or benzyloxycarbonyl. Suitable protective groups for carboxylic acid include $C_1$–$C_6$ alkyl or benzyl esters.

The protection and deprotection of functional groups may take place before or after any of the reaction steps described hereinbefore.

Protective groups may be removed in accordance with techniques which are well known to those skilled in the art. The use of protecting groups is fully described in "Protective Groups in Organic Chemistry", edited by JWF McOmie, Plenum Press (1973), and "Protective Groups in Organic Synthesis", $2^{nd}$ edition, TW Greene & PGM Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis. The procedures may be adapted as appropriate to the reactants, reagents and other reaction parameters in a manner that will be evident to the skilled person by reference to standard textbooks and to the examples provided hereinafter.

It will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula I may act as prodrugs of other compounds of formula I.

It will be further appreciated by those skilled in the art, that certain moieties, known to those skilled in the art as "pro-moieties", for example as described in 'Design of Prodrugs' by H. Bundgaard, Elsevier, 1985 (the disclosure in which document is hereby incorporated by reference), may be placed on appropriate functionalities, when such functionalities are present within compounds of formula I.

All protected derivatives, and prodrugs, of compounds of formula I are included within the scope of the invention.

Pharmaceutically acceptable acid addition salts of the compounds of formula I which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formula I with the appropriate base. Both types of salt may be formed or interconverted using ion-exchange resin techniques.

The above procedures may be adapted as appropriate to the particular reactants and groups involved and other variants will be evident to the skilled chemist by reference to standard textbooks and to the examples provided hereafter to enable all of the compounds of formula I to be prepared.

The compounds of the invention are useful because they possess pharmacological activity in animals, especially mammals including humans. They are therefore indicated as pharmaceuticals and, in particular, for use as animal medicaments.

According to a further aspect of the invention there is provided the compounds of the invention for use as medicaments, such as pharmaceuticals and animal medicaments.

By the term "treatment", we include both therapeutic (curative) or prophylactic treatment.

In particular, the compounds of the invention have been found to be useful in the treatment of diseases mediated via opiate receptors, which diseases include irritable bowel syndrome; constipation; nausea; vomiting; pruritus; and conditions characterised by pruritus as a symptom.

Thus, according to a further aspect of the invention there is provided the use of the compounds of the invention in the manufacture of a medicament for the treatment of a disease mediated via an opiate receptor. There is further provided the use of the compounds of the invention in the manufacture of a medicament for the treatment of irritable bowel syndrome; constipation; nausea; vomiting; pruritus or a medical condition characterised by pruritus as a symptom.

The compounds of the invention are thus expected to be useful for the curative or prophylactic treatment of pruritic dermatoses including allergic dermatitis and atopy in animals and humans. Other diseases and conditions which may be mentioned include contact dermatitis, psoriasis, eczema and insect bites.

Thus, the invention provides a method of treating or preventing a disease mediated via an opiate receptor. There is further provided a method of treating irritable bowel syndrome; constipation; nausea; vomiting; pruritus or a medical condition characterised by pruritus as a symptom in an animal (e.g. a mammal), which comprises administering a therapeutically effective amount of a compound of the invention to an animal in need of such treatment.

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses (see below).

While it is possible to administer a compound of the invention directly without any formulation, the compounds are preferably employed in the form of a pharmaceutical, or veterinary, formulation comprising a pharmaceutically, or veterinarily, acceptable carrier, diluent or excipient and a compound of the invention. The carrier, diluent or excipient may be selected with due regard to the intended route of administration and standard pharmaceutical, and/or veterinary, practice. Pharmaceutical compositions comprising the compounds of the invention may contain from 0.1 percent by weight to 90.0 percent by weight of the active ingredient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (e.g. subcutaneously, intramuscularly or intravenously), or as an implant. Such formulations may be prepared in a conventional manner in accordance with standard veterinary practice.

The formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

The compositions are preferably formulated in a unit dosage form, each dosage containing from about 1 to about 500 mg, more usually about 5 to about 300 mg, of the active ingredient. The term "unit dosage form" refers to physically discreet units suitable as unitary dosages for human subjects and other mammals, each unit containing a predetermined quantity of active material calculated to produce the desired therapeutic effect, in association with a suitable pharmaceutical carrier.

In any event, the veterinary practitioner, or the skilled person, will be able to determine the actual dosage which will be most suitable for an individual patient, which may vary with the species, age, weight and response of the particular patient. The above dosages are exemplary of the average case; there can, of course, be individual instances where higher or lower dosage ranges are merited, and such are within the scope of this invention.

For veterinary use, the compounds of the invention are of particular value for treating pruritus in domestic animals such as cats and dogs and in horses.

As an alternative for treating animals, the compounds may be administered with the animal feedstuff and for this purpose a concentrated feed additive or premix may be prepared for mixing with the normal animal feed.

For human use, the compounds are administered as a pharmaceutical formulation containing the active ingredient together with a pharmaceutically acceptable diluent or carrier. Such compositions include conventional tablet, capsule and ointment preparations which are formulated in accordance with standard pharmaceutical practice.

Compounds of the invention may be administered either alone or in combination with one or more agents used in the treatment or prophylaxis of disease or in the reduction or suppression of symptoms. Examples of such agents (which are provided by way of illustration and should not be construed as limiting) include antiparasitics, e.g. fipronil, lufenuron, imidacloprid, avermectins (e.g. abamectin, ivermectin, doramectin), milbemycins, organophosphates, pyrethroids; antihistamines, e.g. chlorpheniramine, trimeprazine, diphenhydramine, doxylamine; antifungals, e.g. fluconazole, ketoconazole, itraconazole, griseofulvin, amphotericin B; antibacterials, e.g. enroflaxacin, marbofloxacin, ampicillin, amoxycillin; anti-inflammatories e.g. prednisolone, betamethasone, dexamethasone, carprofen, ketoprofen; dietary supplements, e.g. gamma-linoleic acid; and emollients. Therefore, the invention further provides a product containing a compound of the invention and a compound from the above list as a combined preparation for simultaneous, separate or sequential use in the treatment of diseases mediated via opiate receptors.

The skilled person will also appreciate that compounds of the invention may be taken as a single dose on an "as required" basis (i.e. as needed or desired).

Thus, according to a further aspect of the invention there is provided a pharmaceutical, or veterinary, formulation including a compound of the invention in admixture with a pharmaceutically, or veterinarily, acceptable adjuvant, diluent or carrier.

Compounds of the invention may also have the advantage that, in the treatment of human and/or animal patients, they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds of the present invention were determined by the following test method.
Biological Test Compounds of the present invention have been found to display activity in binding assays selective for the mu opioid receptor in dog brain. The assays were conducted by the following procedure.

Laboratory bred beagles were used as a source of dog brain tissue. Animals were euthanised, their brains removed and the cerebellum discarded. The remaining brain tissue was sectioned into small pieces approximately 3 g in weight and homogenised in 50 mM Tris pH 7.4 buffer at 4° C. using a Kinematica Polytron3 tissue homogeniser. The resulting homogenate was centrifuged at 48,400× g for 10 minutes and the supernatant discarded. The pellet was resuspended in Tris buffer and incubated at 37° C. for 10 minutes. Centrifugation, resuspension and incubation steps were repeated twice more, and the final pellet was resuspended in Tris buffer and stored at −80° C. Membrane material prepared in this manner could be stored for up to four weeks prior to use.

For mu assays, increasing concentrations of experimental compound, ($5\times10^{-12}$ to $10^{-5}$ M), Tris buffer and $^3$H ligand, ([D-Ala$^2$, N-Me-Phe$^4$,Gly-ol$^5$]-Enkephalin, DAMGO), were combined in polystyrene tubes. The reaction was initiated by the addition of tissue, and the mixture was incubated at room temperature for 90 minutes. The reaction was terminated by rapid filtration using a Brandel Cell Harvester3 through Betaplate3 GF/A glass fibre filters pre-soaked in 50 mM Tris pH 7.4, 0.1% polyethylenimine buffer. The filters were then washed three times with 0.5 mL ice-cold Tris pH 7.4 buffer. Washed filters were placed in bags and Starscint3 scintillant added. Bags containing the filters and scintillant were heat sealed and counted by a Betaplate3 1204 beta counter.

Duplicate samples were run for each experimental compound and the data generated was analysed using $IC_{50}$ analysis software in Graphpad Prism. Ki values were calculated using Graphpad Prism according to the following formula:

$$Ki=IC_{50}/1+[^3H\ ligand]/K_D$$

where $IC_{50}$ is the concentration at which 50% of the $^3$H ligand is displaced by the test compound and $K_D$ is the dissociation constant for the $^3$H ligand at the receptor site.

The invention is illustrated by the following Preparations and Examples in which the following abbreviations may be used:

APCI =atmospheric pressure chemical ionisation
br (in relation to NMR)=broad
DMF=N,N-dimethylformamide
DMSO=dimethylsulfoxide
d (in relation to time)=day
d (in relation to NMR)=doublet
dd (in relation to NMR)=doublet of doublets
dt (in relation to NMR)=doublet of triplets
EtOAc=ethyl acetate
EtOH=ethanol
ESI=electrospray ionisation
h=hour(s)
m (in relation to NMR)=multiplet
MeOH =methanol
min(s)=minute(s)
q (in relation to NMR)=quartet
s (in relation to NMR)=singlet
t (in relation to NMR)=triplet
THF=tetrahydrofuran When reverse phase HPLC is mentioned in the text the following 2 sets of conditions were employed.

Condition 1: A Phenomenex Magellen3 column, 150×21 mm, packed with 5μ $C_{18}$ silica, eluting with a gradient of acetonitrile: 0.1 M aqueous ammonium acetate (30:70 to 95:5 over 10 mins, flow rate 20 mL per min).

Condition 2: A Dynamax3 column, 42×250 mm, packed with 8μ $C_{18}$ silica, eluting with acetonitrile: 0.1 M aqueous ammonium acetate (30:70) at 45 mL per minute.

In both cases, combination and evaporation of appropriate fractions, determined by analytical HPLC, provided the desired compounds as acetate salts.

Analytical HPLC conditions used to highlight appropriate fractions were Phenomenex Magellan3 column, 4.6×150 mm, packed with 5μ $C_{18}$ silica, eluting with a gradient of acetonitrile: 0.1 M aqueous heptanesulfonic acid (10:90 to 90:10 over 30 min, followed by a further 10 min at 90:10) at 1 mL per minute. Column oven temperature was 40° C., and ultraviolet detection of components was made at 220 nM.

When column chromatography is referred to this usually refers to a glass column packed with silica gel (40–63 μm). Pressure of ~165 kPa is generally applied and the ratio of crude product:silica gel required for purification is typically 50:1. Alternatively, an Isolute SPE (solid phase extraction) column or Waters Sep-Pak3 cartridge packed with silica gel may be used under atmospheric pressure. The ratio of crude product to silica gel required for purification is typically 100:1.

The hydrochloride salt may be made by methods commonly known to those skilled in the art of synthetic chemistry. Typically, to a solution of free base in dichloromethane (1 g: 100 mL) was added ethereal hydrochloric acid (1.0 M, 1.2 equivalent), the excess solvent was decanted off and the remaining precipitate was washed three times with ether and then dried in vacuo.

Nuclear magnetic resonance (NMR) spectral data were obtained using a Varian Inova 300 or Varian Inova 400 spectrometer, the observed chemical shifts (δ) being consistent with the proposed structures. Mass spectral (MS) data were obtained on a Finnigan Masslab Navigator or a Fisons Instruments Trio 1000 spectrometer. The calculated and observed ions quoted refer to the isotopic composition of lowest mass. HPLC means high performance liquid chromatography. Room temperature means 20 to 25° C.

EXAMPLES

Example 1

1-Benzyl-3,4-dimethyl-4-(3-(5-(trimethylsilyl)-1H-1,2,3-triazol-4-yl)phenyl)piperidine To a solution of (trimethylsilyl)diazomethane (2.0 M in hexane, 9.86 mL, 19.7 mmol) in tetrahydrofuran (40 mL) at 0° C. under an atmosphere of nitrogen was added n-butyllithium (2.5 M in hexane, 7.9 mL, 19.7 mmol) dropwise. After 30 min, a solution of 1-benzyl-4-(3-cyanophenyl)-3,4-dimethylpiperidine (Preparation 3, 5.0 g, 16.4 mmol) in tetrahydrofuran (40 mL) was added such that the internal temperature remained at 0° C. After stirring overnight, the reaction was quenched with saturated aqueous sodium hydrogencarbonate (100 mL) and the mixture was extracted with ethyl acetate (3×100 mL). The combined organic extracts were dried over $MgSO_4$, filtered and concentrated in vacuo to give a pale brown foam (6.53 g, 79%).

NMR ($CDCl_3$, selected data for the free base): 0.3 (m, 9H), 0.8 (d, 3H), 1.35 (s, 3H), 7.2–7.5 (m, 9H).

MS (Finnigan): M/Z (MH$^+$) 419.2; $C_{25}H_{34}N_4Si+H$ requires 419.3.

Example 2

1-Benzyl-3,4-dimethyl-4-(3-(1H-1,2,3-triazol-4-yl)phenyl)-piperidine

A solution of 1-benzyl-3,4-dimethyl-4-(3-(5-(trimethylsilyl)-1H-1,2,3-triazol-4-yl)phenyl)piperidine (Example 1, 6.5 g, 15.8 mmol) in 2 N HCl/methanol (1:1, 100 mL) was heated at reflux overnight. After allowing to cool, the reaction mixture was adjusted to pH 10 using saturated aqueous sodium hydrogencarbonate solution (ca. 250 mL). The aqueous mixture was extracted with ethyl acetate (3×100 mL) and the combined extracts were washed with water (150 mL), followed by brine (150 mL) before drying over $MgSO_4$. The organic solution was filtered and the mother liquor concentrated in vacuo to provide the title compound as a cream solid (5.2 g, 95%).

NMR ($CDCl_3$, selected data for the free base): 0.8 (d, 3H), 1.4 (s, 3H), 3.4–3.6 (m, 2H), 7.2–7.4 (m, 7H), 7.6 (d, 1H), 7.8 (s, 1H), 7.95 (s, 1H MS (Finnigan): M/Z (MH$^+$) 347.2; $C_{22}H_{26}N_4+H$ requires 347.2.

Example 3

1-Hexyl-3,4-dimethyl-4-(3-(5-(trimethylsilyl)-1H-1,2,3-triazol-4-yl)phenyl)piperidine To a solution of (trimethylsilyl)diazomethane (2.0 M in hexane, 400 μL, 0.80 mmol) in tetrahydrofuran (10 mL) at 0° C. under an atmosphere of nitrogen was added n-butyllithium (2.5 M in diethyl ether, 320 μL, 0.80 mmol) dropwise. After 20 min, a solution of 4-(3-cyanophenyl)-1-hexyl-3,4-dimethylpiperidine (Preparation 6, 200 mg, 0.67 mmol) in tetrahydrofuran (5 mL) was added such that the internal temperature remained at 0° C. After stirring overnight, the reaction was quenched with saturated aqueous sodium hydrogencarbonate (25 mL) and the mixture was extracted with diethyl ether (3×25 mL). The extracts were washed with water and brine (10 mL each), dried over $MgSO_4$, filtered and concentrated in vacuo to give the title compound as a white foam which was used without further purification (266 mg, 96%).

NMR ($CDCl_3$, selected data for the free base): 0.35 (m, 9H), 0.8 (d, 3H), 0.9 (t, 3H), 1.4 (s, 3H), 7.3–7.5 (m, 4H), 7.5 (s, 1H).

Example 4

1-Hexyl-3,4-dimethyl-4-(3-(1H-1,2,3-triazol-4-yl)phenyl)piperidine

A solution of 1-hexyl-3,4-dimethyl-4-(3-(5-(trimethylsilyl)-1H-1,2,3-triazol-4-yl)phenyl)piperidine (Example 3, assume 0.64 mmol) in 2 N hydrochloric acid/methanol (1:1, 40 mL) was heated at 90° C. overnight. After allowing to cool, the reaction mixture was adjusted to pH 9 using solid sodium hydrogencarbonate. The aqueous mixture was extracted with ethyl acetate (3×20 mL) and the extracts were dried over $MgSO_4$, filtered and concentrated in vacuo to provide the title compound as a white solid (203 mg, 92%).

NMR ($CDCl_3$, selected data for the free base): 0.8 (d, 3H), 0.9 (t, 3H), 1.4 (s, 3H), 7.3 (d, 1H), 7.4 (t, 1H), 7.6 (d, 1H), 7.8 (s, 1H), 7.9 (s, 1H).

MS (APCI): M/Z (MH$^+$) 341.5; $C_{21}H_{32}N_4+H$ requires 341.3.

Example 5

3,4-Dimethyl-1-(3-(4-morpholino)propyl)-4-(3-(1H-1,2,3-triazol-4-yl)phenyl)piperidine A solution of 3,4-dimethyl-4-(3-(1H-1,2,3-triazol-4-yl)phenyl)piperidine (Preparation 44, 45 mg, 0.176 mmol) in tetrahydrofuran (4 mL) was treated with 1-(4-morpholinyl)-2-propen-1-one (30 mg, 0.212 mmol) and the resultant mixture was heated at 60° C. overnight. Concentration in vacuo gave a colourless oil (82 mg) which was dissolved in anhydrous tetrahydrofuran (1 mL) and stirred under an atmosphere of nitrogen. The solution was cooled in an ice bath and then treated with lithium aluminium hydride solution (1.0 M in tetrahydrofuran, 0.20 mL, 0.20 mmol) dropwise by a syringe. The resulting suspension was stirred overnight at room temperature then quenched with aqueous ammonium chloride solution (5 mL, half-saturated) and extracted with ethyl acetate (4×5 mL). The combined extracts were dried over $Na_2SO_4$, filtered and concentrated in vacuo to give a colourless oil (74 mg) which was partially purified by chromatography on silica gel (3.5 g) eluting with dichloromethane:ethanol:0.88 ammonia (100:8:1 to 50:8:1) to give partially-purified product (45 mg). Further purification by reversed phase preparative HPLC (condition 1) gave the acetate salt of the title compound (34 mg). The free base was obtained by treating with dilute aqueous ammonia solution (2 mL) and extracting with ether (3×3 mL). Drying over $Na_2SO_4$, filtering and evaporation to dryness gave the title compound as a colourless glass (20 mg, 30%).

NMR (CDCl$_3$, selected data for the free base): 0.8 (d, 3H), 1.4 (s, 3H), 1.7–1.9 (m, 3H), 2.1 (m, 1H), 2.35–2.75 (m, 12H), 2.95 (m, 1H), 3.75 (m, 4H), 7.3 (d, 1H), 7.4 (t, 1H), 7.55 (d, 1H), 7.8 (s, 1H), 7.95 (s, 1H).

MS (thermospray): M/Z (MH$^+$) 384.5; $C_{22}H_{33}N_5O$+H requires 384.3.

Example 6
3,4-Dimethyl-1-(3-(tetrazol-1-yl)propyl)-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 45 mg, 0.176 mmol) in N,N-dimethylformamide (4 mL) was added sodium hydrogencarbonate (18 mg, 0.21 mmol) and 3-bromo-1-propanol (20 µL, 0.22 mmol). The resultant mixture was heated at 60° C. overnight and then the solvent was removed in vacuo. The residue given was partitioned between aqueous saturated sodium hydrogencarbonate solution (5 mL) and ethyl acetate (5 mL). The phases were separated and the aqueous layer was further extracted with ethyl acetate (2×5 mL). The combined extracts were dried over $Na_2SO_4$, filtered and concentrated in vacuo to give an oil (64 mg). This was dissolved in dichloromethane (1 mL) and treated with 1H-tetrazole (13 mg, 0.19 mmol) and triphenylphosphine (47 mg, 0.18 mmol). The mixture was cooled in an ice bath and diethyl azodicarboxylate (30 µL, 0.19 mmol) was added. The resultant mixture was stirred overnight at room temperature, then concentrated in vacuo to give a yellow residue (160 mg). Chromatography on silica gel (7.6 g) eluting with a gradient of dichloromethane:ethanol: 0.88 ammonia (200:8:1 to 100:8:1) gave a yellow solid (14 mg) which was further purified by reversed phase preparative HPLC (condition 1) to give the title compound as a white solid (2 mg, 3%).

NMR (CD$_3$OD, selected data): 0.8 (d, 3H), 1.4 (s, 3H), 1.7 (m, 1H), 2.1–2.3 (m, 3H), 2.35–2.5 (m, 4H), 2.65 (m, 2H), 2.85 (m, 1H), 7.35 (d, 1H), 7.4 (t, 1H), 7.6 (d, 1H), 7.8 (s, 1H), 8.15 (s, 1H), 8.7 (s, 1H).

MS (thermospray): M/Z (MH$^+$) 367.4; $C_{19}H_{26}N_8$+H requires 367.2.

Example 7
1-(2-(1-Perhydroazepinyl)ethyl)-3,4-dimethyl-4-(3-(1H-1,2,3-triazol-4-yl)phenyl)piperidine A solution of 1-(2-chloroethyl)perhydroazepine hydrochloride (42 mg, 0.21 mmol) in N,N-dimethylformamide (1 mL) was treated with triethylamine (30 µL, 0.22 mmol) then transferred to a flask containing 3,4-dimethyl-4-(3-(1H-1,2,3-triazol-4-yl)phenyl)piperidine (Preparation 44, 45 mg, 0.176 mmol) in N,N-dimethylformamide (2 mL). Sodium iodide (32 mg, 0.21 mmol) and sodium hydrogencarbonate (18 mg, 0.21 mmol) were added and the resultant mixture was heated at 60° C. overnight. The solvent was then removed in vacuo and the residue was partitioned between saturated aqueous sodium hydrogencarbonate solution (5 mL) and dichloromethane (5 mL). The phases were separated and the aqueous layer was further extracted with dichloromethane (2×5 mL). The combined extracts were dried over $Na_2SO_4$, filtered and concentrated in vacuo. The residue was purified by reversed phase preparative HPLC (condition 2) to give the acetate salt of the title compound. The free base was obtained by treating with dilute aqueous ammonia solution (2 mL) and extracting with ether (4×3 mL). Drying over $Na_2SO_4$, filtering and evaporation to dryness gave the title compound as a white solid (16 mg, 24%).

NMR (CDCl$_3$, selected data for the free base): 0.8 (d, 3H), 1.35 (s, 3H), 1.6–1.8 (m, 9H), 2.10 (m, 1H), 2.4–2.5 (m, 2H), 2.6–3.0 (m, 11H), 7.25 (d, 1H), 7.35 (t, 1H), 7.55 (d, 1H), 7.85 (s, 1H), 7.95 (s, 1H).

MS (thermospray): M/Z (MH$^+$) 382.6; $C_{23}H_{35}N_5$+H requires 382.3.

Example 8
3,4-Dimethyl-1-(2-(1-piperidino)ethyl)-4-(3-(1H-1,2,3-triazol-4-yl)phenyl)piperidine The title compound was prepared by the method of Example 7 substituting 1-(2-chloroethyl)perhydroazepine hydrochloride with 1-(2-chloroethyl)piperidine hydrochloride (39 mg, 0.21 mmol) to give a white solid (22 mg, 34%).

NMR (CDCl$_3$, selected data for the free base): 0.8 (d, 3H), 1.35 (s, 3H), 1.45–1.55 (m, 2H), 1.65–1.75 (m, 5H), 2.10 (m, 1H), 2.35–2.8 (m, 12H), 2.95 (m, 1H), 7.25 (d, 1H), 7.35 (t, 1H), 7.55 (d, 1H), 7.85 (s, 1H), 7.9 (s, 1H).

MS (thermospray): M/Z (MH$^+$) 368.6; $C_{22}H_{33}N_5$+H requires 368.3.

Example 9
3,4-Dimethyl-1-(3-(1-piperidino)propyl)-4-(3-(1H-1,2,3-triazol-4-yl)phenyl)piperidine The title compound was prepared by the method of Example 7 substituting 1-(2-chloroethyl)perhydroazepine hydrochloride with 1-(3-chloropropyl)piperidine hydrochloride (42 mg, 0.21 mmol) to give a white solid (25 mg, 37%).

NMR (CDCl$_3$, selected data for the free base): 0.75 (d, 3H), 1.35 (s, 3H), 1.45–1.55 (m, 2H), 1.65–1.75 (m, 5H), 1.8–1.9 (m, 2H), 2.05 (m, 1H), 2.3–2.7 (m, 12H), 2.9 (m, 1H), 7.25 (d, 1H), 7.35 (t, 1H), 7.55 (d, 1H), 7.8 (s, 1H), 7.9 (s, 1H).

MS (thermospray): M/Z (MH$^+$) 382.6; $C_{23}H_{35}N_5$+H requires 382.3.

Example 10
1-(6-Hexanenitrile)-3,4-dimethyl-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 45 mg, 0.176 mmol) in N,N-dimethylformamide (4 mL) was added aqueous sodium hydrogencarbonate (18 mg, 0.21 mmol) and 6-bromohexanenitrile (30 µL, 0.23 mmol). The resultant mixture was heated at 60° C. overnight and then the solvent was removed in vacuo. The residue given was partitioned between saturated sodium hydrogencarbonate solution (5 mL) and ethyl acetate (5 mL). The phases were separated and the aqueous layer was further extracted with ethyl acetate (2×5 mL). The combined extracts were dried over $Na_2SO_4$, filtered and concentrated in vacuo. The residue was purified by reversed phase preparative HPLC (condition 1) to give the acetate salt of the title compound. The free base was obtained by treating with dilute aqueous ammonia solution (2 mL) and extracting with ether (4×3 mL). Drying over $Na_2SO_4$, filtering and evaporation to dryness gave the title compound as a white solid (28 mg, 45%).

NMR ($CDCl_3$, selected data for the free base): 0.8 (d, 3H), 1.4 (s, 3H), 1.45–1.55 (m, 2H), 1.6–1.8 (m, 5H), 2.1–2.2 (m, 1H), 2.3–2.75 (m, 8H), 2.95–3.05 (m, 1H), 7.3 (d, 1H), 7.4 (t, 1H), 7.55 (d, 1H), 7.85 (s, 1H), 7.95 (s, 1H).

MS (thermospray): M/Z ($MH^+$) 352.4; $C_{21}H_{29}N_5$+H requires 352.3.

Example 11

1-(5-Pentanenitrile)-3,4-dimethyl-4-(3-(1H-1,2,3-triazol-4-yl)phenyl)piperidine

The title compound was prepared by the method of Example 10 substituting 6-bromohexanenitrile with 5-bromopentanenitrile (25 µL, 0.21 mmol) to give a white solid (22 mg, 37%).

NMR ($CDCl_3$, selected data for the free base): 0.8 (d, 3H), 1.4 (s, 3H), 1.65–1.8 (m, 5H), 2.1–2.2 (m, 1H), 2.3–2.75 (m, 8H), 2.9–3.05 (m, 1H), 7.3 (d, 1H), 7.4 (t, 1H), 7.6 (d, 1H), 7.8 (s, 1H), 7.95 (s, 1H).

MS (thermospray): M/Z ($MH^+$) 338.4; $C_{20}H_{27}N_5$+H requires 338.2.

Example 12

1-(2-(4-Fluorophenyl)ethyl)-3,4-dimethyl-4-(3-(1H-1,2,3-triazol-4-yl)phenyl)piperidine The title compound was prepared by the method of Example 10 substituting 6-bromohexanenitrile with 1-(2-bromoethyl)-4-fluorobenzene (Reference 1, 45 mg, 0.22 mmol) to give a white solid (24 mg, 36%).

NMR ($CDCl_3$, selected data for the free base): 0.8 (d, 3H), 1.4 (s, 3H), 1.7–1.85 (m, 1H), 2.1–2.2 (m, 1H), 2.45–3.1 (m, 9H), 6.95 (t, 2H), 7.15–7.25 (m, 2H), 7.3 (d, 1H), 7.4 (t, 1H), 7.6 (d, 1H), 7.85 (s, 1H), 7.95 (s, 1H).

MS (thermospray): M/Z ($MH^+$) 379.4; $C_{23}H_{27}FN_4$+H requires 379.2.

Example 13

3,4-Dimethyl-1-(2-phenylethyl)-4-(3-(1H-1,2,3-triazol-4-yl)phenyl)piperidine

The title compound was prepared by the method of Example 10 substituting 6-bromohexanenitrile with (2-bromoethyl)benzene (30 µL, 0.22 mmol) to give a white solid (32 mg, 50%).

NMR ($CDCl_3$, selected data for the free base): 0.85 (d, 3H), 1.4 (s, 3H), 1.75 (m, 1H), 2.15 (m, 1H), 2.5–3.15 (m, 9H), 7.15–7.35 (m, 6H), 7.4 (t, 1H), 7.6 (d, 1H), 7.85 (s, 1H), 7.95 (s, 1H).

MS (thermospray): M/Z ($MH^+$) 361.4; $C_{23}H_{28}N_4$+H requires 361.2.

Example 14

1-(5-Methoxycarbonylpentyl)-3,4-dimethyl-4-(3-(1H-1,2,3-triazol-4-yl)phenyl)piperidine The title compound was prepared by the method of Example 10 substituting 6-bromohexanenitrile with methyl 6-bromohexanoate (Preparation 13, 44 mg, 0.21 mmol) to give a colourless gum (18 mg, 27%).

NMR ($CDCl_3$, selected data for the free base): 0.8 (d, 3H), 1.3–1.45 (m, 5H), 1.55–1.85 (m, 5H), 2.1 (m, 1H), 2.25–2.8 (m, 8H), 3.0 (m, 1H), 3.65 (s, 3H), 7.3 (d, 1H), 7.35 (t, 1H), 7.55 (d, 1H), 7.85 (s, 1H), 7.95 15 (s, 1H).

MS (thermospray): M/Z ($MH^+$) 385.3; $C_{22}H_{32}N_4O_2$+H requires 385.3.

Example 15

1-(4-Methoxybutyl)-3,4-dimethyl-4-(3-(1H-1,2,3-triazol-4-yl)phenyl)piperidine

To a solution of 3,4-dimethyl-4-(3-(1H-1,2,3-triazol-4-yl)phenyl)piperidine (Preparation 44, 50 mg, 0.19 mmol) in N,N-dimethylformamide (2 mL) was added sodium hydrogencarbonate (25 mg, 0.29 mmol) and 1-iodo-4-methoxybutane (Preparation 15, 50 mg, 0.23 mmol). The resultant mixture was heated at 60° C. overnight and then cooled to room temperature. The residue given was partitioned between saturated aqueous sodium hydrogencarbonate solution (25 mL) and ether (15 mL). The phases were separated and the aqueous layer was further extracted with ether (2×15 mL). The combined extracts were dried over $MgSO_4$, filtered and concentrated in vacuo. The residue was purified by chromatography eluting with a gradient of $CH_2Cl_2$:MeOH:0.88 ammonia (100:8:1) to give the title compound as a colourless oil (15 mg, 22%).

NMR ($CDCl_3$, selected data for the free base): 0.9 (d, 3H), 1.4 (s, 3H), 3.3 (s, 3H), 7.2 (d, 1H), 7.4 (t, 1H), 7.6 (d, 1H), 7.8 (s, 1H), 7.9 (s, 1H).

MS (thermospray): M/Z ($MH^+$) 343.5; $C_{20}H_{30}N_4O$+H requires 343.2.

Example 16

1-(3-Ethoxypropyl)-3,4-dimethyl-4-(3-(1H-1,2,3-triazol-4-yl)phenyl)piperidine

The title compound was prepared by the method of Example 15 substituting 1-iodo-4-methoxybutane with 1-ethoxy-3-iodopropane (Preparation 17, 50 mg, 0.23 mmol) to give the title compound as a colourless oil (21 mg, 31%).

NMR ($CDCl_3$, selected data for the free base): 0.8 (d, 3H), 1.2 (t, 3H), 1.4 (s, 3H), 3.4–3.6 (m, 4H), 7.3 (d, 1H), 7.4 (t, 1H), .7.6 (d, 1H), 7.8 (s, 1H), 7.9 (s, 1H).

MS (thermospray) (HCl salt): M/Z ($MH^+$) 343.3; $C_{20}H_{30}N_4O$+H requires 343.2.

Example 17

3,4-Dimethyl-1-(2-propoxyethyl)-4-(3-(1H-1,2,3-triazol-4-yl)phenyl)piperidine

The title compound was prepared by the method of Example 15 substituting 1-iodo-4-methoxybutane with 1-(2-iodoethoxy)propane (Preparation 19, 50 mg, 0.23 mmol) to give the title compound as a colourless oil (30 mg, 45%).

NMR ($CDCl_3$, selected data for the free base) 0.8 (d, 3H), 0.9 (t, 3H), 1.4 (s, 3H), 3.4 (t, 2H), 3.6 (t, 2H), 7.3 (m, 2H), 7.5 (d, 2H), 7.8 (s, 1H), 8.0 (s, 1H).

MS (thermospray) (HCl salt): M/Z ($MH^+$) 343.3; $C_{20}H_{30}N_4O$+H requires 343.2.

Example 18

1-(1-Ethoxycarbonylmethyl)-3,4-dimethyl-4-(3-(1H-1,2,3-triazol-4-yl)phenyl)piperidine The title compound was prepared by the method of Example 15 substituting 1-iodo-4-methoxybutane with commercially available ethyl 2-iodoacetate (50 mg, 0.23 mmol) to give the title compound as a colourless oil (27 mg, 40%).

NMR ($CDCl_3$, selected data for the free base): 0.8 (d, 3H), 1.3 (t, 3H), 1.4 (s, 3H), 4.2 (m, 2H), 7.3 (d, 1H), 7.3 (t, 1H), 7.6 (d, 1H), 7.8 (s, 1H), 8.0 (s, 1H).

MS (thermospray): M/Z ($MH^+$) 343.5; $C19H_{26}N_4O_2$+H requires 343.2.

Example 19
1-(1N,N-Diethyl-3-propanamido)-3,4-dimethyl-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 50 mg, 0.19 mmol) in tetrahydrofuran (5 mL) was added N,N-diethylacrylamide (Preparation 20, 30 mg, 0.23 mmol). The resultant mixture was heated at 60° C., cooled and then partitioned between water (10 mL) and ether (15 mL). The phases were separated and the aqueous layer was further extracted with ether (2×15 mL). The combined extracts were dried over $MgSO_4$, filtered and concentrated in vacuo. The residue was purified by chromatography eluting with a gradient of dichloromethane:methanol:0.88 ammonia (100:8:1) to give the title compound as a colourless oil (24 mg, 32%).

NMR ($CDCl_3$, selected data for the free base): 0.8 (d, 3H), 1.1–1.2 (m, 6H), 1.4 (s, 3H), 3.3–3.4 (m, 4H), 7.2 (d, 1H), 7.3 (t, 1H), 7.6 (d, 1H), 7.85 (s, 1H), 7.95 (s, 1H).

MS (thermospray): M/Z ($MH^+$) 384.6; $C_{22}H_{33}N_5O+H$ requires 384.3.

Example 20
1-(N-benzyl-3-propanamido)-3,4-dimethyl-4-(3-(1H-1,2,3-triazol-4-yl)phenyl)piperidine The title compound was prepared by the method of Example 19 substituting N,N-diethylacrylamide with N-benzylacrylamide (Preparation 21, 30 mg, 0.23 mmol) to give the title compound as a colourless oil (29 mg, 36%).

NMR ($CDCl_3$, selected data for the free base): 0.4 (d, 3H), 1.3 (s, 3H), 4.3 (m, 1H), 4.5 (m, 1H), 7.15 (d, 1H), 7.25 (m, 5H), 7.4 (t, 1H), 7.6 (d, 1H), 7.7 (s, 1H), 7.9 (s, 1H), 9.1 (br, 1H).

MS (thermospray): M/Z ($MH^+$) 418.6; $C_{25}H_{31}N_5O+H$ requires 418.3.

Example 21
3,4-Dimethyl-1-(N-propyl-3-propanamido)-4-(3-(1H-1,2,3-triazol-4-yl)phenyl)piperidine The title compound was prepared by the method of Example 19 substituting N,N-diethylacrylamide with N-propylacrylamide (Preparation 22, 30 mg, 0.23 mmol) to give the title compound as a colourless oil (24 mg, 34%).

NMR ($CDCl_3$, selected data for the free base): 0.7 (d, 3H), 1.4 (s, 3H), 7.3 (d, 1H), 7.4 (t, 1H), 7.6 (d, 1H), 7.8 (s, 1H), 8.0 (s, 1H), 8.5 (br, 1H).

MS (thermospray): M/Z ($MH^+$) 370.0; $C_{21}H_{31}N_5O+H$ requires 370.2.

Example 22
1-(2-Ethanesulfonamidoethyl)-3,4-dimethyl-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 50 mg, 0.19 mmol) in N,N-dimethylformamide (2 mL) was added sodium hydrogencarbonate (25 mg, 0.29 mmol) and N-(2-iodoethyl)-1-ethanesulfonamide (Preparation 24, 60 mg, 0.23 mmol). The resultant mixture was heated at 60° C. overnight and then cooled to room temperature. The residue given was partitioned between saturated aqueous sodium hydrogencarbonate solution (25 mL) and ether (15 mL). The phases were separated and the aqueous layer was further extracted with ether (2×15 mL). The combined extracts were dried over $MgSO_4$, filtered and concentrated in vacuo. The residue was purified by chromatography on silica gel eluting with a gradient of $CH_2Cl_2$:MeOH:0.88 ammonia (100:8:1) to give the title compound as a colourless oil (28 mg, 38%).

NMR ($CDCl_3$, selected data for the free base): 0.8 (d, 3H), 1.3 (s, 3H), 1.4 (m, 3H), 3.1 (m, 2H), 7.3 (d, 1H), 7.4 (t, 1H), 7.6 (d, 1H), 7.8 (s, 1H), 8.0 (s, 1H).

MS (thermospray) (HCl salt): M/Z ($MH^+$) 392.2; $C_{19}H_{29}N_5O_2S+H$ requires 392.2.

Example 23
3,4-Dimethyl-1-(2-phenoxyethyl)-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 50 mg, 0.20 mmol) in N,N-dimethylformamide (6 mL) was added commercially available 2-(bromoethoxy)benzene (43 mg, 0.22 mmol) and sodium hydrogencarbonate (48 mg, 0.56 mmol). The resultant mixture was heated to 80° C. and stirred overnight. The reaction mixture was cooled, poured onto saturated aqueous sodium hydrogencarbonate solution (100 mL) and extracted with ethyl acetate (3×20 mL). The combined extracts were dried over $MgSO_4$, filtered and concentrated in vacuo to give an off-white gum. The crude product was partially purified by chromatography on a 5 g silica Waters Sep-Pak3 eluting with dichloromethane and then 5% methanol in dichloromethane. The pure fractions were collected to give the title compound as a clear oil as a clear gum (10 mg, 13.6%).

NMR ($CD_3OD$, free base): 0.85 (m, 3H), 1.25 (m, 1H), 1.4 (s, 3H), 1.75 (m, 1H), 2.2 (m, 1H), 2.45 (m, 1H), 2.65 (m, 1H), 2.7–3.0 (m, 5H), 4.1–4.2 (d, 2H), 6.9–7.0 (m, 3H), 7.2–7.4 (m, 4H), 7.6 (m, 1H), 7.8 (s, 1H), 8.1 (s, 1H).

MS (thermospray): M/Z ($MH^+$) 377.2; $C_{23}H_{28}N_4O+H$ requires 377.2.

Example 24
3,4-Dimethyl-1-(3-phenylpropyl)-4-(3-(1H-1,2,3-triazol-4-yl)phenyl)piperidine The title compound was prepared by the method of Example 23 substituting 2-(bromoethoxy)benzene with commercially available 1-bromo-3-phenylpropane (33 µL, 0.22 mmol) to give a white gum (10 mg, 13.6%).

NMR ($CD_3OD$, free base): 0.8 (d, 3H), 1.3 (m, 1H), 1.4 (s, 3H), 1.7–1.9 (m, 3H), 2.15 (m, 1H), 2.3–2.5 (m, 3H), 2.6–2.8 (m, 4H), 2.9 (m, 1H), 7.1–7.3 (m, 6H), 7.3–7.4 (m, 2H), 7.6 (d, 1H), 7.8 (s, 1H), 8.1 (s, 1H).

MS (thermospray): M/Z ($MH^+$) 375.3; $C_{24}H_{30}N_4+H$ requires 375.3.

Example 25
1-(2-Butoxyethyl)-3,4-dimethyl-4-(3-(1H-1,2,3-triazol-4-yl)phenyl)piperidine The title compound was prepared by the method of Example 23 substituting 2-(bromoethoxy)benzene with commercially available 1-(2-bromoethoxy)butane (33 mg, 0.20 mmol) to give a white gum (13 mg, 19.0%).

NMR ($CD_3OD$, free base): 0.8 (d, 3H), 0.95 (t, 3H), 1.2–1.5 (m, 4H), 1.5–1.6 (m, 2H), 1.75 (m, 1H), 2.1–2.2 (m, 1H), 2.4 (m, 1H), 2.5–2.8 (m, 5H), 2.9 (m, 1H), 3.3 (m, 1H), 3.4–3.5 (m, 2H), 3.6 (m, 2H), 7.3–7.4 (m, 2H), 7.6 (d, 1H), 7.8 (s, 11H), 8.1 (s, 1H).

MS (thermospray): M/Z ($MH^+$) 357.2; $C_{21}H_{32}N_4O+H$ requires 357.3.

Example 26
3,4-Dimethyl-1-(3-phenoxypropyl)-4-(3-(1H-1,2,3-triazol-4-yl)phenyl)piperidine The title compound was prepared by the method of Example 23 substituting 2-(bromoethoxy)benzene with commercially available 3-phenoxypropyl bromide (42 mg, 0.20 mmol) to give a white gum (14 mg, 18.4%).

NMR ($CD_3OD$, free base): 0.8 (d, 3H), 1.4 (s, 3H), 1.75 (m, 1H), 1.9–2.1 (m, 2H), 2.15 (m, 1H), 2.4 (m, 1H), 2.5–2.7 (m, 5H), 2.95 (m, 1H), 4.05 (m, 2H), 6.85 (d, 3H), 7.2–7.3 (m, 2H), 7.3–7.4 (m, 2H), 7.6 (d, 1H), 7.8 (s, 1H), 8.1 (s, 1H).

MS (thermospray): M/Z (MH$^+$) 391.2; $C_{24}H_{30}N_4O$+H requires 391.3.

Example 27

1-(2-(Benzyloxy)ethyl)-3,4-dimethyl-4-(3-(1H-1,2,3-triazol-4-yl)phenyl)piperidine The title compound was prepared by the method of Example 23 substituting 2-(bromoethoxy)benzene with 1-((2-bromoethoxy)methyl) benzene (Reference 2, 42 mg, 0.20 mmol) to give a white gum (10 mg, 13.1%).

NMR (CD$_3$OD, free base): 0.8 (m, 3H), 1.3 (m, 1H), 1.4 (s, 3H), 1.6–1.8 (m, 1H), 2.15 (m, 1H), 2.4 (m, 1H), 2.5–2.8 (m, 5H), 2.9 (m, 1H), 3.6–3.7 (m, 2H), 4.5 (s, 2H), 7.2–7.4 (m, 6H), 7.6 (m, 1H), 7.8 (s, 1H), 8.1 (s, 1H).

Example 28

3,4-Dimethyl-1-(2-(3-methylphenyl)ethyl)-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 80 mg, 0.31 mmol) in N,N-dimethyl-formamide (6 mL) was added 1-(2-bromoethyl)-3-methylbenzene (Preparation 46, 67 mg, 0.31 mmol) and sodium hydrogencarbonate (40 mg, 0.47 mmol). The resultant mixture was heated to 80° C. and stirred overnight. The reaction mixture was cooled, poured onto saturated aqueous sodium hydrogencarbonate solution (100 mL) and extracted with ethyl acetate (3×20 mL). The combined extracts were dried over MgSO$_4$, filtered and concentrated in vacuo to give an off-white gum. The crude product was partially purified by column chromatography on a 5 g silica Waters Sep-Pak3 eluting with dichloromethane and then 5% methanol in dichloromethane. The pure fractions were collected to give the title compound as a clear oil (15 mg, 12.8%).

NMR (CD$_3$OD, free base): 0.85 (d, 3H), 1.4 (s, 3H), 1.75 (m, 1H), 2.15 (m, 1H), 2.3 (s, 3H), 2.4 (m, 1H), 2.5–2.7 (m, 2H), 2.7–2.9 (m, 5H), 2.95 (m, 1H), 6.9–7.1 (m, 3H), 7.15 (t, 1H), 7.3–7.4 (m, 2H), 7.6 (d, 1H), 7.8 (s, 1H), 8.1 (s, 1H).

MS (thermospray): M/Z (MH$^+$) 375.2; $C_{24}H_{30}N_4$+H requires 375.3.

Example 29

3,4-Dimethyl-1-pentyl-4-(3-(1H-1,2,3-triazol-4-yl)phenyl)piperidine

To a solution of 3,4-dimethyl-4-(3-(1H-1,2,3-triazol-4-yl)phenyl)piperidine (Preparation 44, 45 mg, 0.18 mmol) in N,N-dimethylformamide (5 mL) was added commercially available bromopentane (29 mg, 0.19 mmol) and sodium hydrogencarbonate (30 mg, 0.35 mmol). The resultant mixture was heated to 80° C. and stirred overnight. The reaction mixture was cooled, poured onto saturated aqueous sodium hydrogen-carbonate solution (100 mL) and extracted with ethyl acetate (3×20 mL). The combined extracts were dried over MgSO$_4$, filtered and concentrated in vacuo to give an off-white gum. The crude product was purified by reverse phase high performance liquid chromatography (condition 1) to give the title compound as a clear oil (33 mg, 57.3%).

NMR (CD$_3$OD, acetate salt): 0.8–1.0 (m, 6H), 1.3–1.4 (m, 4H), 1.4 (s, 3H), 1.6–1.8 (m, 2H), 2.4 (m, 1H), 2.55 (m, 1H), 2.95–3.05 (m, 2H), 3.15–3.25 (m, 2H), 3.25–3.3 (m, 2H), 3.4 (m, 1H), 7.35 (d, 1H), 7.45 (t, 1H), 7.6 (d, 1H), 7.8 (s, 1H), 8.1 (s, 1H).

MS (thermospray): M/Z (MH$^+$) 327.3; $C_{20}H_{30}N_4$+H requires 327.3.

Example 30

1-Butyl-3,4-dimethyl-4-(3-(1H-1,2,3-triazol-4-yl)phenyl)piperidine

The title compound was prepared by the method of Example 29 substituting bromopentane with commercially available bromobutane (26 mg, 0.19 mmol) to give a clear gum (14 mg, 25.4%).

NMR (CD$_3$OD, acetate salt): 0.8 (d, 3H), 1.0 (t, 3H), 1.3–1.4 (m, 2H), 1.4–1.5 (s, 3H), 1.6–1.8 (m, 2H), 2.35 (m, 1H), 2.5 (m, 1H), 2.8–2.9 (m 2H), 3.0–3.2 (m, 3H), 3.4 (m, 2H), 7.3–7.4 (m, 2H), 7.6 (d, 1H), 7.8 (s 1H), 8.1 (s, 1H).

MS (thermospray): M/Z (MH$^+$) 313.3; $C_{19}H_{28}N_4$+H requires 313.2.

Example 31

1-(2-(1,3-Dioxan-2-yl)ethyl)-3,4-dimethyl-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 45 mg, 0.18 mmol) in N,N-dimethylformamide (5 mL) was added commercially available 2-(2-bromoethyl)-1,3-dioxane (38 mg, 0.19 mmol) and sodium hydrogencarbonate (30 mg, 0.35 mmol). The resultant mixture was heated to 80° C. and stirred overnight. The reaction mixture was cooled, poured onto saturated aqueous sodium hydrogencarbonate solution (100 mL) and extracted with ethyl acetate (3×20 mL). The combined extracts were dried over MgSO$_4$, filtered and concentrated in vacuo to give an off-white gum. The crude product was purified by reverse phase high performance liquid chromatography (condition 1) to give the acetate salt as a clear gum. This was treated with aqueous 2 M potassium carbonate solution (20 mL) and extracted with dichloromethane (3×5 mL). The combined extracts were dried over Na$_2$SO$_4$, filtered and evaporated to dryness. The hydrochloride salt of the title product was prepared and obtained as a white gum (9 mg, 13.8%).

NMR (CD$_3$OD, HCl salt): 0.8 (d, 3H), 1.4 (s, 3H), 1.7–1.8 (m, 3H), 2.0 (m, 1H), 2.15 (m, 1H), 2.3–2.6 (m, 4H), 2.6–2.65 (m, 2H), 2.95 (m, 1H), 3.3–3.35 (m, 2H), 3.7–3.9 (m, 2H), 4.0–4.1 (m, 2H), 4.65 (m, 1H), 7.3–7.4 (m, 2H), 7.65 (d, 1H), 7.8 (s, 1H), 8.1 (s, 1H).

MS (thermospray): M/Z (MH$^+$) 371.2; $C_{21}H_{30}N_4O_2$+H requires 371.2.

Example 32

1-(3-(2,5-Dimethoxyphenoxy)propyl)-3,4-dimethyl-4-(3-(1H-1,2,3-triazol-4-yl)phenyl)piperidine The title compound was prepared by the method of Example 31 substituting 2-(2-bromoethyl)-1,3-dioxane with 1-bromo-3-(2,5-dimethoxyphenoxy)propane (Reference 3, 53 mg, 0.19 mmol) to give a clear gum (11 mg, 13.9%).

NMR (CD$_3$OD, selected data HCl salt): 0.8 (m, 3H), 1.3 (s, 3H), 2.0–2.2 (m, 1H), 2.2–2.4 (m, 2H), 2.5–2.7 (m, 2H), 3.7 (s, 3H), 3.8 (s, 3H), 6.45 (d, 1H), 6.6 (s, 1H), 6.85 (d, 1H), 7.35 (m, 1H), 7.55 (m, 1H), 7.75 (d, 1H), 7.8 (s, 1H), 8.3 (s, 1H).

MS (thermospray): M/Z (MH$^+$) 451.2; $C_{26}H_{34}N_4O_3$+H requires 451.3.

Example 33

1-(2-(2-methoxyethoxy)ethyl)-3,4-dimethyl-4-(3-(1H-1,2,3-triazol-4-yl)phenyl)piperidine The title compound was prepared by the method of Example 31 substituting 2-(2-bromoethyl)-1,3-dioxane with commercially available 1-bromo-2-(2-methoxyethoxy)ethane (35 mg, 0.19 mmol) to give a clear gum (12 mg, 19%).

MS (thermospray): M/Z (MH$^+$) 359.1; $C_{20}H_{30}N_4O_2$+H requires 359.2.

Example 34
3,4-Dimethyl-1-(3-tetrahydro-3-furanylpropyl)-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 45 mg, 0.18 mmol) in N,N-dimethylformamide (5 mL) was added 3-(tetrahydro-3-furanyl)propionic acid (Preparation 47, 28 mg, 0.19 mmol), 1-(3-dimethylaminopropyl)-3-ethylcarbodiimide hydrochloride (44 mg, 0.23 mmol) and 1-hydroxybenzotriazole hydrate (24 mg, 0.18 mmol). The resultant mixture was heated to 80° C. and stirred overnight. The reaction mixture was cooled, poured onto saturated aqueous sodium hydrogencarbonate solution (100 mL) and extracted with ethyl acetate (3×20 mL). The combined organics were dried over $MgSO_4$ and concentrated in vacuo to give an off-white gum. The product was dissolved in tetrahydrofuran (2 mL) and cooled to 0° C. The solution was treated dropwise with lithium aluminium hydride (1.0 M solution in THF, 0.35 mL, 0.35 mmol). The reaction was allowed to warm to room temperature and stirred overnight. The reaction mixture was treated with saturated ammonium chloride solution and the product extracted with ethyl acetate (3×10 mL). The combined organics were dried over $Na_2SO_4$ and the solvent removed in vacuo to give a white gum. The crude product was purified by reverse-phase high performance liquid chromatography (condition 1) to give the title compound as a clear oil (17 mg, 26%).

NMR ($CD_3OD$, selected data for the acetate salt): 0.9 (d, 3H), 1.3 (s, 3H), 1.5–1.6 (m, 3H), 1.7–1.8 (m, 2H), 2.15 (m, 1H), 2.25 (m, 1H), 2.4 (m, 1H), 2.55 (m, 1H), 3.0 (m, 2H), 3.1–3.2 (m, 2H), 3.3–3.4 (m, 3H), 3.75 (m, 1H), 3.8–4.0 (m, 2H), 7.3–7.4 (m, 2H), 7.6 (d, 1H), 7.8 (s, 1H), 8.1 (s, 1H).

MS (thermospray): M/Z ($MH^+$) 369.3; $C_{22}H_{32}N_4O+H$ requires 369.3.

Example 35
3,4-Dimethyl-1-(3-tetrahydro-2H-pyran-2-ylpropyl)-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 45 mg, 0.18 mmol) in N,N-dimethylformamide (5 mL) was added 3-(tetrahydro-2H-pyran-2-yl)propionic acid (Preparation 53, 31 mg, 0.20 mmol), 1-(3-dimethylaminopropyl)-3-ethylcarbodiimide hydrochloride (44 mg, 0.23 mmol) and 1-hydroxybenzotriazole hydrate (24 mg, 0.18 mmol). The resultant mixture was heated to 80° C. and stirred overnight. The reaction mixture was cooled, poured onto saturated aqueous sodium hydrogencarbonate solution and extracted with ethyl acetate (3×20 mL). The combined organics were dried over $MgSO_4$ and concentrated in vacuo to give an off-white gum. The product was dissolved in tetrahydrofuran (2 mL) and cooled to 0° C. The solution was treated dropwise with lithium aluminium hydride (1.0 M solution in THF, 0.24 mL, 0.24 mmol). The reaction was allowed to warm to room temperature and stirred overnight. The reaction mixture was treated with saturated aqueous ammonium chloride solution and the product extracted with ethyl acetate (3×10 mL). The combined organics were dried over $Na_2SO_4$ and the solvent removed in vacuo to give a white gum. The crude product was purified by reverse-phase high performance liquid chromatography (condition 1) to give an acetate salt, which was obtained as a brown gum. This gum was dissolved in dichloromethane (50 mL) and washed with saturated aqueous sodium carbonate (50 mL). The organic layer was then separated, dried ($Na_2SO_4$) and concentrated in vacuo to give the title compound as a clear oil (30 mg, 44.6%).

NMR ($CDCl_3$, free base): 0.8 (m, 3H), 0.95 (m, 1H), 1.3 (s, 3H), 1.3–1.8 (m, 7H), 3.0 (m, 1H), 3.25 (m, 1H), 3.45 (m, 1H), 3.95 (m, 1H), 7.3 (d, 1H), 7.5 (t, 1H), 7.7 (d, 1H), 7.8 (s, 1H), 8.1 (s, 1H).

MS (thermospray): M/Z ($MH^+$) 383.3; $C_{23}H_{34}N_4O+H$ requires 383.3.

Example 36
1-(3-Hydroxy-3-phenylpropyl)-3,4-dimethyl-4-(3-(1H-1,2,3-triazol-4-yl)phenyl)piperidine To a solution of 3,4-dimethyl-4-(3-(1H-1,2,3-triazol-4-yl)phenyl)piperidine (Preparation 44, 50 mg, 0.20 mmol) in N,N-dimethylformamide (6 mL) was added commercially available 3-chloro-1-phenyl-1-propanol (33 mg, 0.21 mmol), sodium iodide (15 mg) and aqueous sodium hydrogencarbonate (25 mg, 0.29 mmol). The resultant mixture was heated to 80° C. and stirred overnight. The reaction mixture was cooled, poured onto saturated aqueous sodium hydrogencarbonate solution (100 mL) and extracted with ethyl acetate (3×20 mL). The combined extracts were dried over $MgSO_4$, filtered and concentrated in vacuo to give an off-white gum. The crude product was purified by column chromatography on a 5 g silica Waters Sep-Pak3 eluting with dichloromethane and then dichloromethane:methanol (5:95) to give the title compound as a clear oil (19 mg, 25%).

NMR ($CDCl_3$, selected data of the free base, as a mixture of diastereomers): 0.8–0.9 (m, 3H), 1.4 (s, 3H), 1.75–2.1 (m, 3H), 2.15 (m, 1H), 2.5–2.9 (m, 6H), 3.1–3.3 (m, 1H), 4.9–5.1 (m, 1H), 7.2–7.5 (m, 7H), 7.6 (d, 1H), 7.7 (s, 1H), 7.9 (s, 1H).

MS (thermospray): M/Z ($MH^+$) 391.0; $C_{24}H_{30}N_4O+H$ requires 391.2.

Example 37
1-Benzyl-4-methyl-4-(3-(5-(trimethylsilyl)-1H-1,2,3-triazol-4-yl)phenyl)piperidine To a solution of (trimethylsilyl)diazomethane (2.0 M in hexane, 0.55 mL, 1.10 mmol) in tetrahydrofuran (5 mL) at 0° C. under an atmosphere of nitrogen was added n-butyllithium (1.6 M in hexane, 0.69 mL, 1.10 mmol) dropwise. After 1 h, a solution of 1-benzyl-4-(3-cyanophenyl)-4-methylpiperidine (Preparation 9, 300 mg, 1.03 mmol) in tetrahydrofuran (10 mL) was added such that the internal temperature remained at 0° C. After 4.5 h, the reaction was quenched with saturated sodium hydrogencarbonate (25 mL) and the mixture was extracted with diethyl ether (3×25 mL). The extracts were washed with water (10 mL) and brine (10 mL), dried over $Na_2SO_4$, filtered and concentrated in vacuo to give the title compound as a foam (360 mg, 86%).

NMR ($CDCl_3$, selected data for the free base): 0.35 (m, 9H), 1.25 (m, 3H), 1.8 (m, 2H), 2.15 (m, 2H), 2.4–2.6 (m, 4H), 7.2–7.6 (m, 9H).

MS (thermospray): M/Z ($MH^+$) 405.0; $C_{24}H_{32}N_4Si+H$ requires 405.2.

Example 38
1-Benzyl-4-methyl-4-(3-(1H-1,2,3-triazol-4-yl)phenyl)piperidine

A solution of 1-benzyl-4-methyl-4-(3-(5-(trimethylsilyl)-1H-1,2,3-triazol-4-yl)phenyl)piperidine (Example 37, assume 1.03 mmol) in 2 N hydrochloric acid:methanol (1:1, 20 mL) was heated at 90° C. overnight. After allowing to cool, the reaction mixture was adjusted to pH 9 using aqueous 2 N sodium hydroxide. The aqueous mixture was extracted with ethyl acetate (3×20 mL) and the extracts were dried over $Na_2SO_4$, filtered and concentrated in vacuo. The residue was purified by silica column chromatography eluting with a gradient of ethyl acetate:hexane:0.88 ammonia (50:50:1 to 100:0:1) to give the title compound as a white solid (320 mg, 94%).

NMR (CDCl$_3$, selected data for the free base): 1.25 (m, 3H), 1.8 (m, 2H), 2.2 (m, 2H), 2.4–2.6 (m, 4H), 7.2–7.4 (m, 7H), 7.6–8.0 (m, 3H).

MS (thermospray): M/Z (MH$^+$) 333.2; C$_{21}$H$_{24}$N$_4$+H requires 333.2.

Example 39
1-Benzyl-4-methyl-4-(3-(1H-1,2,4-triazol-3-yl)phenyl)piperidine

To a solution of 1-benzyl-4-(3-(methoxycarbonimidoyl)phenyl)-4-methylpiperidine (Preparation 12, 735 mg, 2.28 mmol) in methanol (10 mL) was added a solution of formic acid hydrazide (274 mg, 4.56 mmol) in methanol (10 mL). The resultant mixture was stirred for 30 min and then concentrated in vacuo. The residual oil was heated at 100° C. for 1 h and then allowed to cool. This was purified on silica gel (50 g) by column chromatography eluting with a gradient of ethyl acetate:hexane:0.88 ammonia (80:20:1 to 90:10:1) to give the title compound as a clear oil (248 mg, 33%).

NMR (CDCl$_3$, selected data for the free base): 1.25 (m, 3H), 1.8 (m, 2H), 2.2 (m, 2H), 2.4–2.6 (m, 4H), 7.2–7.45 (m, 7H), 7.8–8.2 (m, 3H).

MS (thermospray): M/Z (MH$^+$) 333.1; C$_{21}$H$_{24}$N$_4$+H requires 333.2.

Example 40
1-Hexyl-4-methyl-4-(3-(1H-1,2,4-triazol-3-yl)phenyl)piperidine

To a solution of 4-methyl-4-(3-(1H-1,2,4-triazol-3-yl)phenyl)piperidine (Preparation 45, 55 mg, 0.23 mmol) in N,N-dimethylformamide (2 mL) was added sodium hydrogencarbonate (28 mg, 0.34 mmol) and bromohexane (32 µL, 0.23 mmol). The resultant mixture was heated at 50° C. for 2 h and then allowed to cool. The mixture was partitioned between water (5 mL) and dichloromethane (20 mL). The layers were separated, and the aqueous layer was extracted with dichloromethane (20 mL). The combined extracts were dried over Na$_2$SO$_4$, filtered and concentrated in vacuo and the residue was purified by silica (5 g) column chromatography eluting with methanol:dichloromethane:0.88 ammonia (10:90:1) to give the title compound as a clear oil (7 mg, 9%).

NMR (CDCl$_3$, selected data for the free base): 0.85 (m, 3H), 1.25 (m, 3H), 1.85 (m, 2H), 2.2–2.4 (m, 4H), 7.45 (m, 2H), 7.8–8.2 (m, 3H).

MS (thermospray): M/Z (MH$^+$) 327.5; C$_{20}$H$_{30}$N$_4$+H requires 327.3.

Example 41
4-Methyl-1-(3-phenylpropyl)-4-(3-(1H-1,2,4-triazol-3-yl)phenyl)piperidine To a solution of 4-methyl-4-(3-(1H-1,2,4-triazol-3-yl)phenyl)piperidine (Preparation 45, 65 mg, 0.27 mmol) in N,N-dimethylformamide (2 mL) was added sodium hydrogencarbonate (34 mg, 0.40 mmol) and 1-bromo-3-phenylpropane (41 µL, 0.27 mmol). The resultant mixture was heated at 50° C. for 2 h and then allowed to cool. The mixture was partitioned between water (5 mL) and dichloromethane (20 mL). The layers were separated, and the aqueous layer was extracted with dichloromethane (20 mL). The combined extracts were dried over Na$_2$SO$_4$, filtered and concentrated in vacuo and the residue was purified by column chromatography on silica gel (5 g) eluting with MeOH:CH$_2$Cl$_2$:0.88 ammonia (10:90:1) to give the title compound as a clear oil (13 mg, 13%).

NMR (CDCl$_3$, selected data for the free base): 1.25 (m, 3H), 1.8 (m, 4H), 2.2–2.35 (m, 4H), 2.6 (m, 2H), 7.15–7.25 (m, 5H), 7.4 (m, 2H), 7.8–8.2 (m, 3H).

MS (thermospray): M/Z (MH$^+$) 361.4; C$_{23}$H$_{28}$N$_4$+H requires 361.2.

Example 42
1-Benzyl-4-methyl-4-(3-(1H-1,3-imidazol-2-yl)phenyl)piperidine

To a solution of the hydrochloride salt of 1-benzyl-4-(3-(methoxycarbonimidoyl)phenyl)-4-methylpiperidine (Preparation 12, assume 1.72 mmol) in methanol (10 mL) was added aminoacetaldehyde dimethyl acetal (0.197 mL, 1.81 mmol) and the reaction mixture was heated under reflux for 90 min and then allowed to cool. The mixture was concentrated in vacuo, 2 M hydrochloric acid (10 mL) was added and the reaction mixture was heated under reflux for 5 h. The mixture was adjusted to pH 9 with 10 M sodium hydroxide and the basic aqueous layer was extracted with dichloromethane (3×20 mL). The combined extracts were washed with water (10 mL), dried over Na$_2$SO$_4$, filtered and concentrated in vacuo. The residue was purified by column chromatography on silica gel (20 g) eluting with a gradient of ethyl acetate:hexane:0.88 ammonia (80:20:1 to 100:0:1) to give the title compound as a clear oil (43 mg, 8% over two steps). The oil was dissolved in diethyl ether (4 mL) and treated with 1.0 M HCl in ether (150 mL) to afford after removal of the solvent 43 mg of a white solid.

NMR (CDCl$_3$, selected data for the free base): 1.2 (s, 3H), 1.7–1.9 (m, 3H), 2.3–2.55 (m, 4H), 7.1–7.4 (m, 9H), 7.6 (d, 1H), 7.9 (s, 1H).

MS (thermospray): M/Z (MH$^+$) 332.4; C$_{22}$H$_{25}$N$_3$+H requires 332.2.

Example 43
1-Hexyl-4-methyl-4-(3-(1H-1,3-imidazol-2-yl)phenyl)piperidine

To a solution of the hydrochloride salt of 1-benzyl-4-methyl-4-(3-(1H-1,3-imidazol-2-yl)phenyl)piperidine (Example 42, 40 mg, 0.11 mmol) and hexanal (15 µL, 0.12 mmol) in methanol (10 mL) was added 10% palladium on charcoal (50 mg). The mixture was heated at 50° C. and placed under hydrogen (415 kPa) for 5 h. Mass spectrometric evidence indicated no starting material, some desired product and a large amount of debenzylated material. Hexanal (15 µL, 0.12 mmol) and sodium borohydride (5 mg, 0.12 mmol) were added to the suspension and the mixture was left for 4 d. The reaction mixture was filtered, and the filtrate was concentrated in vacuo then partitioned between water (10 mL) and dichloromethane (20 mL). The layers were separated and the aqueous layer was further extracted with dichloromethane (20 mL). The organic extracts were washed with water (10 mL), dried over Na$_2$SO$_4$, filtered and concentrated in vacuo to give a crude oil which was purified by silica column chromatography eluting with ethyl acetate:hexane:0.88 ammonia (85:15:1) to give the title compound as a clear oil, and finally isolated as the hydrochloride salt, an extremely hygroscopic solid (11 mg, 29%).

NMR (CDCl$_3$, selected data for free base):0.85 (m, 3H), 1.45 (s, 3H), 2.4 (m, 2H), 2.8 (m, 2H), 3.9 (m, 2H), 7.1–7.4 (m, 4H), 7.6 (d, 1H), 7.8 (s, 1H).

MS (thermospray): M/Z (MH$^+$) 326.2; C$_{21}$H$_{31}$N$_3$+H requires 326.3.

Example 44
1-Hexyl-3,4-dimethyl-4-(3-(1H-1,2,4-triazol-3-yl)phenyl)piperidine To a solution of 1-hexyl-4-(3-(methoxycarbonimidoyl)phenyl)-3,4-dimethylpiperidine (Preparation 10, 200 mg, 0.35 mmol) in methanol (10 mL) was added a solution of formic acid hydrazide (30 mg, 0.5 mmol) in ethanol (20 mL). The resultant mixture was heated to reflux for 2 h and then concentrated in vacuo. The residual oil was heated at 100° C. for 20 minutes and then allowed to cool. The residue was purified by chromatography eluting with dichloromethane:methanol:0.88 ammonia (300:8:1) to give the title compound as a colourless oil (75 mg, 63%).

NMR (CDCl$_3$, selected data for the free base): 0.80 (d, 3H), 0.9 (m, 3H), 1.2–1.8 (m, 9H), 1.4 (s, 3H), 2.1–2.9 (m, 9H), 7.35–7.4 (m, 2H), 7.8 (d, 1H), 8.0 (s, 1H), 8.2 (s, 1H).

MS (thermospray): M/Z (MH$^+$) 341.3; $C_{21}H_{32}N_4$+H requires 341.3.

Example 45
1-Hexyl-3,4-dimethyl-4-(3-(1H-1,3-imidazol-2-yl)phenyl)piperidine

To a solution of the hydrochloride salt of 1-hexyl-4-(3-(methoxycarbonimidoyl)phenyl)-3,4-dimethylpiperidine (Preparation 10, assume 5.45 mmol) in methanol (10 mL) was added aminoacetaldehyde dimethyl acetal (620 mL, 5.7 mmol) and the reaction mixture was heated under reflux for 18 h and then allowed to cool. The mixture was concentrated in vacuo, 6 M hydrochloric acid (20 mL) was added and the reaction mixture was heated under reflux for 30 min after which it was stirred overnight at room temperature. It was then basified to pH 9–10 with aqueous sodium hydroxide solution and extracted with dichloromethane (3×100 mL). The combined extracts were dried over Na$_2$SO$_4$ and concentrated in vacuo to give a cream residue (2.6 g) which was purified by column chromatography on silica gel (120 g) eluting with CH$_2$Cl$_2$:EtOH:0.88 ammonia (150:8:1 altering to 100:8:1). This gave the title compound as a beige solid (0.94 g, 51%).

NMR (CDCl$_3$, selected data for the free base): 0.75 (d, 3H), 0.9 (t, 3H), 10 1.25–1.35 (m, 9H), 1.4–1.55 (m, 2H), 1.6 (m, 1H), 2.0 (m, 1H), 2.2–2.6 (m, 6H), 2.8 (m, 1H), 7.15 (br, 2H), 7.25 (d, 1H), 7.35 (t, 1H), 7.6 (d, 1H), 7.85 (s, 1H).

MS (thermospray): M/Z (MH$^+$) 340.3; $C_{22}H_{33}N_3$+H requires 340.3.

Example 46
1-Hexyl-3,4-dimethyl-4-(3-(1H-tetrazol-5-yl)phenyl)piperidine

To a solution of 4-(3-cyanophenyl)-1-hexyl-3,4-dimethylpiperidine (Preparation 6, 200 mg, 0.67 mmol) in anhydrous toluene (2 mL) was added trimethylsilyl azide (0.18 mL, 1.36 mmol) and di-n-butyltin oxide (17 mg, 0.07 mmol). The reaction mixture was stirred under nitrogen and heated at 100° C. for 3 days. The solvent was then removed in vacuo to give a red/brown residue (250 mg) which was purified by reversed phase preparative HPLC (condition 2). The appropriate fractions were combined to give a residue which was dissolved in t-butanol and water and freeze-dried overnight. This gave the acetate salt of the title compound as an orange oily solid.

NMR (CD$_3$OD, selected data for the acetate salt): 0.85–1.0 (m, 6H), 1.3–1.45 (m, 6H), 1.5 (s, 3H), 1.65–1.9 (m, 2H), 2.05 (m, 1H), 2.35–2.6 (m, 2H), 3.1–3.2 (t, 2H), 3.25–3.55 (m, 4H), 7.35 (d, 1H), 7.45 (t, 1H), 7.9 (d, 1H), 8.0 (s, 1H).

MS (thermospray): M/Z (MH$^+$) 342.2; $C_{20}H_{31}N_5$+H requires 342.3.

Example 47
1-Hexyl-3,4-dimethyl-4-(3-(1H-pyrazol-4-yl)phenyl)piperidine

A solution of 1-hexyl-3,4-dimethyl-4-(3-(1-((2-trimethylsilyl)ethoxy)methyl)-1H-pyrazol-4-yl)phenyl)piperidine (Preparation 25, 87 mg, 0.18 mmol) in 1,4-dioxane (1 mL) was treated with 2 N aqueous hydrochloric acid (1 mL) and heated at reflux for 1 h. The 1,4-dioxane was removed in vacuo and the residual solution was basified to pH 9–10 with saturated aqueous sodium hydrogencarbonate solution and extracted with ethyl acetate (4×5 mL). The combined extracts were filtered to remove a fine solid, dried over Na$_2$SO$_4$ and concentrated in vacuo to give a colourless oil (50 mg). Silica gel (2.5 g) column chromatography eluting with a gradient of ethyl acetate:hexane:0.88 ammonia (30:70:1 to 40:60:1) gave the title compound as a colourless residue (12 mg, 20% yield).

NMR (CDCl$_3$, selected data for the free base): 0.75–0.95 (m, 6H), 1.2–1.4 (m, 9H), 1.4–1.6 (m, 2H), 1.7 (m, 1H), 2.0–2.15 (m, 1H), 2.2–2.7 (m, 6H), 2.8 (m, 1H), 7.2 (m, 1H), 7.25–7.4 (m, 2H), 7.45 (s, 1H), 7.85 (s, 2H).

MS (thermospray): M/Z (MH$^+$) 340.4; $C_{22}H_{33}N_3$+H requires 340.3.

Example 48
4-(3-(5-Fluoro-1H-1,2,3-triazol-4-yl)phenyl)-1-hexyl-3,4-dimethylpiperidine To a solution of 1-hexanoyl-4-(3-(5-fluoro-1H-1,2,3-triazol-4-yl)phenyl)-3,4-dimethylpiperidine (Preparation 30, 20 mg, 0.054 mmol) in diethyl ether (0.8 mL) at 0° C. was added lithium aluminium hydride (1.0 M solution in tetrahydrofuran, 54 μL, 0.054 mmol) dropwise. The solution was then heated at reflux under a nitrogen atmosphere for 30 minutes before it was cooled back to 0° C. The reaction was cautiously quenched by the addition of 1 N sodium hydroxide (0.2 mL) and then ethyl acetate (3.0 mL) and solid sodium hydrogencarbonate were added. The mixture was stirred vigorously for 30 minutes and then filtered, washing with ethyl acetate. The filtrate was concentrated in vacuo and the residue was purified by column chromatography on silica gel eluting with ethyl acetate:hexane (2:1). The title compound was isolated as clear oil (8.0 mg, 40%).

NMR (CDCl$_3$, free base): 0.70 (d, 3H), 0.90 (t, 3H), 1.22–1.38 (m, 6H), 1.42 (s, 3H), 1.58–1.70 (m, 2H), 1.83 (m, 1H), 2.10 (m, 1H), 2.30–2.90 (m, 6H), 3.18 (m, 1H), 7.28 (d, 1H), 7.38 (t, 1H), 7.60 (d, 1H), 7.92 (s, 1H).

MS (thermospray): M/Z (MH$^+$) 359.1; $C_{21}H_{31}FN_4$+H requires 359.3.

Example 49
1-Hexyl-3,4-dimethyl-4-(3-(1,3-oxazol-5-yl)phenyl)piperidine

To a solution of 1-hexanoyl-3,4-dimethyl-4-(3-(1,3-oxazol-5-yl)phenyl)piperidine (Preparation 36, 292 mg, 0.83 mmol) in tetrahydrofuran (6.0 mL) at 0° C. was added lithium aluminium hydride (1.0 M solution in tetrahydrofuran, 0.80 mL, 0.80 mmol) dropwise over a few minutes. The solution was stirred at room temperature under a nitrogen atmosphere for 30 minutes and then heated at reflux for 30 minutes before it was cooled back to 0° C. The reaction was cautiously quenched by the addition of 1 N sodium hydroxide (1.0 mL) and then ethyl acetate (excess) and solid sodium hydrogencarbonate (excess) were added. The mixture was stirred vigorously for 1 h and then filtered through Celite®, washing with ethyl acetate. The filtrate was concentrated in vacuo and the residue was purified by column chromatography on silica gel eluting with ethyl acetate:hexane:ammonia (90:10:1). The title compound was isolated as clear oil (233 mg, 83%).

NMR (CDCl$_3$, free base): 0.80 (d, 3H), 0.90 (t, 3H), 1.22–1.36 (m, 6H), 1.37 (s, 3H), 1.40–1.58 (m, 2H), 1.64 (m, 1H), 2.10 (m, 1H), 2.22–2.64 (m, 6H), 2.83 (m, 1H), 7.28–7.50 (m, 4H), 7.59 (s, 1H), 7.92 (s, 1H).

MS (thermospray): M/Z (MH$^+$) 341.1; $C_{22}H_{32}N_2O$+H requires 341.3.

Example 50
1-Hexyl-3,4-dimethyl-4-(3-(1H-pyrazol-3-yl)phenyl)piperidine

To a solution of 4-(3-(3-dimethylaminopropenoyl)phenyl)-1-hexyl-3,4-dimethylpiperidine (Preparation 38, 117 mg, 0.32 mmol) in a mixture of methanol (5.0 mL) and water (1.0 mL) was added hydrazine hydrate (0.1 mL, 3.2 mmol). The mixture was heated at reflux for 2 h and then cooled to room temperature. The mixture was concentrated in vacuo and saturated aqueous sodium hydrogencarbonate (10 mL) was added. The aqueous layer was extracted with dichloromethane (3×10 mL), the combined organic layers were dried over $MgSO_4$, filtered and concentrated in vacuo. The residue was purified by column chromatography on silica gel eluting with ethyl acetate:hexane:0.88 ammonia (90:10:1). The title compound was isolated as clear oil (85 mg, 79%).

NMR ($CDCl_3$, free base): 0.80 (d, 3H), 0.87 (t, 3H), 1.22–1.58 (m, 11H), 1.65 (m, 1H), 2.05 (m, 1H), 2.22–2.62 (m, 6H), 2.83 (m, 1H), 6.60 (s, 1H), 7.26 (d, 1H), 7.38 (t, 1H), 7.53 (d, 1H), 7.60 (s, 1H), 7.70 (s, 1H).

MS (thermospray): M/Z ($MH^+$) 340.3; $C_{22}H_{33}N_3$+H requires 340.3.

Example 51
4-(3-(2-(Benzylsulfanyl)-1H-imidazol-4-yl)phenyl)-1-hexyl-3,4-dimethylpiperidine To a solution of 4-(3-(2-(benzylsulfanyl)-1H-imidazol-4-yl)phenyl)-1-hexanoyl-3,4-dimethylpiperidine (Preparation 41, 101 mg, 0.21 mmol) in tetrahydrofuran (2 mL) at 0° C. was added lithium aluminium hydride (1.0 M solution in tetrahydrofuran, 0.32 mL, 0.32 mmol) dropwise over a few minutes. The solution was stirred at room temperature under a nitrogen atmosphere for 1 h and then cooled back to 0° C. The reaction was cautiously quenched by the addition of 1 N sodium hydroxide (0.5 mL) and then ethyl acetate (10 mL) and solid sodium hydrogen-carbonate (excess) were added. The mixture was stirred vigorously for 30 minutes and then filtered through Celite®, washing with ethyl acetate. The filtrate was concentrated in vacuo to give the title compound as a clear oil (98 mg, 100%).

NMR ($CDCl_3$, free base): 0.80 (d, 3H), 0.90 (t, 3H), 1.22–1.36 (m, 6H), 1.37 (s, 3H), 1.40–1.58 (m, 2H), 1.64 (m, 1H), 2.05 (m, 1H), 2.22–2.70 (m, 6H), 2.85 (m, 1H), 4.21 (s, 2H), 7.18–7.60 (10H).

MS ($ESI^+$): M/Z ($MH^+$) 462.2; $C_{29}H_{39}N_3S$+H requires 462.3.

Example 52
1-Hexyl-4-(3-(1H-imidazol-4-yl)phenyl)-3,4-dimethylpiperdine

To a solution of 4-(3-(2-(benzylsulfanyl)-1H-imidazol-4-yl)phenyl)-1-hexyl-3,4-dimethylpiperidine (Example 51, 98 mg, 0.21 mmol) in ethanol (2 mL) at room temperature was added 1 N NaOH (1.5 mL) and Raney® nickel (0.5 g, 50% slurry in water). The reaction was stirred for 5 minutes and then filtered through Celite®, washing with ethanol. The filtrate was concentrated in vacuo and the residue was dissolved in ethyl acetate (5 mL). The organic layer was washed with saturated aqueous sodium hydrogencarbonate (5 mL), dried over $MgSO_4$, filtered and concentrated in vacuo. The residue was then purified by column chromatography on silica gel eluting with ethyl acetate:0.88 ammonia (100:1) and then ethyl acetate:methanol:0.88 ammonia (70:30:1). The title compound was obtained as a clear oil (13 mg, 19%).

NMR ($CDCl_3$, selected data for the free base): 0.80 (d, 3H), 0.85 (t, 3H), 1.22–1.36 (m, 6H), 1.38 (s, 3H), 1.40–1.58 (m, 2H), 1.64 (m, 1H), 2.10 (m, 1H), 2.22–2.70 (m, 6H), 2.85 (m, 1H), 7.18–7.38 (m, 4H), 7.50 (m, 1H), 7.70 (s, 1H).

MS (thermospray): M/Z ($MH^+$) 462.2; $C_{29}H_{39}N_3S$+H requires 462.3

Example 53
1-Hexyl-4-(3-(5-isoxazolyl)phenyl)-3,4-dimethylpiperidine

To a solution of 1-hexanoyl-4-(3-(5-isoxazoyl)phenyl)-3,4-dimethylpiperidine (Preparation 43, 41 mg, 0.12 mmol) in tetrahydrofuran (2 mL) at room temperature was added lithium aluminium hydride (1.0 M solution in tetrahydrofuran, 0.23 mL, 0.23 mmol,) dropwise over a few minutes. The solution was stirred at room temperature under a nitrogen atmosphere for 1 h and then cooled to 0° C. The reaction was cautiously quenched by the addition of 1 N sodium hydroxide (0.3 mL) and then ethyl acetate (10 mL) and solid sodium hydrogencarbonate (excess) were added. The mixture was stirred vigorously for 30 minutes and then filtered through Celite®, washing with ethyl acetate. The filtrate was concentrated in vacuo and the residue was purified by column chromatography on silica gel eluting with ethyl acetate:hexane (1:2). The title compound was obtained as a clear oil (20 mg, 51%).

NMR ($CDCl_3$, selected data for the free base): 0.78 (d, 3H), 0.88 (t, 3H), 1.22–1.36 (m, 6H), 1.37 (s, 3H), 1.40–1.58 (m, 2H), 1.64 (m, 1H), 2.05 (m, 1H), 2.22–2.70 (m, 6H), 2.85 (m, 1H), 6.50 (s, 1H), 7.38–7.43 (m, 2H), 7.58 (d, 1H), 7.75 (s, 1H), 8.27 (s, 1H).

MS ($ESI^+$): M/Z ($MH^+$) 341.2; $C_{22}H_{32}N_2O$+H requires 341.3.

Preparation of Starting Materials
Preparation 1: 1-Benzyl-3,4-dimethyl-4-(3-hydroxyphenyl)piperidine To 3,4-dimethyl-4-(3-hydroxyphenyl)piperidine (Reference 4, 6.01 g, 29.3 mmol) in N,N-dimethylformamide (100 mL) was added sodium hydrogencarbonate (2.95 g, 35.2 mmol) and benzyl bromide (4.20 mL, 35.2 mmol). The reaction mixture was heated at 70° C. overnight and then allowed to cool to room temperature. The solution was poured onto water (100 mL) and extracted with diethyl ether (5×60 mL). The combined organic extracts were washed with water (10 mL), dried over $MgSO_4$ and concentrated in vacuo to give a yellow oil which was used without further purification.

NMR ($CDCl_3$, selected data for the free base): 0.8 (d, 3H), 1.3 (s, 3H), 1.9 (m, 1H), 2.3–2.5 (m, 2H), 2.5–2.6 (m, 2H), 2.8 (m, 1H), 3.4 (d, 1H), 3.6 (d, 1H), 6.6 (d, 1H), 6.7 (s, 1H), 6.8 (d, 1H), 7.1 (t, 1H), 7.2–7.4 (m, 5H).

MS (thermospray): M/Z ($MH^+$) 296.1; $C_{20}H_{25}NO$+H requires 296.2.

Preparation 2: 1-Benzyl-3,4-dimethyl-4-(3-trifluoromethanesulfonyloxyphenyl)piperidine To 1-benzyl-3,4-dimethyl-4-(3-hydroxyphenyl)piperidine (Preparation 1, assume 29.3 mmol) in dichloromethane (100 mL) at room temperature was added triethylamine (8.1 mL, 58.5 mmol) and then N-phenyltrifluoromethanesulfonimide (15.7 g, 43.9 mmol). The mixture was stirred for 16 h at room temperature and then concentrated in vacuo, before 2 M sodium hydroxide (100 mL) and dichloromethane (100 mL) were added. After 2 h, the two layers were separated and the aqueous layer was extracted with dichloromethane (3×30 mL). The combined organic extracts were dried over $MgSO_4$, filtered and concentrated in vacuo to give the crude oil which was purified by column chromatography on silica gel, eluting with ethyl acetate:hexane:0.88 ammonia (5:95:1), to give a white solid (7.0 g, 55% over two steps).

NMR ($CDCl_3$, selected data for the free base): 0.8 (d, 3H), 1.3 (s, 3H), 1.6 (m, 1H), 2.0 (m, 1H), 2.3–2.4 (m, 2H), 2.5–2.6 (m, 2H), 2.9 (m, 1H), 3.5 (d, 1H), 3.6 (d, 1H), 7.1 (d, 1H), 7.2 (s, 1H), 7.2–7.4 (m, 7H).

MS (thermospray): M/Z (MH$^+$) 428.1; $C_{21}H_{24}F_3NO_3S+H$ requires 428.2.

Preparation 3: 1-Benzyl-4-(3-cyanophenyl)-3,4-dimethylpiperidine

To a degassed solution of 1-benzyl-3,4-dimethyl-4-(3-trifluoromethanesulfonyloxyphenyl)piperidine (Preparation 2, 7.0 g, 16.4 mmol) in N-methylpyrrolidinone (80 mL) under an atmosphere of nitrogen at room temperature was added potassium cyanide (2.16 g, 32.7 mmol), 1,1'-bis(diphenylphosphino)ferrocene (450 mg, 0.22 mmol) and palladium(II) acetate (180 mg, 0.22 mmol). The mixture was heated at 60° C. for 16 h and then cooled to room temperature. The mixture was partitioned between saturated sodium hydrogencarbonate (100 mL) and ethyl acetate (100 mL), the two layers were separated and the aqueous layer was extracted with ethyl acetate (2×50 mL). The combined organic extracts were washed with water (50 mL), dried over $Na_2SO_4$, filtered and concentrated in vacuo to give the crude product. This was purified by column chromatography on silica gel eluting with EtOAc:hexane:0.88 ammonia (5:95:1) to give the title compound as a white waxy solid (5.0 g, 100%).

NMR (CDCl$_3$, selected data for the free base): 0.8 (d, 3H), 1.3 (s, 3H), 1.6 (m, 1H), 2.2–2.5 (m, 2H), 2.5–2.6 (m, 2H), 2.9 (m, 1H), 3.5 (d, 1H), 3.6 (d, 1H), 7.2–7.7 (m, 9H).

MS (thermospray): M/Z (MH$^+$) 305.1; $C_{21}H_{24}N_2+H$ requires 305.2.

Preparation 4: 1-Hexyl-4-(3-hydroxyphenyl)-3,4-dimethylpiperidine

To 3,4-dimethyl-4-(3-hydroxyphenyl)piperidine (Reference 4, 100 g, 0.34 mol) in N,N-dimethylformamide (2 L), stirred under nitrogen, was added sodium hydrogencarbonate (100 g, 1.19 mol) and hexyl bromide (76 mL, 0.34 mol). The reaction mixture was heated for 2.5 h at 100° C., and then allowed to cool to room temperature and stirred overnight. The reaction mixture was filtered and the mother liquor was concentrated in vacuo. The residue was mixed with ethyl acetate:hexane (1:1, 500 mL) and the precipitate filtered off. Silica gel (200 g) was added and the mixture then concentrated to dryness. The silica-containing crude product was chromatographed using silica gel (1 kg) eluting with ethyl acetate:hexane (1:1), and then with ethyl acetate:0.88 ammonia (99:1) to give a pale oil (126 g, 93%).

NMR (CDCl$_3$, selected data for the free base):0.8 (d, 3H), 1.3 (s, 3H), 1.9 (m, 1H), 2.3–2.5 (m, 2H), 2.5–2.6 (m, 2H), 2.8 (m, 1H), 3.4 (d, 1H), 3.6 (d, 1H), 6.6 (d, 1H), 6.7 (s, 1H), 6.8 (d, 1H), 7.1 (t, 1H), 7.2–7.4 (m, 5H).

MS (thermospray): M/Z (MH$^+$) 296.1; $C_{20}H_{25}NO+H$ requires 296.2.

Preparation 5: 1-Hexyl-3,4-dimethyl-4-(3-trifluoromethanesulfonyloxyphenyl)piperidine To 1-hexyl-4-(3-hydroxyphenyl)-3,4-dimethylpiperidine (Preparation 4, 20 g, 69.2 mmol) in dry dichloromethane (200 mL) at room temperature was added triethylamine (16 mL, 114.7 mmol) and then N-phenyltrifluoromethanesulfonimide (37 g, 103.5 mmol). The mixture was stirred for 16 h at room temperature. Sodium hydroxide (200 mL of 1 M) was added and the organic layer was separated and concentrated in vacuo. The crude residue was dissolved in dichloromethane (200 mL) and 1 M sodium hydroxide (200 mL) was added at 0° C., the reaction mixture was stirred at room temperature for 30 minutes. The organic layer was separated and washed with 1 M sodium hydroxide (2×50 mL) whilst the aqueous layers were back-washed with dichloromethane (50 mL). The combined organic layers were dried over MgSO$_4$ and concentrated giving a yellow oil which was purified by column chromatography on silica gel using ethyl acetate:hexane (95:5 to 80:20) eluant to give a white solid (27.5 g, 94%).

NMR (CDCl$_3$, selected data for the free base): 0.75 (d, 3H), 0.9 (t, 3H), 1.25–1.4 (m, 9H), 7.1 (d, 1H), 7.2 (s, 1H), 7.3–7.4 (m, 2H).

Preparation 6: 4-(3-Cyanophenyl)-1-hexyl-3,4-dimethylpiperidine

To solution of 1-hexyl-3,4-dimethyl-4-(3-trifluoromethanesulfonyloxyphenyl)piperidine (Preparation 5, 500 mg, 1.19 mmol) in N-methylpyrrolidinone (2.5 mL) under nitrogen was added potassium cyanide (155 mg, 2.38 mmol). The reaction was evacuated and flushed with nitrogen three times. Catalytic amounts of palladium(II) acetate and 1,1'-bis(diphenylphosphino)ferrocene were added and the reaction mixture was heated to 60° C. After 3 h, the reaction was cooled to room temperature and quenched by pouring the mixture into saturated aqueous sodium hydrogencarbonate solution (50 mL). The product was extracted into ethyl acetate (3×30 mL). The combined organic extracts were dried over NaSO$_4$ and then concentrated in vacuo. The crude residue was purified by flash column chromatography on silica gel (15 g), eluting with ethyl acetate:hexane:0.88 ammonia (20:79:1 to 50:49:1), to give the product as an oil (346 mg, 98% yield)

NMR (CDCl$_3$, selected data for the free base): 0.70 (d, 3H), 0.9 (t, 3H), 1.2–1.4 (m, 9H), 7.35–7.6 (m, 4H)

MS (thermospray): M/Z (MH$^+$) 299.3; $C_{20}H_{30}N_2+H$ requires 299.2.

Preparation 7: 1-Benzyl-4-(3-hydroxyphenyl)-4-methylpiperidine

To 4-(3-hydroxyphenyl)-4-methylpiperidine (Preparation 48, 5.79 g, 30.3 mmol) in N,N-dimethylformamide (100 mL) was added sodium hydrogencarbonate (3.02 g, 36 mmol) and benzyl bromide (3.97 mL, 33.3 mmol). The reaction mixture was heated at 70° C. for 1 h and then allowed to cool to room temperature. The solution was poured onto water (100 mL) and extracted with diethyl ether (5×60 mL). The combined organic extracts were washed with water (10 mL), dried over MgSO$_4$ and concentrated in vacuo to give a crude oil which was purified by column chromatography on silica gel, using CH$_2$Cl$_2$:MeOH:0.88 ammonia (100:6:1) eluant to give the title compound as a clear oil (6.45 g, 80%).

NMR (CDCl$_3$, selected data for the free base): 1.2 (s, 3H), 1.7 (m, 2H), 2.05 (m, 2H), 2.4–2.6 (m, 4H), 6.6–7.3 (m, 9H), 8.2 (br.s, 1H).

Preparation 8: 1-Benzyl-4-methyl-4-(3-trifluoromethanesulfonyloxyphenyl)piperidine To 1-benzyl-4-(3-hydroxyphenyl)-4-methylpiperidine (Preparation 7, 6.45 g, 24.0 mmol) in dichloromethane (150 mL) at room temperature was added triethylamine (2.42 mL, 46 mmol) and then N-phenyltrifluoromethanesulfonimide (11.26 g, 31.5 mmol). The mixture was stirred for 16 h at room temperature before 1 M sodium hydroxide (100 mL) was added. After 25 min the two layers were separated and the aqueous layer was extracted with dichloromethane (3×30 mL). The combined organic extracts were washed with water (50 mL), dried over MgSO$_4$, filtered and then concentrated in vacuo to give the crude oil (12.5 g, 126%).

NMR (CDCl$_3$, selected data for the free base): 1.2 (s, 3H), 1.85 (m, 2H), 2.15 (m, 2H), 2.5–2.7 (m, 4H), 7.0–7.4 (m, 9H).

Preparation 9: 1-Benzyl-4-(3-cyanophenyl)-4-methylpiperidine

To a degassed solution of 1-benzyl-4-methyl-4-(3-trifluoromethanesulfonyloxyphenyl)piperidine (Preparation 8, 3.0 g, 7.26 mmol) in N-methylpyrrolidinone (30 mL) under an atmosphere of nitrogen at room temperature was added potassium cyanide (0.95 g, 14.4 mmol), 1,1'-bis (diphenylphosphino)ferrocene (200 mg, 0.37 mmol) and palladium(II) acetate (82 mg, 0.37 mmol). The mixture was heated at 65° C. and then cooled to room temperature. The mixture was partitioned between saturated sodium hydrogencarbonate (100 mL) and $CH_2Cl_2$ (100 mL), the two layers were separated and the aqueous layer was extracted with dichloromethane (2×50 mL). The combined organic extracts were washed with water (50 mL), dried over $Na_2SO_4$, filtered and concentrated in vacuo to give the crude product. This was purified by column chromatography on silica gel, eluting with EtOAc:hexane:0.88 ammonia (15:85:1), to give the title compound as a pale yellow oil (2.0 g, 95%).

NMR ($CDCl_3$, selected data for the free base): 1.25 (s, 3H), 1.8 (m, 2H), 2.1 (m, 2H), 2.4–2.6 (m, 4H), 7.2–7.7 (m, 9H).

MS (thermospray): M/Z ($MH^+$) 291.1; $C_{20}H_{22}N_2$+H requires 291.2.

Preparation 10: 1-Hexyl-4-(3-(methoxycarbonimidoyl) phenyl)-3,4-dimethylpiperidine Hydrogen chloride gas was bubbled through a solution of 4-(3-cyanophenyl)-1-hexyl-3,4-dimethylpiperidine (Preparation 6, 1.7 g, 5.70 mmol) in methanol (30 mL) for 5 min. The flask was sealed and the reaction mixture was allowed to stir for 16 h. The mixture was concentrated in vacuo and the residue was partitioned between water (50 mL) and dichloromethane (50 mL). The aqueous layer was carefully adjusted to pH 9 with solid sodium hydrogencarbonate. The layers were separated and the aqueous layer was extracted with dichloromethane (3×50 mL). The extracts were washed with water (20 mL), dried over $Na_2SO_4$, filtered and concentrated in vacuo to give the crude product as an oil (1.8 mg, 100% crude yield).

NMR ($CDCl_3$, selected data for the free base): 0.8 (d, 3H), 0.9 (t, 3H), 1.3–1.4 (m, 10H), 1.4–1.7 (m, 4H), 2.0 (m, 1H), 2.2–2.4 (m, 3H), 2.4–2.6 (m, 2H), 2.8 (m, 1H), 3.9 (m, 3H), 7.3–7.8 (m, 4H).

MS (thermospray): M/Z ($MH^+$) 331.2; $C_{21}H_{34}N_2O$+H requires 331.3.

Preparation 11: 1-Hexyl-3,4-dimethyl-4-(3-(ethoxycarbonimidoyl)phenyl)piperidine Hydrogen chloride gas was bubbled through a solution of 1-benzyl-4-(3-cyanophenyl)-3,4-dimethylpiperidine (Preparation 3, 150 mg, 0.50 mmol) in ethanol/THF (11 mL of 1:10) for 5 min. The flask was sealed and the reaction mixture was allowed to stir for 16 h. The mixture was concentrated in vacuo and the residue was partitioned between water (100 mL) and ethyl acetate (50 mL). The aqueous layer was carefully adjusted to pH 9 with 0.88 ammonia. The layers were separated and the aqueous layer was extracted with dichloromethane (3×50 mL). The extracts were washed with water (20 mL), dried over $Na_2SO_4$, filtered and concentrated in vacuo to give the crude product as an oil. This was purified by column chromatography on silica gel eluting with dichloromethane:methanol:0.88 ammonia (200:8:1) to give the title compound as a colourless oil (50 mg, 30%).

NMR ($CDCl_3$, selected data for the free base): 0.7 (d, 3H), 0.9 (t, 3H), 1.2–1.4 (m, 10H), 1.4 (t, 3H), 1.4–1.7 (m, 3H), 2.0 (m, 1H), 2.2–2.6 (m, 5H), 2.8 (m, 1H), 4.3 (q, 2H), 7.3–7.7 (m, 4H).

Preparation 12: 1-Benzyl-4-(3-(methoxycarbonimidoyl) phenyl)-4-methylpiperidine

Hydrogen chloride gas was bubbled through a solution of 1-benzyl-4-(3-cyanophenyl)-4-methylpiperidine (Preparation 9, 780 mg, 2.39 mmol) in methanol (30 mL) at 0° C. for 30. min. The flask was sealed and the reaction mixture was allowed to warm to room temperature before leaving for 5 d. The mixture was concentrated in vacuo and the residue was partitioned between water (20 mL) and dichloromethane (50 mL). The aqueous layer was carefully adjusted to pH 9 with solid potassium carbonate. The layers were separated and the aqueous layer was extracted with dichloromethane (25, then 10 mL). The extracts were washed with water (20 mL), dried over $Na_2SO_4$, filtered and concentrated in vacuo to give the crude product as an oil (760 mg, 99% crude yield).

NMR ($CDCl_3$, selected data for the free base): 1.25 (s, 3H), 1.8 (m, 2H), 2.1 (m, 2H), 2.4–2.6 (m, 4H), 7.2–7.7 (m, 9H).

MS (thermospray): M/Z ($MH^+$) 323.6; $C_{21}H_{26}N_2O$+H requires 323.2.

Preparation 13: Methyl 6-bromohexanoate

To a solution of 6-bromohexanoic acid (200 mg, 1.03 mmol) in dry methanol (2 mL) stirred under an atmosphere of nitrogen was added (trimethylsilyl)diazomethane (2.0 M in hexane, 0.60 mL, 1.2 mmol) dropwise. The reaction mixture was stirred at room temperature for 2.5 h, then concentrated in vacuo. The residue was partitioned between saturated aqueous sodium hydrogencarbonate solution (10 mL) and ether (10 mL). The phases were separated and the aqueous layer was further extracted with ether (2×10 mL). The combined extracts were dried over $Na_2SO_4$, filtered and concentrated in vacuo to give the crude product as a yellow oil (60 mg) which was used without further purification.

Preparation 14: 4-Methoxybutyl 4-bromobenzenesulfonate

To a solution of 4-methoxy-1-butanol (2.0 g, 19.2 mmol) in dichloromethane (20 mL) was added triethylamine (3.9 mL, 28.9 mmol) followed by 4-bromobenzenesulfonyl chloride (7.35 g, 28.9 mmol) and the reaction mixture was stirred overnight. Hydrochloric acid (20 mL of 2 N) was added and the aqueous phase washed with dichloromethane (2×10 mL). The combined organic layers were washed successively with aqueous saturated sodium hydrogencarbonate (20 mL) and then water (20 mL) and then dried over $MgSO_4$ and concentrated in vacuo. The product was obtained as a pale oil (6.10 g, 98%).

NMR ($CDCl_3$): 1.6 (m, 2H), 1.8 (m, 2H), 3.3 (s, 3H), 3.35 (m, 2H), 4.1 (m, 2H), 7.6–7.9 (m, 4H).

Preparation 15: 1-Iodo-4-methoxybutane

To a solution of 4-methoxybutyl 4-bromobenzenesulfonate (Preparation 14, 6.10 g, assume 18.8 mmol) in acetone (40 mL) was added sodium iodide (5.75 g, 38.3 mmol), and the reaction mixture was stirred overnight. The thick white suspension was filtered and the mother liquor was concentrated in vacuo. The brown residual oil was diluted with dichloromethane (20 mL) and washed with 10% sodium thiosulfate (20 mL) and then with brine (20 mL). The organic layer was dried over $MgSO_4$ and then concentrated in vacuo. The title product was obtained as a clear oil (3.76 g, 93%).

NMR ($CDCl_3$, selected data): 1.7 (m, 2H), 1.9 (m, 2H), 3.2 (m, 2H), 3.3 (s, 3H), 3.4 (m, 2H).

Preparation 16: 3-Ethoxypropyl 4-bromobenzenesulfonate

The title compound was prepared as for Preparation 14 substituting 4-methoxy-1-butanol with 3-ethoxy-1-propanol (2.0 g, 19.2 mmol) to give the product as a pale oil (6.8 g, 100%) and was used without further purification to prepare 1-ethoxy-3-iodopropane.

NMR ($CDCl_3$): 1.15 (t, 3H), 1.9 (m, 2H), 3.3–3.5 (m, 4H), 4.2 (t, 2H), 7.7–7.9 (m, 4H).

Preparation 17: 1-Ethoxy-3-iodopropane

The title compound was prepared as for Preparation 15 substituting the 4-methoxybutyl 4-bromobenzenesulfonate with 3-ethoxypropyl 4-bromobenzenesulfonate (Preparation 16, 6.8 g, assume 19.2 mmol) to give the product as a clear oil (4.0 g, 97%).

NMR (CDCl$_3$): 1.2 (t, 3H), 2.0 (m, 2H), 3.3 (t, 2H), 3.4–3.6 (m, 4H).

Preparation 18: 2-Propoxyethyl 4-bromobenzenesulfonate

The title compound was prepared as for Preparation 14 substituting the 4-methoxy-1-butanol with 2-propoxy-1-ethanol (2.0 g, 19.2 mmol) to give the product as a pale oil (5.9 g, 96%) which was used without further purification to prepare 1-ethoxy-3-iodopropane.

NMR (CDCl$_3$): 0.9 (t, 3H), 1.5 (m, 2H), 3.3 (t, 2H), 3.6 (m, 2H), 4.2 (m, 2H), 7.6–7.9 (m, 4H).

Preparation 19: 1-(2-Iodoethoxy)propane

The title compound was prepared as for Preparation 15 substituting the 4-methoxybutyl 4-bromobenzenesulfonate with 2-propoxyethyl 4-bromobenzenesulfonate (Preparation 18, 5.9 g, assume 18.2 mmol) to give the product as a clear oil (3.9 g, 95%).

NMR (CDCl$_3$): 0.9 (m, 3H), 1.6 (m, 2H), 3.3 (m, 2H), 3.5 (m, 2H), 3.7 (m, 2H),

Preparation 20: N,N-Diethylacrylamide

To a solution of acrylic acid (1.0 g, 13.8 mmol) in dichloromethane (10 mL) was added N-methylmorpholine (3.4 mL, 31.2 mmol) and 2-(3-dimethylaminopropyl)-3-ethylcarbodiimide hydrochloride (3.0 g, 15.7 mmol) and N,N-diethylamine (1.8 mL, 31.1 mmol). The reaction mixture was stirred overnight in a sealed tube. The reaction mixture was washed with saturated sodium hydrogencarbonate solution (10 mL), and the aqueous layer was further extracted with dichloromethane (10 mL). The combined organics were washed with 2 N hydrochloric acid (10 mL) and then brine before drying over MgSO$_4$, and concentrating in vacuo to give the product as a yellow oil (0.87 g, 49%).

NMR (CDCl$_3$): 1.1–1.3 (m, 6H), 3.3–3.5 (m, 4H), 5.65 (d, 1H), 6.3 (d, 1H), 6.5 (m, 1H).

MS (thermospray): M/Z (Na$^+$) 150.5; C$_7$H$_{13}$NO+Na requires 150.1.

Preparation 21: N-Benzylacrylamide

The title compound was prepared as for Preparation 20 substituting N,N-diethylamine with benzylamine (3.4 mL, 31.1 mmol) to give the product as a clear oil (2.2 g, 98%).

NMR (CDCl$_3$): 4.5 (d, 2H), 5.5 (d, 1H), 5.9 (br, 1H), 6.1 (m, 1H), 6.35 (d, 1H), 7.2–7.4 (m, 5H).

MS (thermospray): M/Z (MNa$^+$) 184.3; C$_{10}$H$_{11}$NO+Na requires 184.1.

Preparation 22: N-Propylacrylamide

The title compound was prepared as for Preparation 20 substituting the N,N-diethylamine with propylamine (2.6 mL, 31.1 mmol) to give the product as a clear oil (1.3 g, 83%).

NMR (CDCl$_3$): 0.9 (t, 3H), 1.55 (m, 2H), 3.3 (m, 2H), 5.6 (d, 1H), 6.1 (m, 1H), 6.3 (d, 1H).

Preparation 23: 2-((Ethanesulfonyl)amino)ethyl-1-ethanesulfonate

To a solution of ethanolamine (1 g, 16.4 mmol) in pyridine (13 mL) and dichloromethane (100 mL) was added slowly with stirring at 0° C. ethanesulfonyl chloride (7.8 mL, 82 mmol). The reaction mixture was stirred overnight. A slurry of water and ice (50 mL) was added to the reaction mixture and after stirring at room temperature for 30 minutes the aqueous layer was separated and washed with dichloromethane (20 mL). The combined organic layer was dried over MgSO$_4$ and concentrated in vacuo. to give a dark brown residue. The crude residue was purified by column chromatography on silica gel eluting with CH$_2$Cl$_2$:MeOH:0.88 ammonia (200:8:1) to give the title compound as a brown film (0.5 g, 12%).

NMR (CDCl$_3$): 1.4–1.6 (m, 6H), 3.1 (q, 2H), 3.2 (q, 2H), 3.5 (m, 2H), 4.35 (m, 2H), 8.6 (br, 1H).

MS (thermospray): M/Z (MNa$^+$) 268.0; C$_6$H$_{15}$NOS$_2$+Na requires 268.0.

Preparation 24: N-(2-Iodoethyl)-1-ethanesulfonamide

The title compound was prepared as for Preparation 15 substituting 4-methoxybutyl (4-bromobenzene)sulfonate with 2-((ethanesulfonyl)amino)ethyl-1-ethanesulfonate (Preparation 23, 0.40 g, 1.60 mmol) to give the product as a light brown oil (0.38 g, 90%).

NMR (CDCl$_3$): 1.4 (t, 3H), 3.1 (m, 2H), 3.3 (m, 2H), 3.5 (m, 2H), 4.45 (br, 1H).

Preparation 25: 1-Hexyl-3,4-dimethyl-4-(3-(1-((2-trimethylsilyl)ethoxy)methyl)-1H-pyrazol-4-yl)phenyl) piperidine A solution of 1-hexanoyl-3,4-dimethyl-4-(3-(1-((2-(trimethylsilyl)ethoxy)-methyl)-1H-pyrazol-4-yl)phenyl) piperidine (Preparation 26, 78 mg, 0.16 mmol) in anhydrous tetrahydrofuran (1 mL) was stirred under nitrogen, cooled in an ice bath and treated with 1.0 M lithium aluminium hydride in tetrahydrofuran (0.32 mL, 0.32 mmol) dropwise. The reaction mixture was allowed to warm to room temperature while stirring for 2¼ h then quenched with half-saturated aqueous ammonium chloride solution (5 mL). Extraction with ethyl acetate (3×5 mL), and drying over Na$_2$SO$_4$ and concentration in vacuo of the combined extracts gave a colourless oil (76 mg). This was purified by silica column chromatography eluting with a gradient of ethyl acetate:hexane:0.88 ammonia (10:90:1 to 20:80:1) to give the title compound as a colourless oil (63 mg, 84%).

NMR (CDCl$_3$, selected data for the free base): 0.0 (s, 9H), 0.75–0.85 (d, 3H), 0.85–1.0 (m, 5H), 1.2–1.4 (m, 9H), 1.4–1.55 (m, 2H), 1.6–1.8 (m, 1H), 2.0–2.1 (m, 1H), 2.2–2.65 (m, 6H), 2.75–2.9 (m, 1H), 3.6 (t, 2H), 5.45 (s, 2H), 7.15–7.25 (m, 1H), 7.25–7.35 (m, 2H), 7.4 (s, 1H), 7.8 (s, 2H).

MS (electrospray): M/Z (MH$^+$) 470.2; C$_{28}$H$_{47}$N$_3$OSi+H requires 470.4.

Preparation 26: 1-Hexanoyl-3,4-dimethyl-4-(3-(1-(2-((trimethylsilyl)ethoxy)methyl)-1H-pyrazol-4-yl)phenyl) piperidine A solution of tris(dibenzylideneacetone)dipalladium(0) (11 mg, 0.012 mmol) and triphenylarsine (7 mg, 0.023 mmol) in anhydrous N,N-dimethylformamide (0.5 mL) was stirred under nitrogen for 10 minutes. To this was added 4-(tributylstannyl)-1-(2-((trimethylsilyl)ethoxy)methyl)-1H-pyrazole (Preparation 27, 140 mg, 0.29 mmol), a solution of 1-hexanoyl-3,4-dimethyl-4-(3-trifluoromethanesulfonyloxyphenyl)piperidine (Preparation 28, 105 mg, 0.24 mmol) in anhydrous N,N-dimethylformamide (0.5 mL) and lithium chloride (21 mg, 0.50 mmol). The mixture was degassed by evacuating and flushing with nitrogen three times, then heated at 50° C. for 22 h. The solvent was removed in vacuo to give a dark oil (300 mg) which was purified by silica gel column chromatography eluting with a gradient of ethyl acetate:hexane:0.880 ammonia (20:80:1 to 30:70:1 to 40:60:1). This gave the title compound as a colourless oil (79 mg, 68%).

NMR (CDCl$_3$, selected data from a 9:7 mixture of rotamers): 0.0 (s, 9H), 0.6–0.75 (m, 3H), 0.8–1.0 (m, 5H), 1.2–1.4 (m, 4H), 1.45 (s, 3H), 1.5–1.75 (m, 3H), 2.05–2.5 (m, 4H), 2.9 (m, 0.56H), 3.15 (m, 0.44H), 3.4 (m, 0.44H), 3.55–3.65 (m, 1.12H+2H), 3.9 (m, 0.44H), 4.4 (m, 0.44H), 4.7 (m, 0.56H), 5.45 (s, 2H), 7.1–7.2 (m, 1H), 7.3–7.4 (m, 3H), 7.8 (s, 2H).

MS (thermospray): M/Z (MH⁺) 484.1; $C_{28}H_{45}N_3O_2Si+H$ requires 484.3.

Preparation 27: 4-(Tributylstannyl)-1-(2-((trimethylsilyl) ethoxy)methyl)-1H-pyrazole To a solution of 4-bromo-1-(2-((trimethylsilyl)ethoxy) methyl)-1H-pyrazole (Preparation 29, 300 mg, 1.08 mmol) in anhydrous tetrahydrofuran (1 mL) stirred under nitrogen at −78° C. was added n-butyl lithium (1.6 M in hexanes, 0.90 mL, 1.44 mmol) dropwise, maintaining a reaction mixture temperature below −70° C. The mixture was allowed to warm to −20° C. over 1 h, then cooled to −30° C. and treated with tributyltin chloride (0.30 mL, 1.11 mmol), maintaining the temperature below −20° C. The reaction mixture was kept cool in an ice/methanol bath and stirred for 1¼ h, allowing the temperature to rise to +20° C. The yellow solution given was quenched with half-saturated aqueous sodium chloride solution (5 mL) and extracted with ethyl acetate (3×5 mL). The combined extracts were dried over $Na_2SO_4$ and concentrated in vacuo to give a yellow oil (530 mg) which was purified by silica column chromatography eluting with a gradient of ethyl acetate:hexane (2:98 to 5:95). This gave the title compound as a pale yellow oil (150 mg, 28%).

NMR (CDCl₃, selected data): −0.05 (s, 9H), 0.8–1.05 (m, 17H), 1.2–1.4 (m, 6H), 1.45–1.6 (m, 6H), 3.55 (m, 2H), 5.45 (s, 2H), 7.4–7.5 (m, 2H).

MS (electrospray): M/Z (MH⁺) 489.1; $C_{21}H_{44}N_2OSiSn+H$ requires 489.2.

Preparation 28: 1-Hexanoyl-3,4-dimethyl-4-(3-trifluoromethanesulfonyloxyphenyl)piperidine To a solution of 1-hexanoyl-4-(3-hydroxyphenyl)-3,4-dimethylpiperidine (Preparation 34, 3.1 g, 10.1 mmol) in dichloromethane (30 mL) at room temperature was added triethylamine (2.82 mL, 20.2 mmol) followed by the addition of N-phenyltrifluoromethanesulfonimide (3.6 g, 15.1 mmol) portionwise. The reaction was stirred under a nitrogen atmosphere at room temperature for 16 h and then sodium hydroxide (2 N, 30 mL) was added. The bi-phasic mixture was stirred vigorously for 2 h, the two layers were then separated and the aqueous layer was extracted with dichloromethane (3×20 mL). The combined organic layers were dried over MgSO₄, filtered and concentrated in vacuo. The residue was then purified by column chromatography on silica gel eluting with ethyl acetate:hexane (1:2 and then 2:1). The title compound was obtained as a clear oil (3.6 g, 82%).

NMR (CDCl₃, selected data from a 7:5 mixture of rotamers): 0.55–0.65 (m, 3H), 0.85–0.95 (m, 3H), 1.23–1.75 (m, 10H), 2.02–2.48 (m, 4H), 2.92 (m, 0.58H), 3.15 (m, 0.42H), 3.38 (m, 0.42H), 3.60 (m, 1.16H), 3.90 (m, 0.42H), 4.40 (m, 0.42H), 4.74 (m, 0.58H), 7.05–7.15 (m, 2H), 7.28 (m, 1H), 7.40 (m, 1H).

MS (thermospray): M/Z (MH⁺) 436.4; $C_{20}H_{28}F_3NO_4S+H$ requires 436.2.

Preparation 29: 4-Bromo-1-(2-((trimethylsilyl)ethoxy) methyl)-1H-pyrazole

Sodium hydride (550 mg, 60% dispersion in oil, 13.75 mmol) under nitrogen was washed with hexane (2×10 mL) before being stirred as a suspension in anhydrous N,N-dimethylformamide (20 mL). 4-Bromo-1H-pyrazole (2.00 g, 13.6 mmol) was added portionwise and upon completion 1o of the addition the suspension was stirred at room temperature for 1¾ h, finally giving a clear solution. The solution was then cooled using an ice bath before 2-(trimethylsilyl)ethoxymethyl chloride (2.6 mL, 14.7 mmol) was added dropwise and the resulting suspension was stirred at room temperature for 2 h. The reaction mixture was then quenched with water (20 mL) and extracted with diethyl ether (3×20 mL). The combined extracts were washed with saturated aqueous sodium chloride solution (20 mL), dried over $Na_2SO_4$ and concentrated in vacuo to give a colourless oil (4.1 g). Purification by silica gel column chromatography eluting with ethyl acetate:hexane (5:95) gave the title compound as a colourless oil (3.49 g, 93%).

NMR (CDCl₃): 0.0 (s, 9H), 0.9 (t, 2H), 3.55 (t, 2H), 5.4 (s, 2H), 7.5 (s, 1H), 7.6 (s, 1H).

MS (thermospray): M/Z (MH⁺) 276.8; $C_9H_{17}BrN_2OSi+H$ requires 277.0.

Preparation 30: 1-Hexanoyl-4-(3-(5-fluoro-1H-1,2,3-triazol-4-yl)phenyl)-3,4-dimethylpiperidine A mixture of 4-(3-(2-fluoro-2-(phenylsulfonyl)ethenyl) phenyl)-1-hexanoyl-3,4-dimethylpiperidine (Preparation 31, 60 mg, 0.127 mmol) and sodium azide (17 mg, 0.261 mmol) in anhydrous N,N-dimethylformamide (1 mL) was stirred under nitrogen and heated at 100° C. for 4 days. The mixture was then cooled, diluted with ethyl acetate and washed with water. The organic phase was dried over $Na_2SO_4$ and concentrated in vacuo to give a residue which was purified by silica column chromatography to give the title compound as a colourless oil (20 mg, 42%).

NMR (CDCl₃, selected data from a 9:7 mixture of rotamers): 0.55–0.75 (m, 3H), 0.75–1.0 (m, 3H), 1.2–1.5 (m, 7H), 1.5–1.8 (m, 3H), 2.0–2.5 (m, 4H), 2.9 (m, 0.56H), 3.2 (m, 0.44H), 3.4 (m, 0.44H), 3.55–3.65 (m, 1.12H), 3.9 (m, 0.44H), 4.4 (m, 0.44H), 4.75 (m, 0.56H), 7.3–7.8 (m, 4H).

MS (thermospray): M/Z (MH⁺) 373.3; $C_{21}H_{29}FN_4O+H$ requires 373.2.

Preparation 31: 4-(3-(2-Fluoro-2-(phenylsulfonyl)ethenyl) phenyl)-1-hexanoyl-3,4-dimethylpiperidine To a solution of 4-(3-(2-fluoro-1-hydroxy-2-(phenylsulfonyl)ethyl)phenyl)-1-hexanoyl-3,4-dimethylpiperidine (Preparation 32, 70 mg, 0.143 mmol) in anhydrous dichloromethane (1 mL) stirred under nitrogen was added triethylamine (50 μL, 0.36 mmol) followed by methanesulfonyl chloride (13 μL, 0.17 mmol). The reaction mixture was stirred overnight at room temperature. The solvent was then removed in vacuo to give an oily solid which was purified by silica column chromatography eluting with ethyl acetate:hexane:0.88 ammonia (30:70:1). This gave the title compound (as a 1:1 mixture of E:Z isomers) as a colourless oil (61 mg, 90%).

NMR (CDCl₃, selected data): 0.44–0.65 (d, 3H), 0.85–0.95 (t, 3H), 1.25–1.35 (m, 4H), 1.4 (s, 3H), 1.55–1.75 (m, 3H), 7.0 (s, 0.5H), 7.1 (s, 0.5H), 7.25–7.45 (m, 4H), 7.55–7.65 (m, 2H), 7.65–7.75 (m, 1H), 8.0–8.05 (m, 2H).

MS (electrospray): M/Z (MNa⁺) 494.0; $C_{27}H_{34}FNO_3S+Na$ requires 494.2.

Preparation 32: 4-(3-(2-Fluoro-1-hydroxy-2-(phenylsulfonyl)ethyl)phenyl)-1-hexanoyl-3,4-dimethylpiperidine A solution of fluoromethyl phenyl sulfone (100 mg, 0.575 mmol) in anhydrous tetrahydrofuran (1 mL) was stirred under nitrogen, cooled to −78° C. and treated with n-butyl lithium (1.6 M in hexanes, 0.36 mL, 0.576 mmol) dropwise. The resulting yellow solution was stirred at −78° C. for 1¾ h over which time it darkened in colour. A solution of 4-(3-formylphenyl)-1-hexanoyl-3,4-dimethylpiperidine (Preparation 33, 180 mg, 0.57 mmol) in anhydrous tetrahydrofuran (2 mL) was added dropwise. The reaction mixture was then stirred at −78° C. for 1 h and then for a further 1 h over which. time it was allowed to warm to −40° C. before quenching by the addition of methanol (1 mL). The mixture was poured into water (10 mL) and extracted with ethyl acetate (3×10 mL). The combined organics were dried over $Na_2SO_4$ and concentrated in vacuo to give an orange oil (290 mg). Purification by silica column chromatography eluting with a gradient of ethyl acetate:hexane:0.88 ammonia (10:90:1 to 20:80:1 to 30:70:1 to 40:60:1) gave the title compound (as a 1:1 mixture of isomers) as a colourless oil (70 mg, 25%).

NMR ($CDCl_3$, selected data): 0.5–0.65 (m, 3H), 0.85–0.95 (m, 3H), 1.25–1.4 (m, 7H), 1.55–1.75 (m, 3H), 4.95–5.25 (m, 1.5H), 5.55–5.65 (m, 0.5H), 7.2–7.4 (m, 5H), 7.55–65 (m, 2H), 7.7–7.8 (m, 1H), 7.95–8.0 (m, 2H).

MS (electrospray): M/Z ($MNa^+$) 512.1; $C_{27}H_{36}FNO_4S+Na$ requires 512.2.

Preparation 33: 4-(3-Formylphenyl)-1-hexanoyl-3,4-dimethylpiperidine

To a solution of 1-hexanoyl-3,4-dimethyl-4-(3-vinylphenyl)piperidine (Preparation 35, 2.4 g, 7.67 mmol) in acetone (20 mL) at room temperature was added water (5 mL), 4-methylmorpholine N-oxide (1. 1 g, 9.20 mmol) and finally osmium tetroxide (3.83 mL, 2.5 wt % solution in 2-methyl-2-propanol). The yellow solution was stirred at room temperature for 1 h and then sodium periodate (4.92 g, 23.0 mmol) was added in one portion. After stirring the reaction for 3 h a heavy precipitate had developed and the reaction mixture was filtered through Celite®, washing with acetone. The filtrate was concentrated in vacuo, the crude oil was dissolved in dichloromethane, dried over $MgSO_4$, filtered and concentrated in vacuo. The residue was purified by column chromatography on silica gel eluting with ethyl acetate:hexane (1:1). The title compound was isolated as clear oil (2.0 g, 83%).

NMR ($CDCl_3$, selected data from a 1:1 mixture of rotamers): 0.66–0.65 (m, 3H), 0.85–0.95 (m, 3H), 1.23–1.78 (m, 10H), 2.10–2.48 (m, 4H), 2.92 (m, 0.5H), 3.15 (m, 0.5H), 3.38 (m, 0.5H), 3.60 (m, 1H), 3.90 (m, 0.5H), 4.41 (m, 0.5H), 4.73 (m, 0.5H), 7.44–7.58 (m, 2H), 7.70 (m, 1H), 7.78 (m, 1H), 10.0 (s, 1H).

MS (thermospray): M/Z ($MH^+$) 316.3; $C_{20}H_{29}NO_2+H$ requires 316.2.

Preparation 34: 1-Hexanoyl-4-(3-hydroxyphenyl)-3,4-dimethylpiperidine

To a stirred solution of 4-(3-hydroxyphenyl)-3,4-dimethylpiperidine (Reference 4, 3.8 g, 18.6 mmol) in dichloromethane (30 mL) at 0° C. was added triethylamine (3.9 mL, 27.8 mmol) followed by the dropwise addition of hexanoic anhydride (4.7 mL, 20.4 mmol) over 5 minutes. The reaction was stirred under a nitrogen atmosphere for 3 h at room temperature, and then quenched by the addition of saturated aqueous sodium hydrogencarbonate (50 mL). The two layers were separated and the aqueous layer was extracted with dichloromethane (3×50 mL). The combined organic layers were dried over $MgSO_4$, filtered and concentrated in vacuo. The residue was then purified by column chromatography on silica gel eluting with ethyl acetate:hexane (1:1). The title compound was obtained as a clear oil (4.5 g, 80%).

NMR ($CDCl_3$, selected data from a 7:4 mixture of rotamers): 0.60–0.70 (m, 3H), 0.85–0.95 (m, 3H), 1.24–1.75 (m, 10H), 2.00–2.50 (m, 4H), 2.92 (m, 0.64H), 3.15 (m, 0.36H), 3.38 (m, 0.36H), 3.60 (m, 1.28H), 3.85 (m, 0.36H), 4.40 (m, 0.36H), 4.77 (m, 0.64H), 5.75 (s, 0.36H), 6.60 (s, 0.64H), 6.68 (m, 1H), 6.75–6.85 (m, 2H), 7.18 (m, 1H).

MS (thermospray): M/Z ($MH^+$) 303.9; $C_{19}H_{29}NO_2$ requires 304.2.

Preparation 35: 1-Hexanoyl-3,4-dimethyl-4-(3-vinylphenyl)piperidine

To a solution of 1-hexanoyl-3,4-dimethyl-4-trifluoromethanesulfonyloxyphenyl)piperidine (Preparation 28, 3.0 g, 6.90 mmol) in tetrahydrofuran (30 mL) at room temperature were added sequentially vinyltributyltin (2.12 mL, 7.24 mmol), lithium chloride (585 mg, 13.8 mmol), and tetrakis(triphenylphosphine)palladium(0) (80 mg, 0.69 mmol). The mixture was heated at reflux under a nitrogen atmosphere for 1.5 h at which time a few crystals of 4-tert-butylcatechol were added, heating at reflux was then continued for 16 h. The mixture was cooled and concentrated in vacuo. The residue was then purified by column chromatography on silica gel eluting with ethyl acetate:hexane (1:10 and then 1:3). The title compound was obtained as a clear oil (2.1 g, 100%).

NMR ($CDCl_3$, selected data from a 4:3 mixture of rotamers): 0.55–0.65 (m, 3H), 0.85–0.95 (m, 3H), 1.23–1.75 (m, 10H), 2.02–2.46 (m, 4H), 2.92 (m, 0.57H), 3.15 (m, 0.43H), 3.38 (m, 0.43H), 3.60 (m, 1.14H), 3.90 (m, 0.43H), 4.40 (m, 0.43H), 4.74 (m, 0.57H), 5.24 (d, 1H), 5.73 (d, 1H), 6.70 (dd, 1H), 7.12–7.35 (m, 4H).

MS (thermospray): M/Z [$M+Na^+$] 336.2; $C_{21}H_{31}NO+Na$ requires 336.2.

Preparation 36: 1-Hexanoyl-3,4-dimethyl-4-(3-(1,3-oxazol-5-yl)phenyl)piperidine

To a solution of 4-(3-formylphenyl)-1-hexanoyl-3,4-dimethylpiperidine (Preparation 33, 0.27 g, 0.86 mmol) in methanol (5 mL) at room temperature was added potassium carbonate (118 mg, 0.86 mmol) and tosylmethyl isocyanide (167 mg, 0.86 mmol). The mixture was heated at reflux under a nitrogen atmosphere for 4 h, allowed to cool, and the solvent was removed in vacuo. The residue was purified by column chromatography on silica gel, eluting with hexane-:ethyl acetate (3:1 and then 1:1). The title compound was isolated as a clear oil (292 mg, 96%).

NMR ($CDCl_3$, selected data from a 1:1 mixture of rotamers): 0.55–0.65 (m, 3H), 0.85–0.95 (m, 3H), 1.20–1.41 (m, 4H), 1.42 (s, 3H), 1.57–1.74 (m, 3H), 2.08–2.48 (m, 4H), 2.92 (m, 0.5H), 3.15 (m, 0.5H), 3.39 (m, 0.5H), 3.60 (m, 1H), 3.90 (m, 0.5H), 4.41 (m, 0.5H), 4.74 (m, 0.5H), 7.21–7.50 (m, 5H), 7.88 (s, 1H).

MS ($ESI^+$): M/Z ($MH^+$) 355.1; $C_{22}H_{30}N_2O_2+H$ requires 355.2.

Preparation 37: 4-(3-Acetylphenyl)-1-hexyl-3,4-dimethylpiperidine

To a solution of 4-(3-cyanophenyl)-1-hexyl-3,4-dimethylpiperidine (Preparation 6, 791 mg, 2.65 mmol) in tetrahydrofuran (6.0 mL) at 0° C. was added methyllithium (1.4 M solution in ether, 2.46 mL, 3.45 mmol), which caused a darkening of the mixture. The solution was stirred under a nitrogen atmosphere at room temperature for 1 h and then poured onto water (10 mL). The aqueous layer was extracted with a mixture of ether and ethyl acetate (1:1, 3×10 mL). The combined organic layers were dried over $MgSO_4$, filtered and concentrated in vacuo. The crude residue, a yellow oil, was dissolved in acetone (10 mL) and 6 N HCl (10 mL) was added and the mixture was heated at reflux for 15 minutes. The mixture was cooled and the acetone removed in vacuo. The aqueous layer was then made basic (pH 10) with 2 N NaOH and extracted with dichloromethane (3×10 mL). The combined organic layers were dried over $MgSO_4$, filtered and concentrated in vacuo. The title compound was isolated as a clear oil (720 mg, 86%), and required no further purification.

NMR ($CDCl_3$, selected for free base): 0.78 (d, 3H), 0.85 (t, 3H), 1.22–1.37 (m, 9H), 1.40–1.56 (m, 2H), 1.65 (m, 1H), 2.05 (m, 1H), 2.22–2.64 (m, 6H), 2.64 (s, 3H), 2.83 (m, 1H), 7.40 (t, 1H), 7.50 (d, 1H), 7.78 (d, 1H), 7.91 (s, 1H).

MS (thermospray): M/Z (MH$^+$) 316.3; $C_{21}H_{33}NO+H$ requires 316.3.

Preparation 38: 4-(3-(3-Dimethylaminopropenoyl)phenyl)-1-hexyl-3,4-dimethylpiperidine To a solution of 4-(3-acetylphenyl)-1-hexyl-3,4-dimethylpiperidine (Preparation 37, 287 mg, 0.91 mmol) in N,N-dimethylformamide (1.2 mL) at room temperature was added N,N-dimethylformamide dimethylacetal (0.18 mL, 1.4 mmol). The mixture was heated at reflux for 24 h under a nitrogen atmosphere and then allowed to cool to room temperature. Hydrochloric acid (2.0 mL of 1 N) was then added and the mixture was stirred vigorously and then made basic with 2 N NaOH. The aqueous layer was extracted with ethyl acetate:diethyl ether (1:1, 3×5 mL) and then with dichloromethane (2×5 mL). The combined organic layers were dried over MgSO$_4$, filtered and concentrated in vacuo. The residue was purified by column chromatography on silica gel eluting first with ethyl acetate (100%) and then ethyl acetate:methanol:0.88 ammonia (90:10:1). The title compound was isolated as clear oil (128 mg, 38%).

NMR (CDCl$_3$, selected for free base): 0.78 (d, 3H), 0.85 (t, 3H), 1.22–1.37 (m, 9H), 1.40–1.56 (m, 2H), 1.65 (m, 1H), 2.05 (m, 1H), 2.22–2.62 (m, 6H), 2.83 (m, 1H), 5.70 (d, 1H), 7.30–7.39 (m, 2H), 7.65 (d, 1H), 7.79 (d, 1H), 7.84 (s, 1H).

MS (thermospray): M/Z (MH$^+$) 371.3; $C_{24}H_{38}N_2O+H$ requires 371.3.

Preparation 39: 4-(3-Acetylphenyl)-1-hexanoyl-3,4-dimethylpiperidine

To a solution of 1-hexanoyl-3,4-dimethyl-4-(trifluoromethanesulfonyloxyphenyl)piperidine (Preparation 28, 2.1 g, 4.7 mmol)) in N,N-dimethylformamide (15 mL) at room temperature were added sequentially, triethylamine (0.57 g, 5.6 mmol), butyl vinyl ether (3.0 mL, 23.4 mmol), 1,3-bis(diphenylphosphino)propane (69 mg, 0.17 mmol) and palladium(II) acetate (31 mg, 0.14 mmol). The mixture was heated at 80° C. under a nitrogen atmosphere for 18 h and then allowed to cool to room temperature. After the addition of 2 N HCl (20 mL), the mixture was stirred vigorously for 30 minutes and then poured onto dichloromethane (50 mL). The two layers were separated and the aqueous layer was extracted with dichloromethane (3×20 mL). The combined organic layers were washed with water, dried over MgSO$_4$, filtered and concentrated in vacuo. The residue was purified by column chromatography on silica gel eluting with ethyl acetate:hexane (1:2 and then 2:1). The title compound was isolated as clear oil (900 mg, 58%).

NMR (CDCl$_3$, selected data from a 1:1 mixture of rotamers): 0.55–0.65 (m, 3H), 0.85–0.95 (m, 3H), 1.20–1.38 (m, 4H), 1.42 (s, 3H), 1.57–1.78 (m, 3H), 2.08–2.48 (m, 4H), 2.60 (s, 3H), 2.92 (m, 0.5H), 3.15 (m, 0.5H), 3.39 (m, 0.5H), 3.60 (m, 1H), 3.90 (m, 0.5H), 4.41 (m, 0.5H), 4.73 (m, 0.5H), 7.41–7.53 (m, 2H), 7.79 (d, 1H), 7.85 (s, 1H).

MS (thermospray): M/Z (MH$^+$) 330.4; $C_{21}H_{31}NO_2+H$ requires 330.2.

Preparation 40: 4-(3-(2-Bromoacetyl)phenyl)-1-hexanoyl-3,4-dimethylpiperidine

To a solution of 4-(3-acetylphenyl)-1-hexanoyl-3,4-dimethylpiperidine (Preparation 39, 251 mg, 0.76 mmol) in tetrahydrofuran (10 mL) at −78° C. was added lithium bis(trimethylsilyl)amide (1.0 M solution in THF, 0.92 mL, 0.92 mmol) dropwise over 5 minutes. After the mixture had been stirred under a nitrogen atmosphere at −78° C. for 30 minutes, chlorotrimethylsilane (0.15 mL, 1.18 mmol) was added. The solution was stirred at −78° C. for 10 minutes and then warmed to 0° C. for 30 minutes before re-cooling to −78° C. Bromine (43 μL, 0.84 mmol) was added rapidly and the mixture was immediately warmed to room temperature, and then quenched with saturated aqueous potassium carbonate (10 mL). The aqueous layer was extracted with ethyl acetate (3×10 mL), and the combined organic layers were washed with brine (15 mL), dried over MgSO$_4$, filtered and concentrated in vacuo. The residue was a pale yellow oil (311 mg, 100%) which was used directly in the next step.

NMR (CDCl$_3$, selected data from a 1:1 mixture of rotamers): 0.55–0.65 (m, 3H), 0.85–0.95 (m, 3H), 1.20–1.38 (m, 4H), 1.42 (s, 3H), 1.57–1.78 (m, 3H), 2.08–2.48 (m, 4H), 2.92 (m, 0.5H), 3.15 (m, 0.5H), 3.39 (m, 0.5H), 3.60 (m, 1H), 3.90 (m, 0.5H), 4.41 (m, 0.5H), 4.42 (s, 2H), 4.74 (m, 0.5H), 7.41–7.55 (m, 2H), 7.80 (d, 1H), 7.91 (s, 1H).

MS (thermospray): M/Z (MH$^+$) 407.9; $C_{21}H_{30}BrNO_2+H$ requires 408.2.

Preparation 41: 4-(3-(2-(Benzylsulfanyl)-1H-imidazol-4-yl)phenyl)-1-hexanoyl-3,4-dimethylpiperidine To a solution of 4-(3-(2-bromoacetyl)phenyl)-1-hexanoyl-3,4-dimethylpiperidine (Preparation 40, 311 mg, 0.76 mmol) in N,N-dimethylformamide (5 mL) at room temperature was added solid potassium carbonate (136 mg, 0.99 mmol) and 2-benzyl 2-thiopseudourea hydrochloride (201 mg, 0.99 mmol). The mixture was heated at 80° C. under a nitrogen atmosphere for 1 h, cooled to room temperature and then poured onto a mixture of diethyl ether (10 mL) and water (10 mL). The two layers were separated and the aqueous layer was extracted with diethyl ether and ethyl acetate (1:1, 3×10 mL). The combined organic layers were washed with brine (20 mL), dried over MgSO$_4$, filtered and concentrated in vacuo. The residue was then purified by column chromatography on silica gel eluting with ethyl acetate:hexane (1:1 and then 9:1). The title compound was obtained as a clear oil (101 mg, 28%).

NMR (CDCl$_3$, selected data from a 1:1 mixture of rotamers): 0.55–0.65 (m, 3H), 0.85–0.95 (m, 3H), 1.20–1.42 (m, 7H), 1.55–1.77 (m, 3H), 2.08–2.48 (m, 4H), 2.92 (m, 0.5H), 3.10 (m, 0.5H), 3.35 (m, 0.5H), 3.58 (m, 1H), 3.86 (m, 0.5H), 4.22 (s, 2H), 4.39 (m, 0.5H), 4.68 (m, 0.5H), 7.10–7.80 (m, 10H).

Preparation 42: 4-(3-(3-Dimethylaminopropenoyl)phenyl-1-hexanoyl-3,4-dimethyl)piperidine To a solution of 4-(3-acetylphenyl)-1-hexanoyl-3,4-dimethylpiperidine (Preparation 39, 65 mg, 0.20 mmol) in N,N-dimethylformamide (1.0 mL) at room temperature was added N,N-dimethylformamide dimethyl acetal (0.1 mL, 0.75 mmol). The mixture was heated at 100° C. for 12 h under a nitrogen atmosphere and then cooled to room temperature. Hydrochloric acid (4.0 mL of 1 N) was added and the aqueous layer was extracted with ethyl acetate (3×5 mL). The combined organic layers were washed with water (2×5 mL), dried over MgSO$_4$, filtered and concentrated in vacuo. The title compound was isolated as clear oil (76.1 mg, 100%).

NMR (CDCl$_3$, selected data from a 1:1 mixture of rotamers): 0.55–0.65 (m, 3H), 0.85–0.90 (m, 3H), 1.20–1.38 (m, 4H), 1.41 (s, 3H), 1.57–1.78 (m, 3H), 2.08–2.48 (m, 4H), 2.92 (m, 0.5H), 3.15 (m, 0.5H), 3.39 (m, 0.5H), 3.58 (m, 1H), 3.88 (m, 0.5H), 4.39 (m, 0.5H), 4.70 (m, 0.5H), 5.66 (d, 1H), 7.30–7.38 (m, 2H), 7.62 (m, 1H), 7.78 (s, 1H), 7.81 (d, 1H).

Preparation 43: 1-Hexanoyl-4-(3-(5-isoxazoyl)phenyl)-3,4-dimethylpiperidine

To a solution of 4-(3-(3-dimethylaminopropenoyl)phenyl)-1-hexanoyl-3,4-dimethylpiperidine (Preparation 42, 76.1 mg, 1.98 mmol) in a mixture of methanol (2 mL) and water (1 mL) was added hydroxylamine hydrochloride (41 mg, 0.59 mmol). The mixture was heated at reflux for 5 h and then stirred at room temperature for 48 h. The mixture was concentrated in vacuo and then partitioned between ethyl acetate (3 mL) and water (3 mL). The two layers were separated and the aqueous layer was extracted with ethyl acetate (1×5 mL). The combined organic layers were dried over $MgSO_4$, filtered and concentrated in vacuo. The residue was purified by column chromatography on silica gel eluting with ethyl acetate:hexane (1:1). The title compound was obtained as a clear oil (41 mg, 59%).

NMR ($CDCl_3$, selected data from a 1:1 mixture of rotamers): 0.55–0.60 (m, 3H), 0.85–0.90 (m, 3H), 1.20–1.38 (m, 4H), 1.42 (s, 3H), 1.57–1.78 (m, 3H), 2.08–2.48 (m, 4H), 2.92 (m, 0.5H), 3.15 (m, 0.5H), 3.39 (m, 0.5H), 3.60 (m, 1H), 3.91 (m, 0.5H), 4.40 (m, 0.5H), 4.72 (m, 0.5H), 6.50 (s, 1H), 7.25–7.35 (m, 1H), 7.41 (t, 1H), 7.55–7.75 (m, 1H), 7.70 (s, 1H), 8.30 (s, 1H).

MS ($ESI^+$): M/Z ($MH^+$) 355.1; $C_{22}H_{30}N_2O_2$+H requires 355.2.

Preparation 44: 3,4-Dimethyl-4-(3-(1H-1,2,3-triazol-4-yl) phenyl)piperidine

A solution of 1-benzyl-3,4-dimethyl-4-(3-(1H-1,2,3-triazol-4-yl)phenyl)piperidine (Example 2, 2.36 g, 6.8 mmol) and 10% palladium on charcoal (400 mg) in methanol (100 mL) was stirred at 60° C. overnight under a hydrogen atmosphere (345 kPa). The suspension was filtered through a layer of Celite® and the filtrate was concentrated in vacuo to give a cream solid (1.72 g, 99%).

NMR ($CDCl_3$, selected data from the free base): 0.8 (d, 3H), 1.5 (s, 3H), 7.3 (d, 1H), 7.4 (t, 1H), 7.6 (d, 1H), 7.8 (s, 1H), 8.05 (s, 1H).

MS (thermospray): M/Z ($MH^+$) 257.1; $C_{15}1H_2ON_4$+H requires 257.2.

Preparation 45: 4-Methyl-4-(3-(1H-1,2,4-triazol-3-yl) phenyl)piperidine

To a solution of the hydrochloride salt of 1-benzyl-4-methyl-4-(3-(1H-1,2,4-triazol-3-yl)phenyl)piperidine (Example 39, 218 mg, 0.59 mmol) in methanol (30 mL) was added 10% palladium on charcoal. The resultant suspension was heated at 60° C. and placed under hydrogen (415 kPa) overnight. The suspension was filtered through a layer of Celite® and the filtrate was concentrated in vacuo to give the title compound (150 mg, 91%).

NMR ($CD_3OD$, selected data for the free base): 1.35 (s, 3H), 2.05 (m, 2H), 2.45 (m, 2H), 7.55 (m, 2H), 7.9–8.8 (m, 3H).

MS (thermospray): M/Z ($MH^+$) 243.1; $C_{14}H_{18}N_4$+H requires 243.2.

Preparation 46: 1-(2-Bromoethyl)-3-methylbenzene

To cooled solution of 3-methylphenethyl alcohol (3.0 g, 22 mmol) in ether (6 mL) and pyridine (0.3 mL) at 0° C. under nitrogen was added dropwise phosphorus tribromide (2.7 mL, 28.6 mmol) maintaining the temperature at 0° C. The reaction mixture was then heated to 50° C. for 4 h, before cooling to room temperature and pouring onto icewater. The product was extracted from the ice slurry with ether (3×50 mL) and the combined organic layers were washed sequentially with saturated aqueous sodium hydrogencarbonate (100 mL), water (100 mL) and then brine (100 mL). The organic fraction was then dried over $MgSO_4$, and concentrated in vacuo. The product was purified by silica gel column chromatography eluting with ethyl acetate:hexane (2:98), and finally isolated as a clear oil (1.8 g, 41%).

NMR ($CDCl_3$, selected data): 2.3 (s, 3H), 3.05 (m, 2H), 3.6 (m, 2H), 6.95–7.05 (m, 3H), 7.2 (m, 1H).

Preparation 47: 3-(Tetrahydro-3-furanyl)propionic Acid

Commercially available 3-furanacrylic acid (10 g, 72.5 mmol) in industrial methylated spirits (50 mL) was hydrogenated at 415 kPa over 10% palladium on charcoal (1 g). The catalyst was removed by filtration through Celite® and the filtrate was concentrated in vacuo to give the product as a colourless oil.

NMR (selected data): 1.4–1.9 (m, 3H), 2.0–2.4 (m, 3H), 3.3–4.0 (m, 4H), 9.0 (br, 1H).

Preparation 48: 4-(3-Hydroxyphenyl)-4-methylpiperidine

4-Methyl-4-(3-(1-methylethoxy)phenyl)-1-piperidinecarboxylic acid phenyl ester (Preparation 49, 2.4 g, 6.80 mmol) was heated under reflux in 1:1 47% aqueous HBr:glacial acetic acid (8 mL) for 16 h. The solution was allowed to cool to room temperature and water (5 mL) was added. The aqueous layer was extracted with methyl tert-butyl ether (3×10 mL) to remove the phenol by-product. The pH was adjusted to 10.3–10.5 with 15% sodium hydroxide and the mixture was left at room temperature for 2 h to allow the product to precipitate. After cooling to 0° C. the precipitate was filtered and washed with cold water (5 mL) to give the title compound as a solid (776 mg, 60%).

NMR ($CD_3OD$, selected data from the free base): 1.2 (s, 3H), 1.6–1.7 (m, 2H), 2.0–2.1 (m, 2H), 2.7–2.8 (m, 2H), 2.8–2.9 (m, 2H), 6.6 (d, 1H), 6.8 (s, 1H), 6.85 (d, 1H), 7.15 (t, 1H).

MS (thermospray): M/Z ($MH^+$) 192.4; $C_{12}H_{17}NO$+H requires 192.1.

Preparation 49: 4-Methyl-4-(3-(1-methylethoxy)phenyl)-1-piperidine-carboxylic Acid Phenyl Ester To 1-ethyl-4-methyl-4-(3-(1-methylethoxy)phenyl) piperidine (Preparation 50, 3.98 g, 15.23 mmol) in toluene (30 mL) at 85° C. was slowly added phenyl chloroformate (2.1 mL, 16.75 mmol) and the mixture was then heated at reflux for 16 h. The solution was cooled to 45° C. and 50 wt. % aqueous sodium hydroxide (2 mL) was added. Once the solution had reached room temperature the organic layer was separated and washed with methanol:1 N HCl (1:1, 3×10 mL), methanol:1 N sodium hydroxide (1:1, 12 mL) and then water (20 mL). The organic layer was dried ($MgSO_4$) and concentrated in vacuo to give the crude product. This was purified by silica column chromatography using ethyl acetate:hexane (20:80) to give the title compound as an oil (2.5 g, 45% over three steps).

NMR ($CDCl_3$, selected data): 1.3 (s, 3H), 1.4 (d, 6H), 1.75 (m, 2H), 2.15 (m, 2H), 3.4–3.8 (m, 4H), 4.6 (m, 1H), 6.7–7.2 (m, 9H).

MS (thermospray): M/Z ($MNH_4+$) 371.2; $C_{22}H_{27}NO_3$+$NH_4$ requires 371.2.

Preparation 50: 1-Ethyl-4-methyl-4-(3-(1-methylethoxy) phenyl)piperidine (i) To 1-ethyl-1,2,3,6-tetrahydro-4-(3-(1-methylethoxy) phenyl)pyridine (Preparation 51, 4.2 g, 15.97 mmol) in tetrahdrofuran (30 mL) at −10° C. was added n-butyllithium (1.6 M in hexanes, 15.0 mL, 24.0 mmol) over 20 min via a syringe at which point a deep red colour persisted. After 15 min the reaction mixture was cooled to −50° C. and dimethyl sulfate (1.59 mL, 16.8 mmol) was added dropwise over 20 min. The resultant pale yellow/brown solution was stirred for another 20 min at −50° C., then it was poured onto an ice cold aqueous ammonia solution (60 mL) with rapid stirring. This mixture was extracted with ethyl acetate (3×30 mL) and the combined organic extracts were dried ($Na_2SO_4$) and concentrated in vacuo to give an orange oil which was used without further purification in the next step.

(ii) The crude orange oil was dissolved in MeOH (20 mL) and the solution was cooled to −5° C. Solid sodium borohydride (724 mg, 19.2 mmol) was added portionwise over 20 min and the mixture was then allowed to stir at room temperature for 3 h. Acetone (5 mL) and saturated sodium hydrogencarbonate (5 mL) were added and after 5 min the mixture was concentrated in vacuo. Water (10 mL) was added and the aqueous layer was extracted with ethyl acetate (3×10 mL). The combined organic extracts were dried (MgSO$_4$), filtered and concentrated in vacuo to give the title compound as a crude oil (3.96 g) which was used without further purification.

NMR (CDCl$_3$, selected data for the free base): 1.1 (t, 3H), 1.2 (s, 3H), 1.35 (d, 6H), 2.35–2.6 (m, 6H), 4.6 (m, 1H), 6.7–7.2 (t, 4H).

MS (thermospray): M/Z (MH$^+$) 262.1; $C_{17}H_{27}NO+H$ requires 262.2.

Preparation 51: 1-Ethyl-1,2,3,6-tetrahydro-4-(3-(1-methylethoxy)phenyl)pyridine p-Toluenesulfonic acid (6.1 g, 31.9 mmol) was added to 1-ethyl-4-hydroxy-4-(3-(1-methylethoxy)phenyl)piperidine (Preparation 52, 4.2 g, 16.0 mmol) in toluene (50 mL), and the reaction mixture was heated at reflux for 3 h. The reaction mixture was allowed to cool to room temperature, water (20 mL) was added, and the resultant bi-phasic system was stirred vigorously for several minutes. The aqueous layer was basified with 2 N NaOH (10 mL) and the two phases were separated. The aqueous layer was then further extracted with ether (3×10 mL) and the combined organic layers were dried (MgSO$_4$) and concentrated to give a crude oil which was purified by silica column chromatography eluting with ethyl acetate:methanol:0.880 ammonia (96:3:1) to give the title compound as an oil (2.1 g, 54%).

NMR (CDCl$_3$, selected data for the free base): 1.15 (t, 3H), 1.3 (d, 6H), 2.45–2.7 (m, 6H), 3.15 (m, 2H), 4.55 (m, 1H), 6.05 (m, 1H), 6.75–7.1 (m, 4H).

MS (thermospray): M/Z (MH$^+$) 246.4; $C_{16}H_{23}NO+H$ requires 246.2.

Preparation 52: 1-Ethyl-4-hydroxy-4-(3-(1-methylethoxy)phenyl)piperidine

To a stirred solution of 1-bromo-3-(1-methylethoxy)benzene (5.0 g, 23 mmol) in anhydrous tetrahydrofuran (50 mL) at −78° C. under an atmosphere of nitrogen was added n-butyllithium (1.6 M in hexanes, 13.7 mL, 22 mmol) dropwise. The reaction mixture was stirred for 1 h at −78° C., before 1-ethyl-4-piperidone (2.95 mL, 22 mmol) was added dropwise at −78° C. over 15 minutes, and the reaction mixture was then warmed to −20° C. over 30 minutes. The solution was poured onto 2 N HCl (35 mL) and this was further acidified to pH 1 with concentrated HCl. Hexane (50 mL) was added and the two layers were separated. The organic layer was discarded and the aqueous layer was basified to pH 14 using solid NaOH pellets. The basic aqueous layer was extracted with hexane:ether (1:1, 5×50 mL) and the combined organic layers were dried (MgSO$_4$) and concentrated to give the title compound as a crude oil (4.2 g) which was used without further purification.

NMR (CDCl$_3$, selected data for the free base): 1.1 (t, 3H), 1.3 (d, 6H), 1.6 (s, 1H), 1.75 (d, 2H), 2.1–2.2 (m, 2H), 2.4–2.6 (m, 4H), 2.85 (m, 2H), 4.55 (m, 1H), 6.8–7.2 (m, 4H).

MS (thermospray): M/Z (MH$^+$) 264.4; $C_{16}H_{25}NO_2+H$ requires 264.2.

Preparation 53: 3-(Tetrahydro-2H-pyran-2-yl)propionic Acid

An aqueous solution of lithium hydroxide (4 mL, 2 M) was added to a solution of methyl 3-(tetrahydro-2H-pyran-2-yl)propionate (Preparation 54, 460 mg, 2.67 mmol) in tetrahydrofuran (16 mL) and the reaction mixture was heated under reflux for 10 h. The cooled reaction mixture was acidified with 2 N HCl to pH 1 and extracted with ethyl acetate (3×50 mL). The combined extracts were washed with brine (30 mL), dried (MgSO$_4$) and concentrated in vacuo to give the title compound as a colourless oil (460 mg, 67%).

NMR (CDCl$_3$): 1.10–1.20 (m, 1H), 1.40–1.60 (m, 4H), 1.70–1.90 (m, 3H), 2.50 (dt, 2H), 3.25–3.25 (m, 1H), 3.40 (m, 1H) and 3.95 (d, 1H).

MS (thermospray): M/Z [MH$^+$] 159.2; $C_8H_{14}O_3+H$ requires 159.1.

Preparation 54: Methyl 3-(tetrahydro-2H-pyran-2-yl)propionate

A mixture of methyl (E)- and (Z)-3-(tetrahydro-2H-pyran-2-yl)-2-propenoate (Reference 5, 537 mg, 3.15 mmol) was dissolved in methanol (10 mL) containing 10% palladium on charcoal (50 mg) and was subjected to hydrogenation at 415 kPa at room temperature overnight. The reaction mixture was filtered through Celite®, the residue was washed with methanol and the combined filtrates were concentrated in vacuo. The crude product was purified by silica (30 g) column chromatography eluting with diethyl ether:hexane (1:4) to give the title compound as a colourless oil (470 mg, 87%).

NMR (CDCl$_3$): 1.21 (q, 1H), 1.50–1.60 (m, 4H), 1.70–1.80 (m, 3H), 2.40 (m, 2H), 3.15–3.25 (m, 1H), 3.35 (t, 1H), 3.62 (s, 3H) and 3.90 (d, 1H).

References

1. C. M. Suter, A. W. Weston, *J. Am. Chem. Soc.*, 1941, 63, 602.
2. A. J. Blake, I. A. Fallis, R. O. Gould, S. Parsons, S. A. Ross and M. Schroder, *J. Chem. Soc., Dalton Trans.*, 1996, 4379.
3. Augstein, W. C. Austin, R. J. Boscott, S. M. Green and C. R. Worthing, *J. Med. Chem.*, 1965, 8, 356.
4. (a) J A Werner et al, *J. Org Chem.*, 1996, 61, 587; (b) C. H. Mitch, D. M. Zimmerman, J. D. Snoddy, J. K. Reel, and B. E. Cantrell, *J. Org. Chem.*, 1991, 56, 1660.
5. Priepke and R. Bruckner, *Chem. Ber.*, 1990, 123, 153.

Biological Activity

The Ki values of certain compounds of the present invention in the opioid receptor binding assays were determined, and the compounds of Examples 3, 11, 24, 26, 30, 38, 40, 46 and 47 were all found to have Ki values of 4000 nM or less for the ☒ receptor. The compounds of the invention also possess affinity at the δ and κ opioid receptors.

What is claimed is:

1. A compound of formula I,

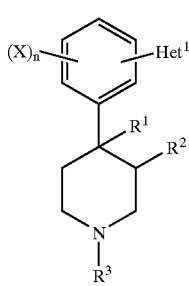

I wherein Het$^1$ represents a 5-membered heterocyclic ring comprising at least one atom selected from nitrogen, oxygen and sulfur, $C_1$–$C_6$ alkyl, $C_1$–$C_6$ alkoxy or C3-C6 cycloalkyl;

$R^1$ and $R^2$ are each independently H or $C_1$–$C_4$ alkyl;

$R^3$ represents; $C_1$–$C_{10}$ alkyl, $C_3$–$C_{10}$ alkenyl or $C_3$–$C_{10}$ alkynyl X is H;

n is 1;

or pharmaceutically, or veterinarily, acceptable derivatives thereof.

2. A compound as claimed in claim 1, wherein $Het^1$ is attached in the meta position relative to the piperidine ring.

3. A compound as claimed in claim 1, wherein $R^3$ represents saturated $C_1$–$C_{10}$ alkyl.

4. A compound as claimed in claim 1, wherein $Het^1$ is selected from the group consisting of furan, furoxan, imidazole, isothiazole, isoxazole, 1,2,4-oxadiazole, 1,2,5-oxadiazole, 1,3,4-oxadiazole, oxazole, pyrazole, pyrrole, tetrazole, 1,2,3-thiadiazole, 1,2,4-thiadiazole, 1,2,5-thiadiazole, 1,3,4-thiadiazole, thiazole, thiophene, 1,2,3-triazole or 1,2,4-triazole group.

5. A compound as claimed in claim 1, wherein $Het^1$ represents a 5-membered heterocyclic ring comprising at least one nitrogen and/or at least one oxygen atom.

6. A compound as claimed in claim 5, wherein $Het^1$ represents a 2- or 4-imidazole, tetrazole, 5-oxazole, 5-isoxazole, 4- or 5-pyrazole, 1,2,3- or 1,2,4-triazole group.

7. A pharmaceutical composition comprising a compound according to claim 1, in an effective amount, in admixture with a pharmaceutically, or a veterinarily, acceptable adjuvant, diluent or carrier.

8. A pharmaceutical composition as claimed in claim 7, which is a veterinary pharmaceutical composition.

9. A method of treating or preventing a disease mediated by an opiate receptor, which comprises administering a therapeutically effective amount of a compound as defined in claim 1, to a patient in need of such treatment.

10. A process for the preparation of a compound of formula I or a pharmaceutically, or veterinarily, acceptable derivative thereof:

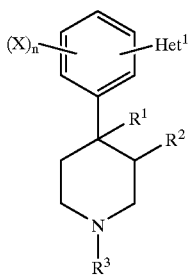

I wherein $Het^1$ represents a 5-membered heterocyclic ring comprising at least one atom selected from nitrogen, oxygen and sulfur.

$R^1$ and $R^2$ are each independently H or $C_1$–$C_4$ alkyl;

$R^3$ represents;

$C_1$–$C_{10}$ alkyl, $C_3$–$C_{10}$ alkenyl or $C_3$–$C_{10}$ alkynyl;

X is H;

n is 1;

which process comprises transition-metal-catalysed cross-coupling between a compound of formula II,

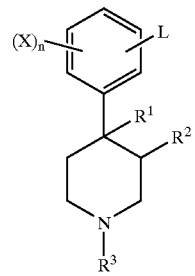

II wherein L is a leaving group, with a compound of formula III,

$Het^1$—M   III where M is a tin-containing moiety, a boron derivative or a zinc halide; and $Het^1$ is as defined above.

11. A process for the preparation of a compound of formula I or a pharmaceutically, or veterinarily, acceptable derivative thereof:

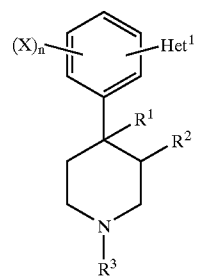

I wherein $Het^1$ represents 1H-1,2,3-triazol-4-yl;

$R^1$ and $R^2$ are each independently H or $C_1$–$C_4$ alkyl;

$R^3$ represents;

$C_1$–$C_{10}$ alkyl, $C_3$–$C_{10}$ alkenyl or $C_3$–$C_{10}$ alkynyl;

X is H;

n is 1;

which process comprises reaction of a nitrile of formula IV,

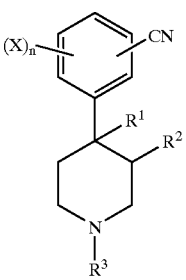

IV with a compound of formula V, $R^{12}CHN_2$   V wherein $R^{12}$ represents H.

12. A process for the preparation of a compound of formula I or a pharmaceutically, or veterinarily, acceptable derivative thereof:

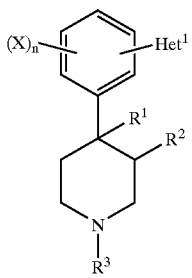

wherein Het¹ represents 1H-1,2,4-triazol-4-yl; optionally substituted by an $R^{12}$ group, wherein $R^{12}$ is H, $R^1$ and $R^2$ are each methyl;

$R^3$ represents;

Het², Het³ and Het⁴ independently represent 3-to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, ON, aryl, $C_1$–$C_4$ alkyl, $C_1$–$C_4$ alkoxy and $C_1$–$C_5$ alkanoyl (which latter three groups are optionally substituted by one or more halo atoms);

X is H;

n is 1, which process comprises reaction of an imidate of formula X,

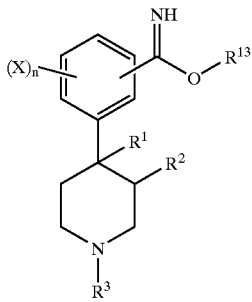

X wherein $R^{13}$ represents $C_1$–$C_6$ alkyl, with a compound of formula XI,

   XI wherein $R^{12}$ represents H.

13. A process for the preparation of a compound of formula I or a pharmaceutically, or veterinarily, acceptable derivative thereof:

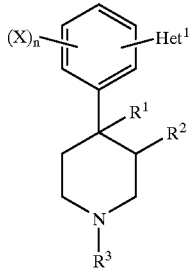

I wherein Het¹ represents 1H-1,3-imidazol-2-yl, optionally substituted by up to two $R^{12}$ groups, wherein $R^{12}$ is H, $R^1$ and $R^2$ are each independently H or $C_1$–$C_4$ alkyl;

$R^3$ represents;

$C_1$–$C_{10}$ alkyl, $C_3$–$C_{10}$ alkenyl or $C_3$–$C_{10}$ alkynyl;

X is H;

n is 1;

which process comprises reaction of a corresponding compound of formula X, as defined above, with a compound of formula XII,

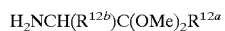   XII wherein independent substituents $R^{12a}$ and $R^{12b}$ represent $R^{12}$.

14. A process for the preparation of a compound of formula I or a pharmaceutically, or veterinarily, acceptable derivative thereof:

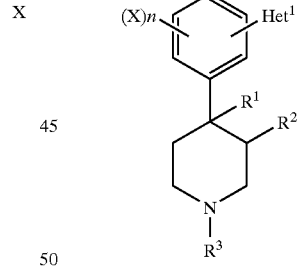

I wherein Het¹ represents 1H-1,3-imidazol-4-yl, $R^1$ and $R^2$ are each independently H or $C_1$–$C_4$ alkyl;

$R^3$ represents;

$C_1$–$C_{10}$ alkyl, $C_3$–$C_{10}$ alkenyl or $C_3$–$C_{10}$ alkynyl;

X is H;

n is 1;

which process comprises desulfurisation of a corresponding compound of formula I, but wherein which Het¹ represents 2-thiobenzylated 1H-1,3-imidazol-4-yl.

15. A process for the preparation of a compound of formula I or a pharmaceutically, or veterinarily, acceptable derivative thereof:

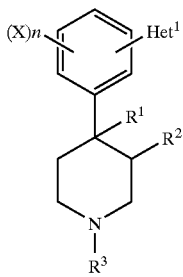

wherein Het[1] represents 2-thiobenzylated 1H-1,3-imidazol-4-yl;

R[1] and R[2] are each independently H or $C^1$–$C^4$ alkyl;

R[3] represents;

$C_1$–$C_{10}$ alkyl, $C_3$–$C_{10}$ alkenyl or $C_3$–$C_{10}$ alkynyl;

X is H;

n is 1;

which process comprises reaction of a corresponding α-halocarbonyl compound of formula XV,

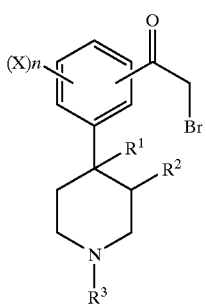

with 2-benzyl-2-thiopseudourea.

16. A process for the preparation of a compound of formula I or a pharmaceutically, or veterinarily, acceptable derivative thereof:

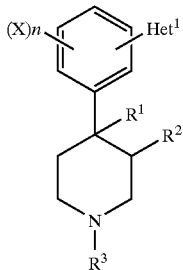

wherein Het[1] represents 1H-tetrazol-5-yl;

R[1] and R[2] are each independently H or $C_1$–$C_4$ alkyl;

R[3] represents;

$C_1$–$C_{10}$ alkyl, $C_3$–$C_{10}$ alkenyl or $C_3$–$C_{10}$ alkynyl

X is H;

n 1;

which process comprises reaction of a corresponding compound of formula IV:

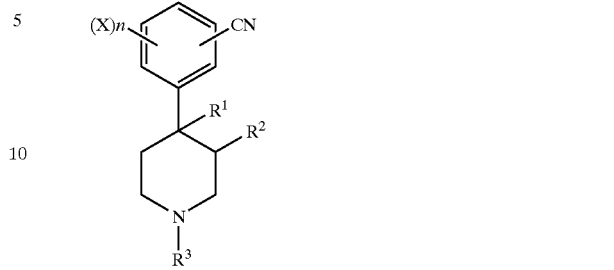

with a suitable source of an azide ion.

17. A process for the preparation of a compound of formula I or a pharmaceutically, or veterinarily, acceptable derivative thereof:

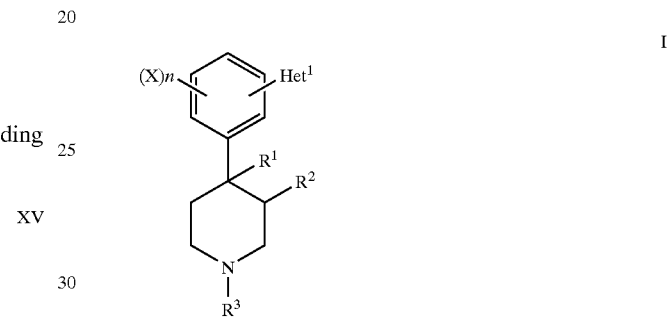

wherein Het[1] represents a 5-membered heterocyclic ring comprising at least one atom selected from nitrogen, oxygen and sulfur, R[1] and R[2] are each independently H or $C^1$–$C^4$ alkyl;

R[3] represents;

$C_2$–$C_{10}$ alkyl, $C_3$–$C_{10}$ alkenyl or $C_3$–$C_{10}$ alkynyl

X is H, n is 1;

which process comprises reduction of a corresponding compound of formula XVII,

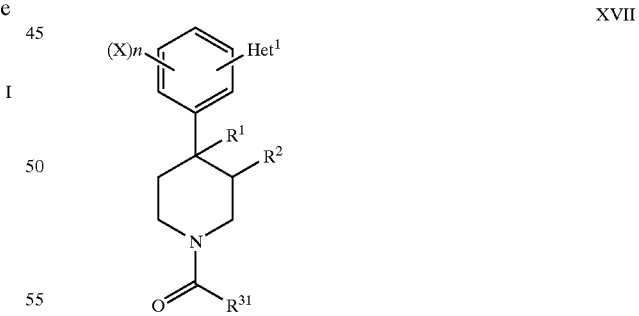

wherein R[31] represents H, $C_3$–$C_8$ cycloalkyl, Het[2], aryl, adamantyl, (which latter two groups are optionally substituted by one or more substituents selected from OH, nitro, amino, halo, CN, $CH_2CN$, $CONH_2$, $C_1$–$C_4$ alkyl, $C_1$–$C_4$ alkoxy and $C_1$–$C_5$ alkanoyl (which latter three groups are optionally substituted by one or more halo atoms)), $C_1$–$C_9$ alkyl, $C_2$–$C_9$ alkenyl or $C_2$–$C_9$ alkynyl, which alkyl, alkenyl or alkynyl groups are optionally substituted and/or terminated by one or more substituents selected from $OR^{8c}$, $S(O)_pR^{8d}$, CN, halo, $C_1$–$C_6$ alkoxy carbonyl, $C_2$–$C_6$ alkanoyl, $C_2$–$C_6$ alkanoyloxy, $C_3$–$C_5$ cycloalkyl, $C_4$–$C_9$ cycloalkanoyl, $N(R^{9a})S(O)_2R^{10}$, $Het^2$, aryl, adamantyl (which latter two groups are optionally substituted by one or more substituents selected from OH, nitro, amino, halo, CN, $CH_2CN$, $CONH_2$, $C_1-C_4$ alkyl, $C_1-C_4$ alkoxy and $C_1-C_5$ alkanoyl (which latter three groups are optionally substituted by one or more halo atoms)), or $-W-A^1-N(R^{9b})(R^{9c})$.

18. A process for the preparation of a compound of formula I or a pharmaceutically, or veterinarily, acceptable derivative thereof:

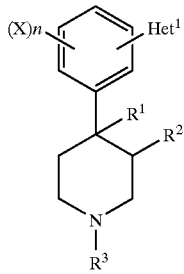

I wherein $Het^1$ represents 1H-pyrazol-3-yl;

$R^1$ and $R^2$ are each independently H or $C_1-C_4$ alkyl;
$R^3$ represents;
$C_1-C_{10}$ alkyl, $C_3-C10$ alkenyl or $C_3-C_{10}$ alkynyl
X is H, halo,
n is 1;

which process comprises reaction of a corresponding α,β-unsaturated ketone of formula XX,

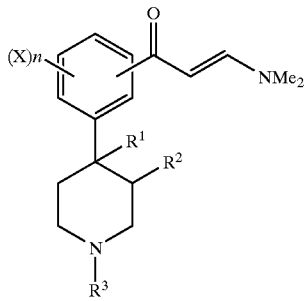

XX with hydrazine.

19. A process for the preparation of a compound of formula I or a pharmaceutically, or veterinarily, acceptable derivative thereof:

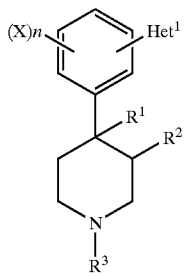

I wherein $Het^1$ 1H-pyrazol-4-yl;

$R^1$ and $R^2$ are each independently H or $C_1-C_4$ alkyl;
$R^3$ represents;
$C_1-C_{10}$ alkyl, $C_3-C_{10}$ alkenyl or $C_3-C_{10}$ alkynyl;
X is H,
n is 1;

which process comprises reaction of a corresponding compound of formula VI,

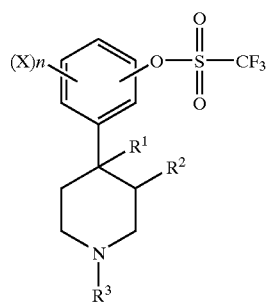

VI with a compound of formula XXI,

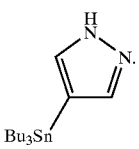

XXI

20. A process for the preparation of a compound of formula I or a pharmaceutically, or veterinarily, acceptable derivative thereof:

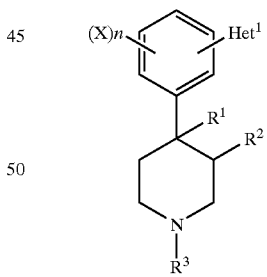

I wherein $Het^1$ represents oxazol-5-yl, thiazol-5-yl or imidazol-5-yl $R^1$ and $R^2$ are each independently H or $C_1-C_4$ alkyl;
$R^3$ represents;
$C_1-C_{10}$ alkyl, $C_3-C_{10}$ alkenyl or $C_3-C_{10}$ alkynyl;
X is H,
n is 1;

which process comprises reaction of a corresponding compound of formula XXII,

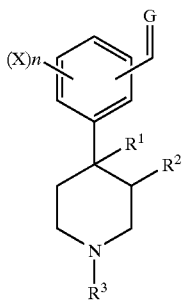

XXII wherein G represents NR$^{14}$, O or S, R$^{14}$ represents methyl with a compound of formula XXIII,

CNCH(R12)L$^2$  XXIII wherein L$^2$ represents a group capable, when attached to a C$_2$ alkylene unit, of undergoing 1,2-elimination (relative to the L$^2$ group);

and R$^{12}$ is wherein R$^{12}$ represents H.

21. A process for the preparation of a compound of formula I or a pharmaceutically, or veterinarily, acceptable derivative thereof:

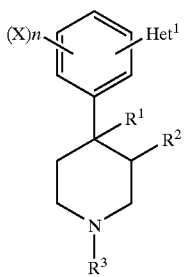

I wherein Het$^1$ represents isoxazol-5-yl;

R$^1$ and R$^2$ are each independently H or C$_1$–C$_4$ alkyl;

R$^3$ represents;

C$_1$–C$_{10}$ alkyl, C$_3$–C$_{10}$ alkenyl or C$_3$–C$_{10}$ alkynyl;

X is H, halo n is 1;

which process comprises reaction of a corresponding compound of formula XX:

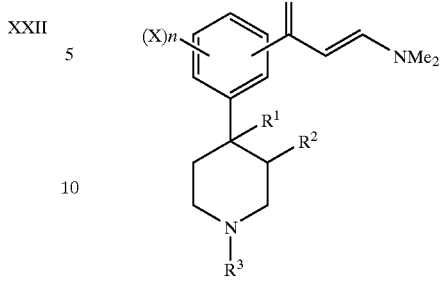

XX with a suitable form of hydroxylamine.

22. A process for the preparation of a compound of formula I or a pharmaceutically, or veterinarily, acceptable derivative thereof:

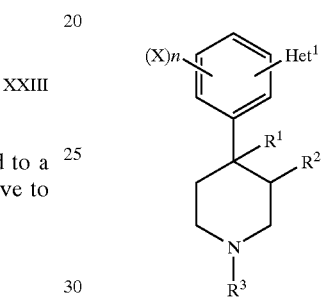

I wherein Het$^1$ represents 1H-1,2,3-triazol-4-yl,

R$^1$ and R$^2$ are each independently H or C$_1$–C$_4$ alkyl;

R$^3$ represents;

C$_1$–C$_{10}$ alkyl, C$_3$–C$_{10}$ alkenyl or C$_3$–C$_{10}$ alkynyl;

X is H, n is 1;

which process comprises reaction of a corresponding compound of formula XXVI,

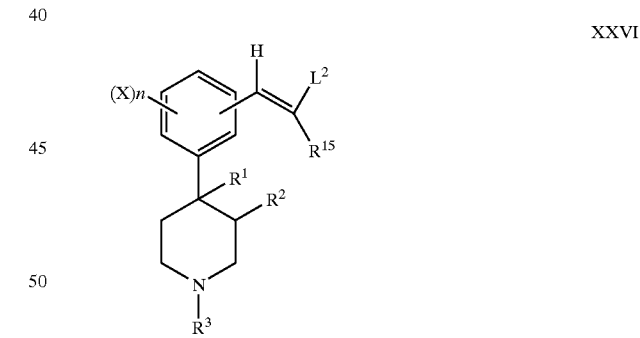

XXVI wherein R$^{15}$ represents H, and L$^2$ is a group capable, when attached to a C$_2$ alkylene unit, of undergoing 1,2-elimination relative to the L$^2$ group;

with a suitable source of an azide ion.

* * * * *